US011020058B2

(12) United States Patent
Lading et al.

(10) Patent No.: US 11,020,058 B2
(45) Date of Patent: Jun. 1, 2021

(54) METHODS AND DEVICES FOR CALCULATING BLOOD PRESSURE BASED ON MEASUREMENTS OF ARTERIAL BLOOD FLOW AND ARTERIAL LUMEN

(71) Applicant: QUALCOMM Incorporated, San Diego, CA (US)

(72) Inventors: Lars Lading, Roskilde (DK); David Boettcher Baek, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 413 days.

(21) Appl. No.: 15/186,228

(22) Filed: Jun. 17, 2016

(65) Prior Publication Data

US 2017/0231578 A1    Aug. 17, 2017

Related U.S. Application Data

(60) Provisional application No. 62/294,876, filed on Feb. 12, 2016.

(51) Int. Cl.
*A61B 5/00*  (2006.01)
*A61B 8/08*  (2006.01)
(Continued)

(52) U.S. Cl.
CPC ............ *A61B 5/7282* (2013.01); *A61B 5/002* (2013.01); *A61B 5/0004* (2013.01);
(Continued)

(58) Field of Classification Search
CPC .. A61B 8/04; A61B 8/06; A61B 8/488; A61B 5/0059; A61B 5/0261
See application file for complete search history.

(56) References Cited

U.S. PATENT DOCUMENTS 3,618,696 A    11/1971  Hurwitz
3,765,403 A    10/1973  Brenden
(Continued)

FOREIGN PATENT DOCUMENTS

CN    1235010        11/1999
CN    1235010 A  *  11/1999   ............. A61B 5/021
(Continued)

OTHER PUBLICATIONS

Pawlikowska-Pawlega et al. (2003). The study of quercetin action on human erythrocyte membranes. Biochemical Pharmacology, 66:605-612 (Year: 2003).*
(Continued)

*Primary Examiner* — Angela M Hoffa
*Assistant Examiner* — Younhee Choi
(74) *Attorney, Agent, or Firm* — Weaver Austin Villeneuve & Sampson LLP

(57) ABSTRACT

A system for calculating blood pressure may include a sensor system and a control system. The control system may be capable of controlling one or more sensors of the sensor system to take at least two measurements, the at least two measurements including at least one measurement taken at each of two or more different measurement elevations of a subject's limb. In some examples, the control system may be capable of determining a blood flow difference based on the at least two measurements, of determining a hydrostatic pressure difference based on the two or more different elevations of the at least two measurements and of estimating a blood pressure based on one or more values of blood flow, the hydrostatic pressure difference and the blood flow difference.

16 Claims, 26 Drawing Sheets

(51) Int. Cl.
  *A61B 8/00* (2006.01)
  *A61B 5/021* (2006.01)
  *A61B 5/026* (2006.01)
  *A61B 8/02* (2006.01)
  *A61B 8/04* (2006.01)
  *A61B 8/06* (2006.01)

(52) U.S. Cl.
  CPC ............ *A61B 5/0022* (2013.01); *A61B 5/021* (2013.01); *A61B 5/0261* (2013.01); *A61B 5/681* (2013.01); *A61B 8/02* (2013.01); *A61B 8/04* (2013.01); *A61B 8/06* (2013.01); *A61B 8/0883* (2013.01); *A61B 8/0891* (2013.01); *A61B 8/4227* (2013.01); *A61B 8/4281* (2013.01); *A61B 8/4411* (2013.01); *A61B 8/4427* (2013.01); *A61B 8/4483* (2013.01); *A61B 8/461* (2013.01); *A61B 8/488* (2013.01); *A61B 8/5223* (2013.01); *A61B 8/54* (2013.01); *A61B 8/56* (2013.01); *A61B 5/026* (2013.01); *A61B 2560/0261* (2013.01); *A61B 2560/0475* (2013.01)

(56) References Cited

U.S. PATENT DOCUMENTS

| | | | |
|---|---|---|---|
| 3,936,791 A | | 2/1976 | Kossoff et al. |
| 4,131,021 A | | 12/1978 | Mezrich et al. |
| 4,633,714 A | * | 1/1987 | Mazumder ......... G01N 15/0205 356/336 |
| 4,722,347 A | | 2/1988 | Abrams et al. |
| 4,743,107 A | * | 5/1988 | Aizu .................... A61B 3/1225 351/206 |
| 5,309,916 A | * | 5/1994 | Hatschek ............... A61B 5/021 600/485 |
| 6,261,233 B1 | | 7/2001 | Kantorovich |
| 6,322,515 B1 | * | 11/2001 | Goor .................. A61B 5/02007 600/481 |
| 6,447,456 B1 | | 9/2002 | Tsubata |
| 6,716,178 B1 | * | 4/2004 | Kilpatrick ................ A61B 5/01 600/342 |
| 7,125,383 B2 | * | 10/2006 | Hoctor ..................... A61B 8/04 600/438 |
| 7,192,403 B2 | * | 3/2007 | Russell ............. A61B 5/02007 600/485 |
| 7,263,888 B2 | | 9/2007 | Barshinger et al. |
| 7,460,899 B2 | * | 12/2008 | Almen ............... A61B 5/02405 340/575 |
| 7,539,532 B2 | | 5/2009 | Tran |
| 7,641,614 B2 | * | 1/2010 | Asada ................. A61B 5/02225 600/485 |
| 7,674,231 B2 | | 3/2010 | McCombie et al. |
| 8,135,450 B2 | | 3/2012 | Esenaliev et al. |
| 8,672,854 B2 | | 3/2014 | McCombie et al. |
| 8,858,443 B2 | | 10/2014 | Zhang |
| 8,903,141 B2 | | 12/2014 | Heilpern |
| 8,948,832 B2 | * | 2/2015 | Hong .................. A61B 5/02427 600/310 |
| 9,089,306 B2 | | 7/2015 | Harada et al. |
| 10,036,734 B2 | | 1/2018 | Fennell et al. |
| 10,146,981 B2 | | 12/2018 | Sezan et al. |
| 10,528,785 B2 | | 1/2020 | Schmitt et al. |
| 2002/0067359 A1 | | 6/2002 | Brodsky et al. |
| 2002/0115164 A1 | * | 8/2002 | Wang ...................... H05H 3/04 435/173.9 |
| 2004/0015079 A1 | | 1/2004 | Berger et al. |
| 2004/0225217 A1 | | 11/2004 | Voegele et al. |
| 2005/0228276 A1 | | 10/2005 | He et al. |
| 2007/0272020 A1 | | 11/2007 | Schneider et al. |
| 2008/0195003 A1 | | 8/2008 | Sliwa et al. |
| 2010/0056886 A1 | * | 3/2010 | Hurtubise ............ A61B 5/0205 600/324 |
| 2010/0274143 A1 | * | 10/2010 | Kim ...................... A61B 5/022 600/493 |
| 2010/0280390 A1 | | 11/2010 | Hendriks et al. |
| 2011/0178415 A1 | * | 7/2011 | Baldwin ................ A61B 5/021 600/485 |
| 2011/0237940 A1 | | 9/2011 | Raleigh |
| 2012/0059245 A1 | | 3/2012 | Buschmann et al. |
| 2012/0144920 A1 | | 6/2012 | Wong et al. |
| 2013/0018272 A1 | | 1/2013 | Hort |
| 2013/0060141 A1 | | 3/2013 | Sinelnikov |
| 2013/0340838 A1 | | 12/2013 | Rastegar |
| 2014/0058292 A1 | | 2/2014 | Alford et al. |
| 2014/0352440 A1 | | 12/2014 | Fennell et al. |
| 2015/0151142 A1 | | 6/2015 | Tyler et al. |
| 2015/0297181 A1 | | 10/2015 | Akramov et al. |
| 2015/0321026 A1 | | 11/2015 | Branson et al. |
| 2015/0327784 A1 | | 11/2015 | Lading et al. |
| 2016/0049066 A1 | | 2/2016 | Henderson et al. |
| 2016/0143625 A1 | | 5/2016 | Shikata |
| 2017/0231578 A1 | | 8/2017 | Lading et al. |
| 2017/0231598 A1 | | 8/2017 | Baek et al. |

FOREIGN PATENT DOCUMENTS

| | | | | |
|---|---|---|---|---|
| CN | 1925792 | | 3/2007 | |
| CN | 1925792 A | * | 3/2007 | ........... A61B 8/0858 |
| CN | 101578069 | | 11/2009 | |
| CN | 101600392 | | 12/2009 | |
| CN | 101600392 A | * | 12/2009 | ........... A61B 8/4281 |
| CN | 101578069 B | * | 8/2011 | ............. A61B 8/483 |
| CN | 103069844 | | 4/2013 | |
| CN | 203736185 | | 7/2014 | |
| CN | 203736185 U | * | 7/2014 | |
| CN | 104398271 | | 3/2015 | |
| CN | 104398271 A | * | 3/2015 | ......... G01S 7/52042 |
| CN | 104519960 | | 4/2015 | |
| CN | 104699241 | | 6/2015 | |
| CN | 104703548 | | 6/2015 | |
| CN | WO2015127135 | | 8/2015 | |
| CN | 103069844 B | * | 1/2016 | ........... B06B 1/0292 |
| CN | 105407807 | | 3/2016 | |
| CN | 104703548 B | * | 10/2017 | ............. A61B 8/466 |
| CN | 104519960 B | * | 2/2018 | ........... A61B 8/0816 |
| CN | 105407807 B | * | 11/2018 | ........... A61B 8/5223 |
| DE | 112013007011 T5 | | 1/2016 | |
| EP | 2280250 | | 2/2011 | |
| EP | 2289419 A1 | | 3/2011 | |
| EP | 3028639 A1 | | 6/2016 | |
| JP | 2011239972 A | | 12/2011 | |
| JP | 2012061131 A | | 3/2012 | |
| WO | 2005053664 A2 | | 6/2005 | |
| WO | 2015011594 A1 | | 1/2015 | |

OTHER PUBLICATIONS

Abbasi S., "Critical Evaluation and Novel Design of a Non-invasive and Wearable Health Monitoring System," Sep. 2008, 191 Pages.
Almohimeed I., "Development of Wearable Ultrasonic Sensors for Monitoring Muscle Contraction," Aug. 2013, 129 Pages.
U.S. Office Action dated Sep. 12, 2018, in U.S. Appl. No. 15/186,225.
International Search Report and Written Opinion—PCT/US2016/065967—ISA/EPO—dated Mar. 9, 2017.
International Preliminary Report on Patentability—PCT/US2016/065967, The International Bureau of WIPO—Geneva, Switzerland, dated May 23, 2018.
Partial International Search Report—PCT/US2016/065926—ISA/EPO—dated Apr. 20, 2017.
International Search Report and Written Opinion—PCT/US2016/065926—ISA/EPO—dated Aug. 9, 2017.
Invitation to Restrict or Pay Additional Fees—PCT/US2016/065926, The International Bureau of WIPO—Geneva, Switzerland, dated Jan. 26, 2018.
International Preliminary Report on Patentability—PCT/US2016/065926, The International Bureau of WIPO—Geneva, Switzerland, dated Apr. 24, 2018.
U.S. Office Action dated Mar. 27, 2019, in U.S. Appl. No. 15/186,225.
U.S. Office Action dated Jul. 11, 2019, in U.S. Appl. No. 15/186,225.

(56) References Cited

OTHER PUBLICATIONS

U.S. Final Office Action dated Jan. 22, 2020 in U.S. Appl. No. 15/186,225.
U.S. Final Office Action dated Mar. 26, 2020 in U.S. Appl. No. 15/186,225.

* cited by examiner

Acoustic sound speed of the two media: $C1$ and $C2$ $n2 = \dfrac{1}{C2} \quad n1 = \dfrac{1}{C1}$ For the lens to function as a concave lens $C2 > C1 \rightarrow n2 < n1$ $Dx = Dy = K_t \lambda \left[ \dfrac{F}{2a} \right]$ $Dz = 15(1 - 0.01\,\varphi)\,Dx$ $K_t \sim 1$ for small angles of $\varphi < 50$ Degrees
a: radius of annular lens
$\lambda$: Acoustic wave length
F: Focal length

METHODS AND DEVICES FOR CALCULATING BLOOD PRESSURE BASED ON MEASUREMENTS OF ARTERIAL BLOOD FLOW AND ARTERIAL LUMEN

PRIORITY CLAIM

This application claims priority to U.S. Provisional Patent Application No. 62/294,876, filed on Feb. 12, 2016 and entitled "METHODS AND DEVICES FOR CALCULATING BLOOD PRESSURE BASED ON MEASUREMENTS OF ARTERIAL BLOOD FLOW AND ARTERIAL LUMEN," which is hereby incorporated by reference.

TECHNICAL FIELD

This disclosure relates to medical devices, including but not limited to personal medical devices such as wearable medical devices.

DESCRIPTION OF THE RELATED TECHNOLOGY

Devices for measuring cardiovascular properties often suffer from the problem that the measurement itself interferes strongly with the state of the subject, thereby leading to erroneous results. For example, current cuff-based methods for obtaining blood pressure measurements may impart a significant physiological impact. In current cuff-based methods, blood pressure measurements may be obtained by constricting an artery to the extent that blood flow is completely blocked and then slowly releasing the constriction. Constricting the artery affects pulse pressure propagation and pulse pressure shapes, because the elasticity of the artery wall is relaxed. Further, the diastolic pressure is derived from measurements obtained when the transmural pressure (i.e., pressure difference between the outside and the inside of an artery) is close to zero, which implies those measurements are made under conditions that are far from normal.

In addition, traditional methods based on inflatable cuffs and measurements performed in a clinical environment may have strong psychological effects causing changes in a patient's blood pressure. For example, the psychological effects of being in a clinical environment may cause an elevation in the patient's blood pressure. The phenomenon is commonly called "white coat syndrome" or "white coat hypertension." In an additional example, a patient's blood pressure may be elevated during normal daily activities but not in a clinical environment. This phenomenon is commonly called "masked hypertension."

SUMMARY

The systems, methods and devices of the disclosure each have several innovative aspects, no single one of which is solely responsible for the desirable attributes disclosed herein. One innovative aspect of the subject matter described in this disclosure can be implemented in a method of calculating blood pressure. The method may involve performing, by one or more sensors, two or more measurements. The one or more sensors may include one or more ultrasonic sensors, one or more optical sensors or any combination thereof. At least two measurements may correspond to different measurement elevations of a subject's limb. The method may involve determining (for example, by a processor) a blood flow difference based on the two or more measurements. The method may involve determining (for example, by the processor) a hydrostatic pressure difference based on the two or more different measurement elevations of the two or more measurements. The method may involve estimating (for example, by the processor) a blood pressure based on one or more values of blood flow, the hydrostatic pressure difference and the blood flow difference.

In some examples, performing the two or more measurements may involve directing, by the one or more sensors, waves into the limb towards an artery and receiving, by the one or more sensors, one or more reflected waves. The one or more reflected waves may be based, at least in part, on the directed waves. The reflected waves may include scattered waves, specularly reflected waves, or both scattered waves and specularly reflected waves. The method may involve obtaining, by the one or more sensors, the two or more measurements, including the at least two measurements taken at each of two or more different measurement elevations, based on the one or more reflected waves.

In some implementations, the method may involve transmitting, by the one or more sensors, the two or more measurements. For example, the two or more measurements may be transmitted to the processor. Some implementations may involve storing or transmitting, by the processor, an indication or estimation of the blood pressure.

In some implementations, the one or more sensors may include one or more optical sensors of an optical sensor system. The process of directing waves into the limb may involve directing, by the optical sensor system, light waves towards the artery to form a measuring volume having an interference pattern that illuminates at least an interior portion of the artery. The light may include infrared light, visible light, or both infrared light and visible light. A cross-sectional diameter of the measuring volume may be greater than a diameter of the artery. The interference pattern of the measuring volume may have a fringe spacing greater than a diameter of blood cells. In some such examples, the one or more reflected waves may include backscattered light waves.

However, in some implementations the sensor system may include an ultrasonic sensor system. The performing, by the one or more sensors, the two or more measurements may involve directing ultrasonic waves into the limb towards an artery.

According to some examples, determining of the blood flow difference based on the two or more measurements may involve determining (for example, by the processor) values of arterial lumen for each of the measurement elevations and determining a value of blood velocity associated with each of the measurement elevations based, at least in part, on a Doppler shift or a Doppler shift related signal. Some such examples may involve determining (for example, by the processor) a first blood flow associated with a first measurement elevation and a second blood flow associated with a second measurement elevation based on the determined values of blood velocity and the determined values of arterial lumen. The determined values of arterial lumen may, for example, include values of arterial cross-section or arterial volume.

Other innovative aspects of the subject matter described in this disclosure can be implemented in an apparatus that includes a sensor system and a control system configured for communication with the sensor system. In some examples, a mobile device may be, or may include, the apparatus. In some implementations a mobile device may include a portion of the apparatus. In some embodiments, the sensor system may include one or more optical sensors. Alternatively, or additionally, the sensor system may include one or more ultrasonic sensors. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

The control system may be capable of controlling one or more sensors of the sensor system to take two or more measurements. In some examples, at least two of the two or more measurements correspond to different measurement elevations of a subject's limb. According to some implementations, the control system may be capable of determining a blood flow difference based on the or more two or more measurements, of determining a hydrostatic pressure difference based on the two or more different measurement elevations of the two or more measurements and of estimating a blood pressure based on one or more values of blood flow, the hydrostatic pressure difference and the blood flow difference.

In some examples, performing the two or more measurements may involve directing, by the one or more sensors, waves into the limb towards an artery and receiving, by the one or more sensors, one or more reflected waves. The one or more reflected waves may be based, at least in part, on the directed waves. The reflected waves may include scattered waves, specularly reflected waves, or both scattered waves and specularly reflected waves. The control system may be capable of obtaining, via the one or more sensors, the two or more measurements, including the at least two measurements taken at each of two or more different measurement elevations, based on the one or more reflected waves.

In some implementations, the control system may be capable of transmitting, by the one or more sensors, the two or more measurements. In some implementations the control system may be capable of storing or transmitting an indication or estimation of the blood pressure.

In some implementations, the one or more sensors may include one or more optical sensors of an optical sensor system. The process of directing waves into the limb may involve directing, by the optical sensor system, light waves towards the artery to form a measuring volume having an interference pattern that illuminates at least an interior portion of the artery. The light may include infrared light, visible light, or both infrared light and visible light. A cross-sectional diameter of the measuring volume may be greater than a diameter of the artery. The interference pattern of the measuring volume may have a fringe spacing greater than a diameter of blood cells. In some such examples, the one or more reflected waves may include backscattered light waves.

However, in some implementations the sensor system may include an ultrasonic sensor system. The performing, by the one or more sensors, the two or more measurements may involve directing ultrasonic waves into the limb towards an artery.

According to some examples, determining of the blood flow difference based on the two or more measurements may involve determining values of arterial lumen for each of the measurement elevations and determining a value of blood velocity associated with each of the measurement elevations based, at least in part, on a Doppler shift or a Doppler shift related signal. In some such examples the control system may be capable of determining a first blood flow associated with a first measurement elevation and a second blood flow associated with a second measurement elevation based on the determined values of blood velocity and the determined values of arterial lumen. The determined values of arterial lumen may, for example, include values of arterial cross-section or arterial volume.

Some or all of the methods described herein may be performed by one or more devices according to instructions (e.g., software) stored on non-transitory media. Such non-transitory media may include memory devices such as those described herein, including but not limited to random access memory (RAM) devices, read-only memory (ROM) devices, etc. Accordingly, some innovative aspects of the subject matter described in this disclosure can be implemented in a non-transitory medium having software stored thereon.

For example, the software may include instructions for calculating blood pressure. The software may include instructions for performing, by one or more sensors, two or more measurements. The one or more sensors may include one or more ultrasonic sensors, one or more optical sensors or any combination thereof. At least two measurements from the two or more measurements may correspond to different measurement elevations of a subject's limb. The software may include instructions for determining a blood flow difference based on the two or more measurements. The software may include instructions for determining a hydrostatic pressure difference based on the two or more different measurement elevations of the two or more measurements. The software may include instructions for estimating a blood pressure based on one or more values of blood flow, the hydrostatic pressure difference and the blood flow difference.

In some examples, performing the two or more measurements may involve directing, by the one or more sensors, waves into the limb towards an artery and receiving, by the one or more sensors, one or more reflected waves. The one or more reflected waves may be based, at least in part, on the directed waves. The reflected waves may include scattered waves, specularly reflected waves, or both scattered waves and specularly reflected waves. The software may include instructions for obtaining, by the one or more sensors, the two or more measurements, including the at least two measurements taken at each of two or more different measurement elevations, based on the one or more reflected waves.

In some implementations, the software may include instructions for transmitting, by the one or more sensors, the two or more measurements. For example, the two or more measurements may be transmitted to a processor. In some implementations, the software may include instructions for storing or transmitting an indication or estimation of the blood pressure.

In some implementations, the one or more sensors may include one or more optical sensors of an optical sensor system. The process of directing waves into the limb may involve directing, by the optical sensor system, light waves towards the artery to form a measuring volume having an interference pattern that illuminates at least an interior portion of the artery. The light may include infrared light, visible light, or both infrared light and visible light. A cross-sectional diameter of the measuring volume may be greater than a diameter of the artery. The interference pattern of the measuring volume may have a fringe spacing greater than a diameter of blood cells. In some such examples, the one or more reflected waves may include backscattered light waves.

However, in some implementations the sensor system may include an ultrasonic sensor system. The performing, by the one or more sensors, the two or more measurements may involve directing ultrasonic waves into the limb towards an artery.

According to some examples, the determining of the blood flow difference based on the two or more measurements may involve determining values of arterial lumen for each of the measurement elevations and determining a value of blood velocity associated with each of the measurement elevations based, at least in part, on a Doppler shift or a Doppler shift related signal. In some such examples, the software may include instructions for determining a first blood flow associated with a first measurement elevation and a second blood flow associated with a second measurement elevation based on the determined values of blood velocity and the determined values of arterial lumen. The determined values of arterial lumen may, for example, include values of arterial cross-section or arterial volume.

Other innovative aspects of the subject matter described in this disclosure can be implemented in an apparatus, such as an ultrasound cardiovascular measuring device. The apparatus may include an ultrasonic sensor system and a control system configured for communication with the ultrasonic sensor system. In some examples, a mobile device may be, or may include, the apparatus. In some implementations a mobile device may include a portion of the apparatus. According to some examples, the apparatus may be configured to be wearable. In some implementations, the apparatus may be integrated into a fixture and configured to contact a subject when the subject uses the fixture.

In some embodiments, the ultrasonic sensor system may include an ultrasound transmitter layer configured to generate ultrasonic plane waves. The ultrasonic sensor system may include a focusing layer comprising one or more lenses. The one or more lenses may include a cylindrical lens, a spherical lens, a concave lens, a convex lens, a zone lens and/or a zone plate. One or more of the lenses may be configured to focus the ultrasonic plane waves into a beam of ultrasound across an arterial longitudinal axis. The ultrasonic sensor system may include an ultrasound receiver layer comprising one or more receiver elements configured to generate output signals corresponding to detected ultrasonic reflections. In some examples, one or more of the receiver elements may be positioned in the ultrasound receiver layer to detect the ultrasonic reflections redirected through the one or more lenses in the focusing layer. In some examples, two or more of the receiver elements may be configured as a receiver element array.

The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system may be capable of processing the output signals to calculate values corresponding to one or more cardiovascular properties. The one or more cardiovascular properties may, for example, include blood pressure. In some examples, the control system may be capable of calculating a cross-sectional area of a blood vessel based, at least in part, on the output signals from the ultrasound receiver layer. According to some such examples, the control system may be capable of performing multiple calculations of the cross-sectional area of the blood vessel based, at least in part, on output signals received from the ultrasound receiver layer at multiple times. In some such examples, the control system may be capable of determining instances of heart beats and wherein the multiple times correspond to time intervals between the instances of heart beats.

According to some examples, the control system may be capable of selectively sampling the output signals of a subset of the receiver elements. In some such examples, the control system may be capable of selectively sampling the output signals of a subset of the receiver elements of a receiver element array.

According to some embodiments, the focusing layer may include acoustic matching material in which the one or more lenses are embedded. Alternatively, or additionally, the focusing layer may include at least a first lens and a second lens. The first lens may be configured to focus the ultrasonic plane waves at a first focal depth and the second lens may be configured to focus the ultrasonic plane waves at a second focal depth. Alternatively, or additionally, the focusing layer may include at least two lenses that are spaced apart along the arterial longitudinal axis. According to some such examples, the control system may be capable of calculating a pulse transit time or a pulse wave velocity of an arterial pressure pulse propagating along the arterial longitudinal axis.

In some examples, the focusing layer further may include at least one lens that is oriented at an angle relative to an outer surface of the ultrasonic sensor system. According to some such examples, the control system may be capable of calculating a blood flow based, at least in part, on a Doppler shift or Doppler shift related signal indicated by the output signals from the ultrasound receiver layer.

According to some implementations, the ultrasound transmitter layer may include a first polyvinylidene fluoride (PVDF) transducer layer and the ultrasound receiver layer may include a second PVDF transducer layer and a thin film transistor (TFT) layer. In some such implementations, each of the one or more ultrasound receiver arrays may include a plurality of receiver elements coupled to the second PVDF transducer layer.

In some examples, the ultrasonic sensor system may be integrated within a button or display of a mobile computing device. In some such examples, the control system may be a part of a control system of the mobile computing device.

BRIEF DESCRIPTION OF THE DRAWINGS

The accompanying drawings, which are incorporated herein and constitute part of this specification, illustrate exemplary embodiments of the claims, and together with the general description given above and the detailed description given below, serve to explain the features of the claims.

DETAILED DESCRIPTION

Figure 1A:
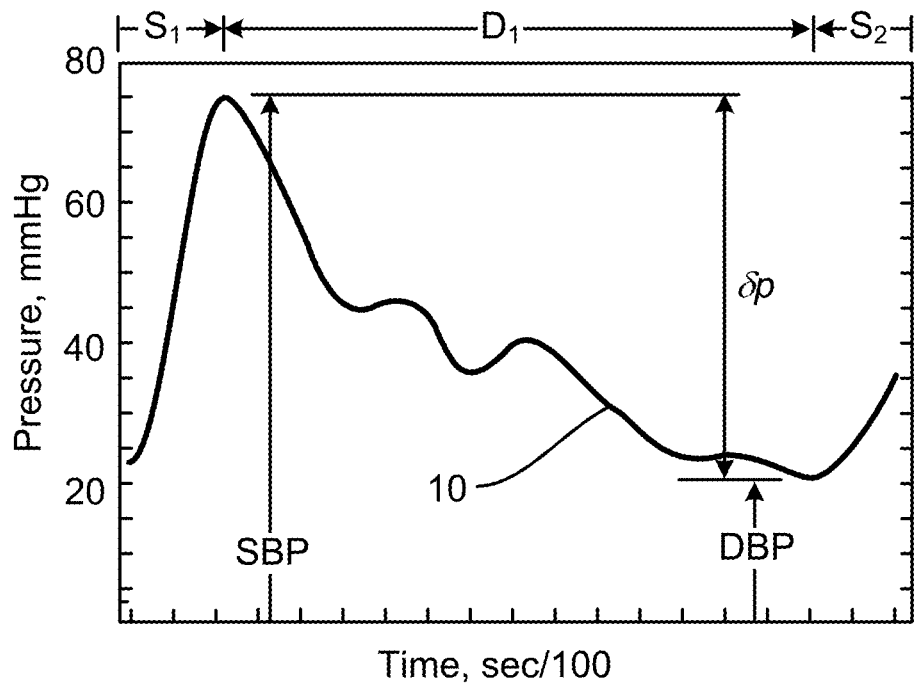
FIG. 1A is a graph of blood pressure versus time for an artery during a full phase of a pulse and the start of a subsequent pulse.

Various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the claims.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a sensor system. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, global navigation satellite system (GNSS) receivers/navigators, cameras, digital media players (such as MP3 players), camcorders, game consoles, wrist watches, electronic reading devices (e.g., e-readers), mobile health devices, and a variety of EMS devices. Thus, the teachings are not intended to be limited to the implementations depicted solely in the Figures, but instead have wide applicability as will be readily apparent to one having ordinary skill in the art.

In addition to the above-described issues regarding previous method and devices for measuring cardiovascular properties, some medical professionals have observed that blood pressure often exhibits considerable variability over time. Thus, identifying diurnal or other temporal variations in blood pressure may be important for proper diagnosis of various cardiovascular issues, including hypertension. It has also been shown that performing ambulatory blood pressure measurements may be beneficial for improved diagnosis by facilitating measurements over longer time periods and avoiding the psychological effects typical in clinical environments.

Some implementations disclosed herein involve improved methods of calculating blood pressure. In some implementations, the method may involve performing, by one or more sensors, two or more measurements. The two or more measurements may include at least two measurements taken at each of two or more different measurement elevations of a subject's limb. In some examples, the two or more measurements may include a measurement of blood flow and a measurement of arterial cross-section. The method may involve determining (e.g., by a processor) a blood flow difference based on the two or more measurements, determining a hydrostatic pressure difference based on the two or more different elevations of the two or more measurements and estimating a blood pressure based on one or more values of blood flow, the hydrostatic pressure difference and the blood flow difference.

Particular implementations of the subject matter described in this disclosure can be implemented to realize one or more of the following potential advantages. In some examples, methods of calculating blood pressure may be implemented via a device that does not interfere with the normal flow of blood through an arterial system or, at the least, does not perturb an artery being measured. Such methods and devices may be capable of identifying diurnal or other temporal variations in blood pressure. Such methods and devices may be capable of facilitating blood pressure calculations over relatively longer time periods and of avoiding the psychological effects typical in clinical environments. Accordingly, blood pressure estimation provided by such methods and devices may facilitate improved diagnoses of various cardiovascular issues, including hypertension.

As used herein, the term "pulse pressure" refers to the difference between systolic pressure and diastolic pressure caused by the beating of the heart. This value is generally not affected by local changes in the hydrostatic pressure in the peripheral regions of the body of the subject.

As used herein, the term "transmural pressure" refers to the pressure difference between the pressure inside an artery and directly outside the artery at a specific location in a specific artery. The transmural pressure depends on the hydrostatic pressure due to the height of the specific location. For example, if a measuring device is attached to the wrist of a subject, then moving the wrist up and down will cause significant changes in the transmural pressure measured at the measuring location whereas the pulse pressure will be relatively unaffected by the slow up and down motion of the wrist. In addition, without an externally applied counter pressure (e.g., inward pressure from an inflatable cuff or other external device) the transmural pressure may be presumed to be approximately equal to the absolute arterial pressure.

The term "absolute arterial pressure" is used herein to define the actual pressure in an artery at a specific location and at a particular time. In most cases the absolute arterial pressure will be very close to the transmural pressure at the same location if no significant external pressure is applied to the artery (i.e., only atmospheric pressure is applied). The terms "absolute arterial pressure" and "transmural pressure" are used herein interchangeably.

The term "blood pressure" is used herein as a general term to refer to a pressure in the arterial system of the subject. For the sake of this specification, the transmural pressure, the pulse pressure, and the absolute arterial pressure are all referred to as "blood pressures." For example, devices that measure the transmural pressure at a specific location and devices that measure the pulse pressure may be used to measure blood pressure.

As used herein, the expression "non-interfering" refers to a device that does not interfere with the normal flow of blood through the arterial system or at least does not perturb an artery being measured.

The term "optical blood pressure calculating device" is used herein to refer to a physical apparatus that is configured to be placed in optical contact with the skin of a subject for taking measurements of a blood pressure, such as a device that can be worn by the subject or a mobile device that can be positioned on or near the subject. In contrast, the term "optical sensor" generally refers to a device that is configured to be placed in optical contact with the skin of a subject, such as a sensor that is wearable or can be placed on a finger, wrist or other body part or a sensor on a fixture, and that responds to a light stimulus and transmits a resulting output (as for measurement or operating a control). The term "optical contact" is used herein to mean that the emitted light from the optical blood pressure calculating device is able to enter to skin of the subject and interact with tissues below the skin, and backscattered light is able to enter the optical blood pressure calculating device from the skin of the subject. Thus, having the optical blood pressure calculating device in "optical contact" does not necessarily require the optical blood pressure calculating device to be placed in physical contact with a subject's skin. For example, a transparent structure (e.g., as a glass cover), intermediate substance (e.g., a transparent gel), or an air gap may be interposed between the optical calculating device and the skin of the subject.

The term "ultrasound measuring device" is used herein to refer to a sensor device including one or more ultrasound sensors that is configured to be placed in contact with the skin of a subject for taking measurements of a biometric. A "wearable ultrasound measuring device" may be a structure that can be worn by the subject (e.g., a patch, clothing, sports equipment, etc.) or a structure on a fixture (e.g., furniture, sports equipment, automobile fixtures, etc.) configured to position the ultrasound sensor against the subject. In contrast, the term "wearable ultrasound sensor" generally refers to a device that is configured to be placed in contact with the skin of a subject, such as a sensor that is wearable on a finger, wrist or other limb, and that responds to an ultrasonic stimulus and transmits a resulting output (as for measurement or operating a control). The contact may involve an intermediate matching layer to ensure sufficient acoustic coupling.

The term "limb" is used herein to refer to a finger, wrist, forearm, ankle, leg, or other body part suitable for taking measurements of blood pressure.

The term "lumen" may be used herein to mean an inside space of a tubular structure. For example, the term "lumen" may be used herein to refer to the space inside an artery or a vein through which blood flows. Lumen and arterial cross-sectional area are in general proportional because diameter variations dominate over length variations with variations of the blood pressure.

Figure 1B:
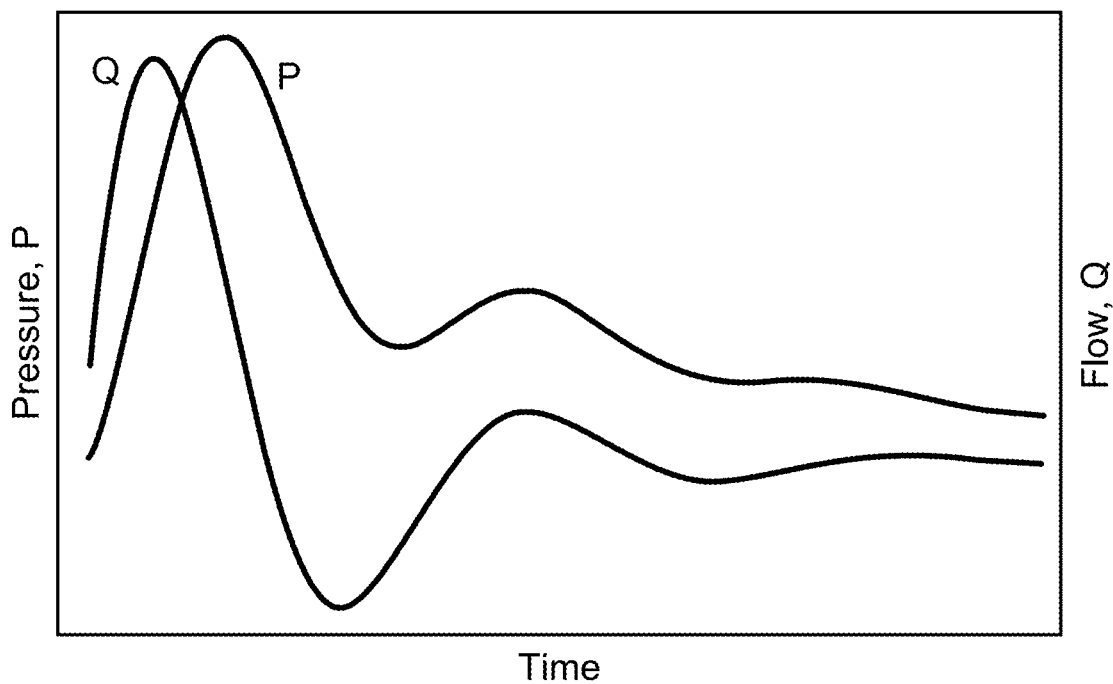
FIG. 1B shows graphs of both pressure and flow pulses.

FIG. 1A is a graph of blood pressure versus time for an artery during a full phase of a pulse and the start of a subsequent pulse. In particular, FIG. 1A illustrates a blood pressure 10 showing typical changes in pressure (i.e., the vertical axis, measured in mmHg) that occur over time (i.e., the horizontal axis, measured in sec/100) during a pulse cycle (i.e., one contraction cycle of the heart). Blood flow versus time over full phase of a pulse will exhibit the same general features as the pressure pulse although the specific shape is slightly different as shown in FIG. 1B.

Pressure pulses occur after each contraction of the left heart ventricle and are considered as having two parts. A first part $S_1$ of pressure pulses, referred to as the systolic phase, reflects the immediate rise and peaking of the pressure as a consequence of the ejection from the heart. The second part $D_1$ of pressure pulses, referred to as the diastolic phase, reflects the fall of the pressure after the systolic phase. The diastolic phase is generally characterized by an exponentially decaying pressure. The exponential decay asymptotically approaches a pressure that normally is considerably lower than the diastolic pressure, but is redirected before doing so upon the occurrence of the subsequent pulse, which starts the next pulse's systolic phase $S_2$. The exponential decay may be caused by the arterial system being connected with the veins through capillary network with a high fluid-flow resistivity and the veins being much more elastic than the arteries. The venous system essentially behaves like a capacitor, which has a capacitance much larger than that of the arterial system.

Various embodiments include a non-interfering blood pressure calculating device and method of calculating blood pressure based upon measurements of an arterial lumen and blood flow. The method may involve estimating blood pressure based on measurements taken at two or more elevations of a subject's limb. The non-interfering blood pressure calculating device may include one or more sensors. In some embodiments, the one or more sensors may include one or more optical sensors. Alternatively, or additionally, some implementations may include one or more ultrasonic sensors.

Figure 1C:
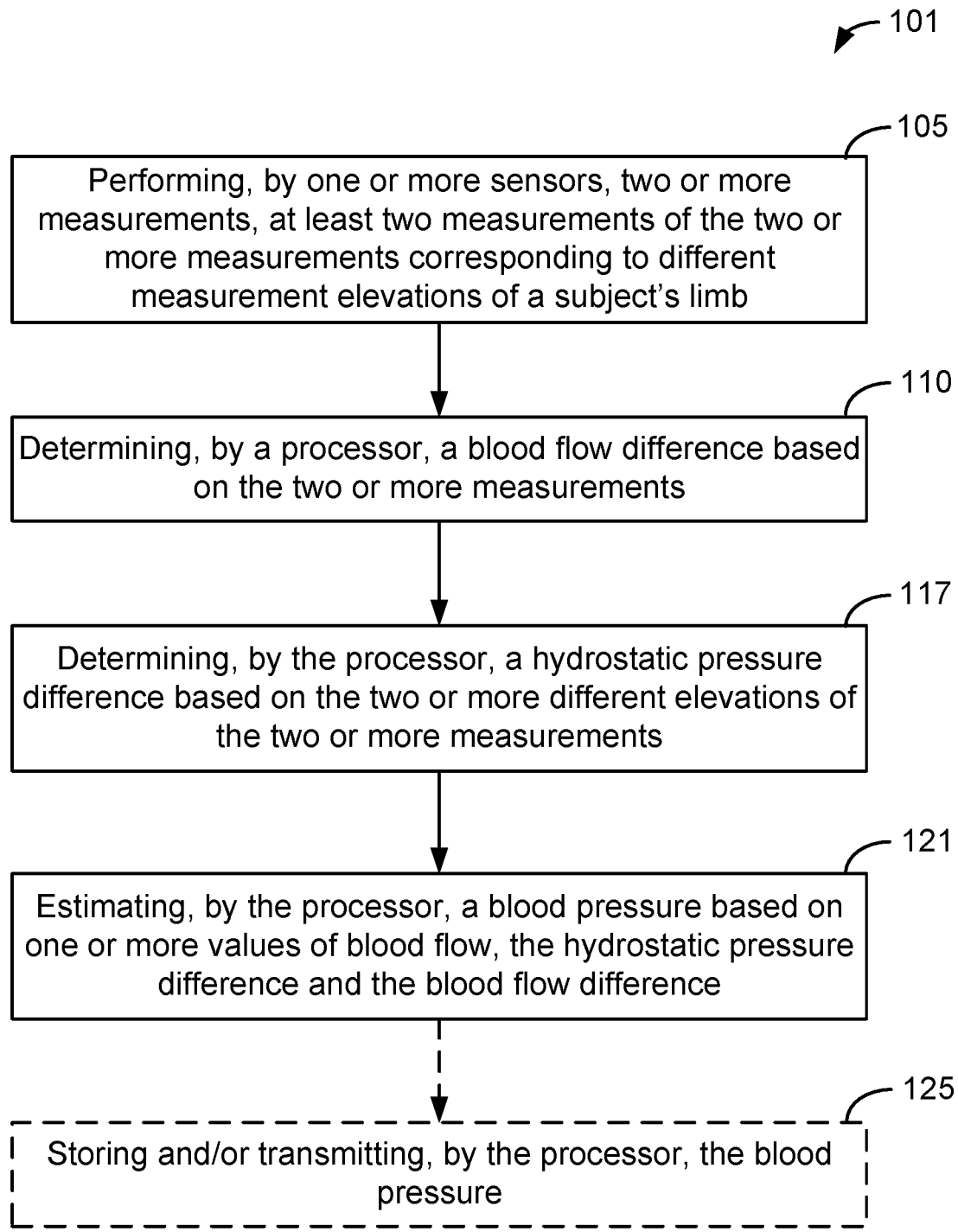
FIG. 1C is a flow diagram that outlines one example of a method for estimating blood pressure.

FIG. 1C is a flow diagram that outlines one example of a method for estimating blood pressure. The blocks of method 101, like other methods described herein, are not necessarily performed in the order indicated. Moreover, such methods may include more or fewer blocks than shown and/or described. Although some blocks of method 101 are described as being performed by a single processor, in alternative implementations more than one processor may be involved in performing these operations. For example, more than one processor of a control system may be involved in performing these operations.

Figure 1D:
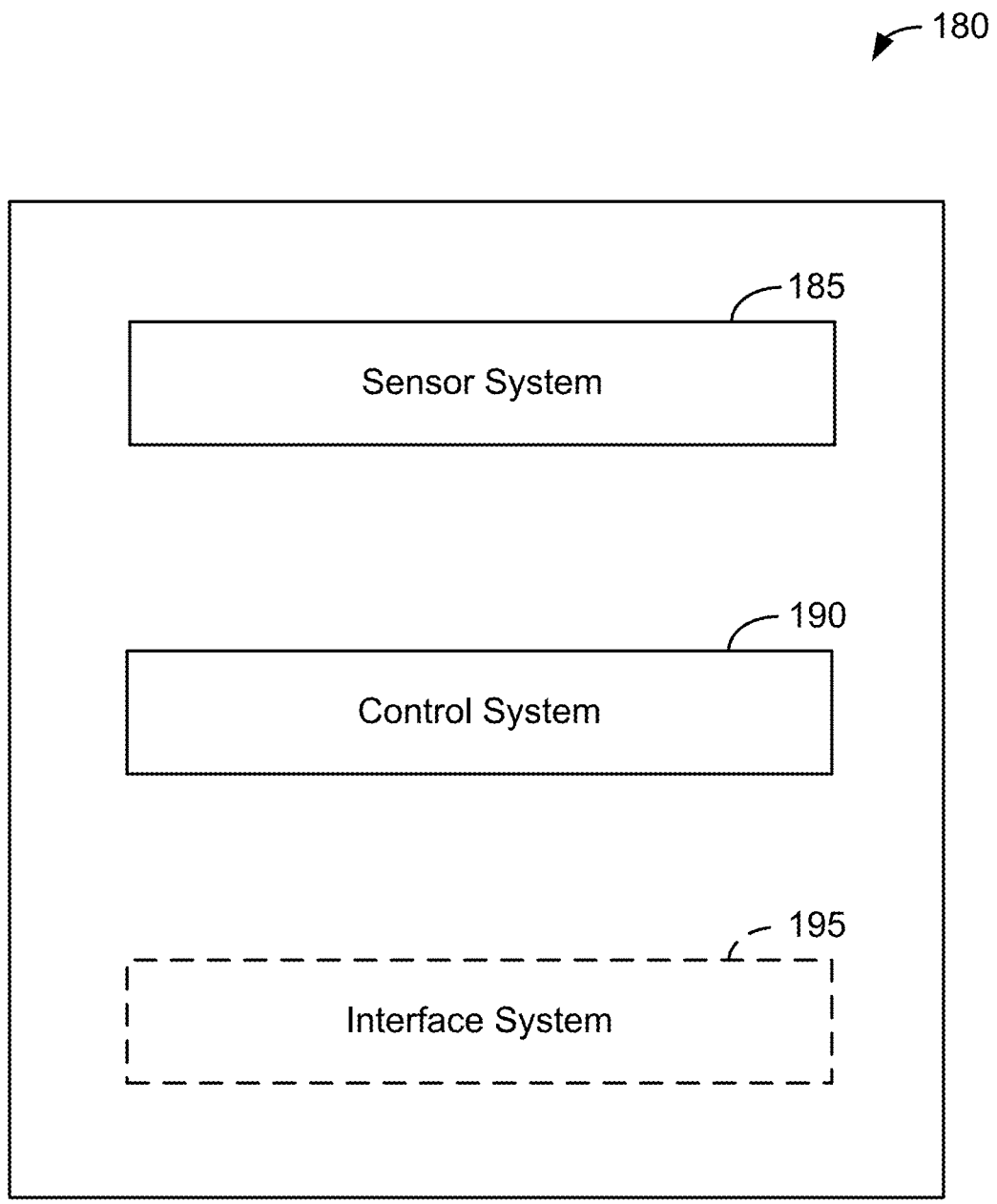
FIG. 1D is a block diagram that shows examples of components of apparatus in which some aspects of the present disclosure may be implemented.
Figure 6A:
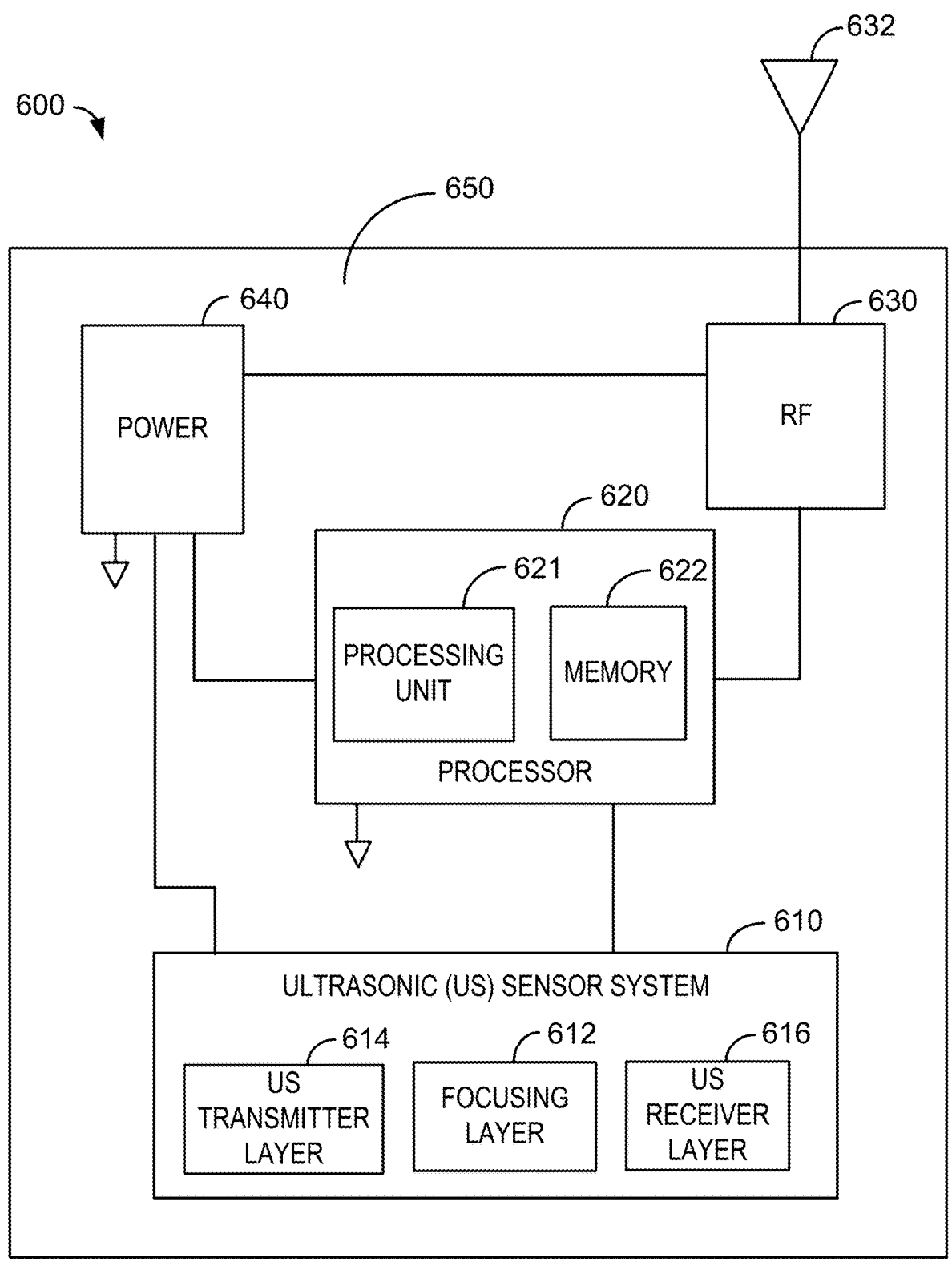
FIG. 6A illustrates example components of a wearable ultrasound measuring device including a wearable ultrasound sensor according to various embodiments.

In one example, the method may be implemented by the apparatus 180 that is shown in FIG. 1D. The blocks of method 101 may, for example, be performed (at least in part) by a control system such as the control system 190 that is shown in FIG. 1D. However, method 101 also may be performed by other devices or systems, such as the non-interfering optical blood pressure calculating device 200 shown in FIG. 2A and described below. According to some implementations, method 101 may be performed by the wearable ultrasound measuring device that is shown in FIG. 6A and described below. In some examples, method 101 may be implemented, at least in part, by another device, such as the mobile computing device shown in FIG. 7A and described below. According to some examples, method 101 may be implemented, at least in part, according to software stored on one or more non-transitory media.

Figure 3A:
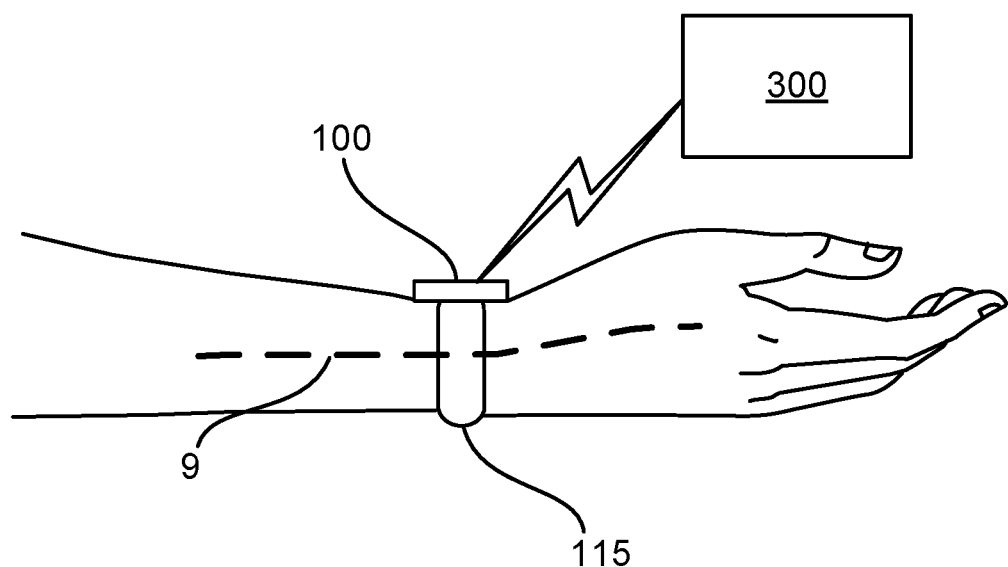
FIG. 3A illustrates a non-interfering blood pressure calculating device for estimating blood pressure that is worn on a limb of a subject according to some embodiments.
Figure 3B:
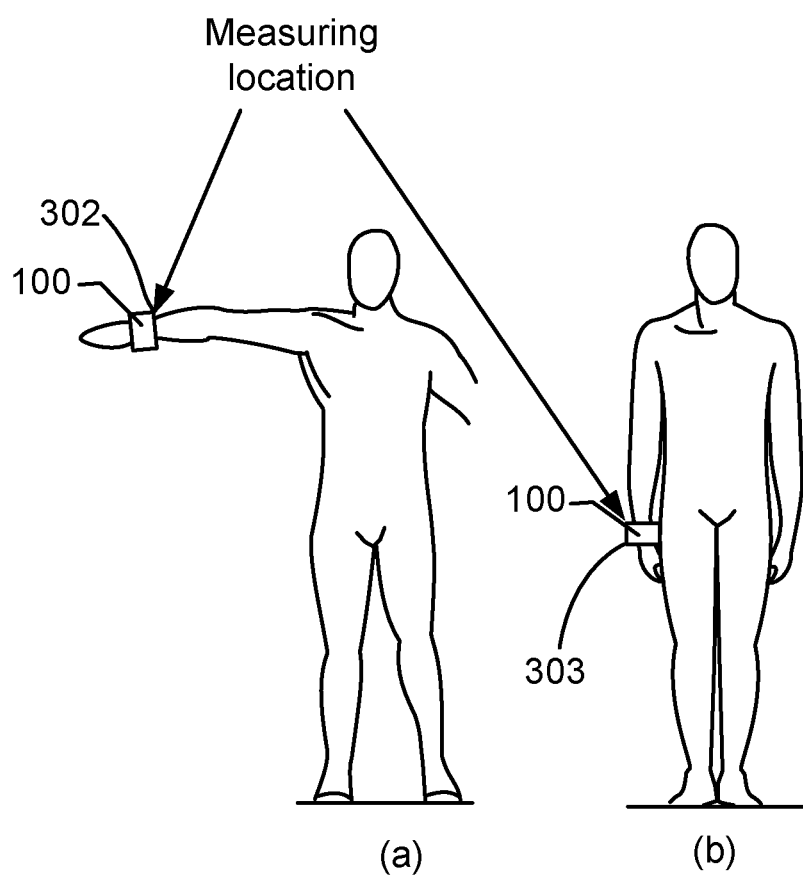
FIG. 3B illustrates the non-interfering blood pressure calculating device of FIG. 3A in two different measurement elevations as may be used to determine blood pressure according to some embodiments.

In the example shown in FIG. 1C, block 105 involves performing, by one or more sensors, two or more measurements. In this example, at least two measurements of the two or more measurements correspond to different measurement elevations of a subject's limb. In some examples, the two or more measurements may include a measurement of blood flow and a measurement of arterial cross-section. For example, block 105 may involve performing, by one or more sensors, the two or more measurements and transmitting the two or more measurements to a control system of a device that obtained the measurements. Accordingly, block 105 may involve receiving, by the control system, the two or more measurements. Alternatively, or additionally, block 105 may involve performing the two or more measurements and transmitting the two or more measurements to another device. Various examples of obtaining these measurements are described below. FIGS. 3A and 3B show examples of obtaining such measurements at two different elevations of a subject's limb. Although the discussion of FIGS. 3A and 3B primarily involves obtaining such measurements using one or more optical sensors, other implementations involve obtaining such measurements using one or more ultrasonic sensors. Some ultrasonic-based examples are provided below. Accordingly, the one or more sensors may include one or more ultrasonic sensors, one or more optical sensors or any combination thereof.

In some examples, obtaining such measurements may involve directing, by the one or more sensors, waves into the limb towards an artery. For implementations that include an ultrasonic sensor system, directing waves into the limb may involve directing ultrasonic waves towards the artery. The process may involve receiving, by the one or more sensors, one or more reflected waves that are based, at least in part, on the directed waves. The reflected waves may include scattered waves, specularly reflected waves, or both scattered waves and specularly reflected waves. The method may involve obtaining, by the one or more sensors, two or more measurements, including at least two measurements taken at each of two or more different measurement elevations, based on the one or more reflected waves. The method may involve transmitting, by the one or more sensors, the two or more measurements to a control system (e.g., to the processor referenced in block 110). In some implementations, the method may involve transmitting, by the one or more sensors, the two or more measurements to a second device. According to some such implementations, the second device may include the processor referenced in block 110. Some methods may involve taking multiple measurements at each elevation of the limb. Some such method may involve taking measurements during more than one pulse at each elevation of the limb.

According to some such examples, the one or more sensors may include one or more optical sensors of an optical sensor system. In some examples, directing waves into the limb may involve directing, by the optical sensor system, light waves towards the artery. The light may include infrared light, visible light or both infrared light and visible light. Some implementations may involve directing light waves towards the artery to form a measuring volume having an interference pattern that illuminates the artery. In some implementations, illuminating the artery involves illuminating at least an interior portion of the artery in which blood can flow. One or more exterior portions of the artery also may be illuminated. According to some implementations, a cross-sectional diameter of the measuring volume may be greater than a diameter of the artery. According to some examples, the interference pattern of the measuring volume may have a fringe spacing greater than a typical diameter of blood cells. In some examples, the reflected waves may include backscattered radiation, such as backscattered light waves. Basing measurements upon backscattered light is potentially advantageous. The power of backscattered light is less dependent on the orientation and the size of blood cells than the power of forward-scattered light. Moreover, backscattered light can be more easily accessible despite the fact that forward-scattered light is generally stronger than backscattered light.

In this implementation, block 110 involves determining, by a processor, a blood flow difference based on the at least two measurements. In some examples, block 110 may involve determining, by the processor, values of arterial lumen for each of the at least two measurement elevations. The determined values of arterial lumen associated with the at least two measurement elevations may include values of arterial cross-section or values of arterial volume. In some ultrasonic-based implementations block 110 may involve determining values of arterial lumen according to reflections detected from arterial walls. In some optical-based implementations block 110 may involve determining values of arterial lumen based on an integral of a frequency-shifted part of the at least two measurements. In some optical-based implementations, block 110 may involve determining values of arterial lumen based on Optical Coherence Tomography.

According to some implementations, block 110 may involve determining, by the processor, a value of blood velocity associated with each of the at least two different measurement elevations. The values of blood velocity may be based on a frequency shift corresponding to the frequency-shifted part of the at least two measurement elevations. In some examples, the values of blood velocity may be based on a Doppler shift or a Doppler shift related signal determined at each of the at least two measurement elevations. One example of a "Doppler shift related signal" in the context of ultrasound implementations may be the output of a time shift estimator on received radio frequency signals related to the location of the artery. For example, some ultrasound implementations may involve transmitting ultrasound pulses and calculating the tissue depths from which the ultrasound pulses are reflected. In some such examples, the depth of an artery may be determined in this way. The ultrasound signal at this depth may truly be Doppler shifted according to the normal meaning of the term. However, frequency shifts caused by attenuation, dispersion, scattering, non-linearity from propagation through numerous layers of tissue may be greater than the Doppler shift caused by moving blood. Therefore, such Doppler shift measurements may not be accurate enough for measuring blood flow in the ultrasound context. However, the ultrasound signal may also undergo a phase or time shift because of the time-changing reflection pattern caused by blood flow. This time shift can be shown to be proportional to the velocity and to have the same form as the Doppler equation. Accordingly, this is one example of what is referred to herein as a "Doppler shift related signal." In some such implementations, block 110 may involve determining, by the processor, a first blood flow associated with a first measurement elevation and a second blood flow associated with a second measurement elevation. The first and second blood flow may be based on the determined values of blood velocity and the determined values of arterial lumen.

Figure 4A:
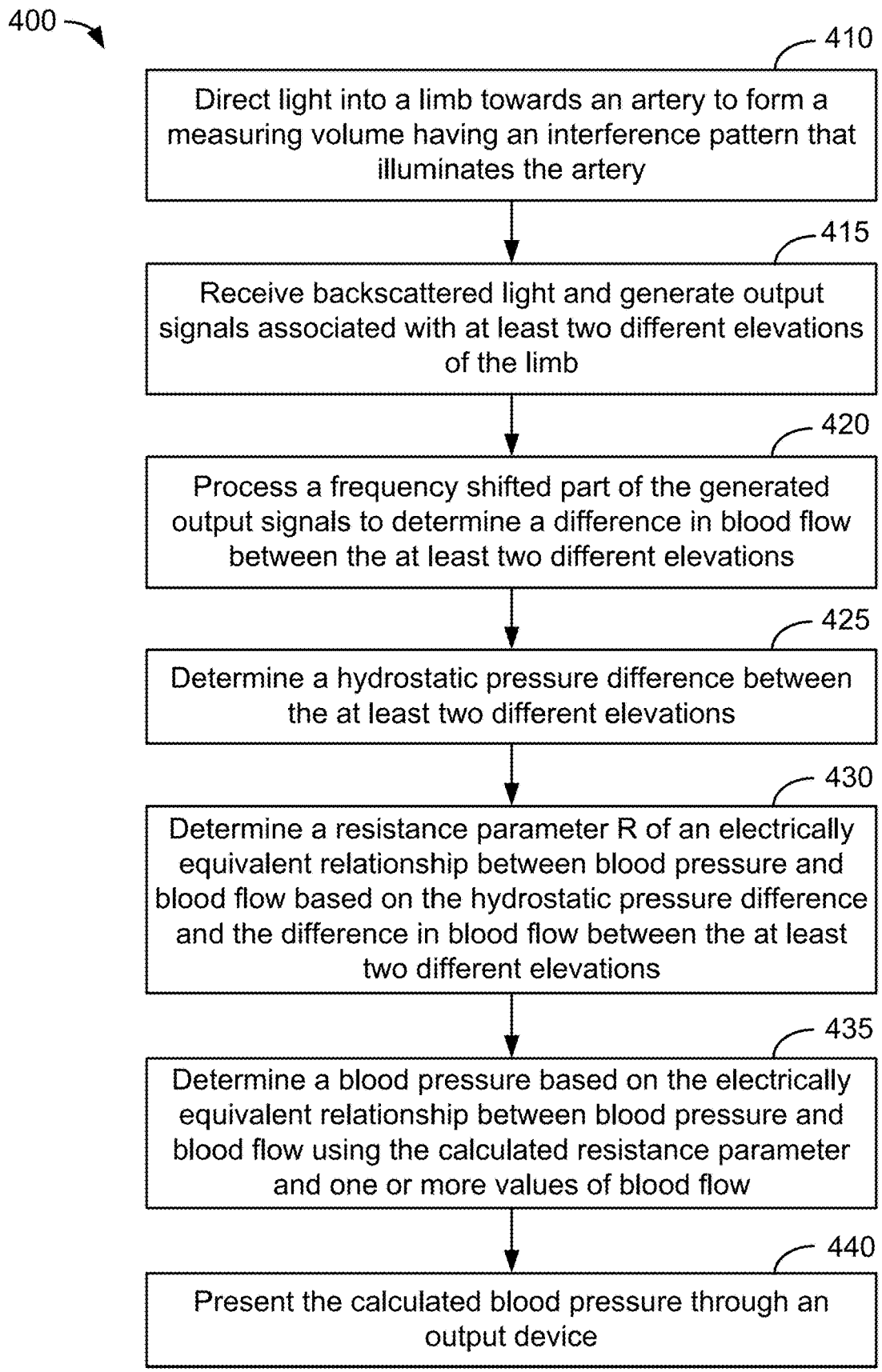
FIG. 4A is a flow diagram that outlines one example of a method for calculating blood pressure according to a first embodiment.

In the example shown in FIG. 1C, block 117 involves determining, by the processor, a hydrostatic pressure difference based on the two or more different elevations of the at least two measurements. The elevations may, for example, be based on measurements of an elevation sensor, such as the elevation sensor 220 shown in FIG. 2A and described below. The description below corresponding with block 425 of FIG. 4A provides an example of determining the hydrostatic pressure difference based on the two or more different elevations.

Figure 5A:
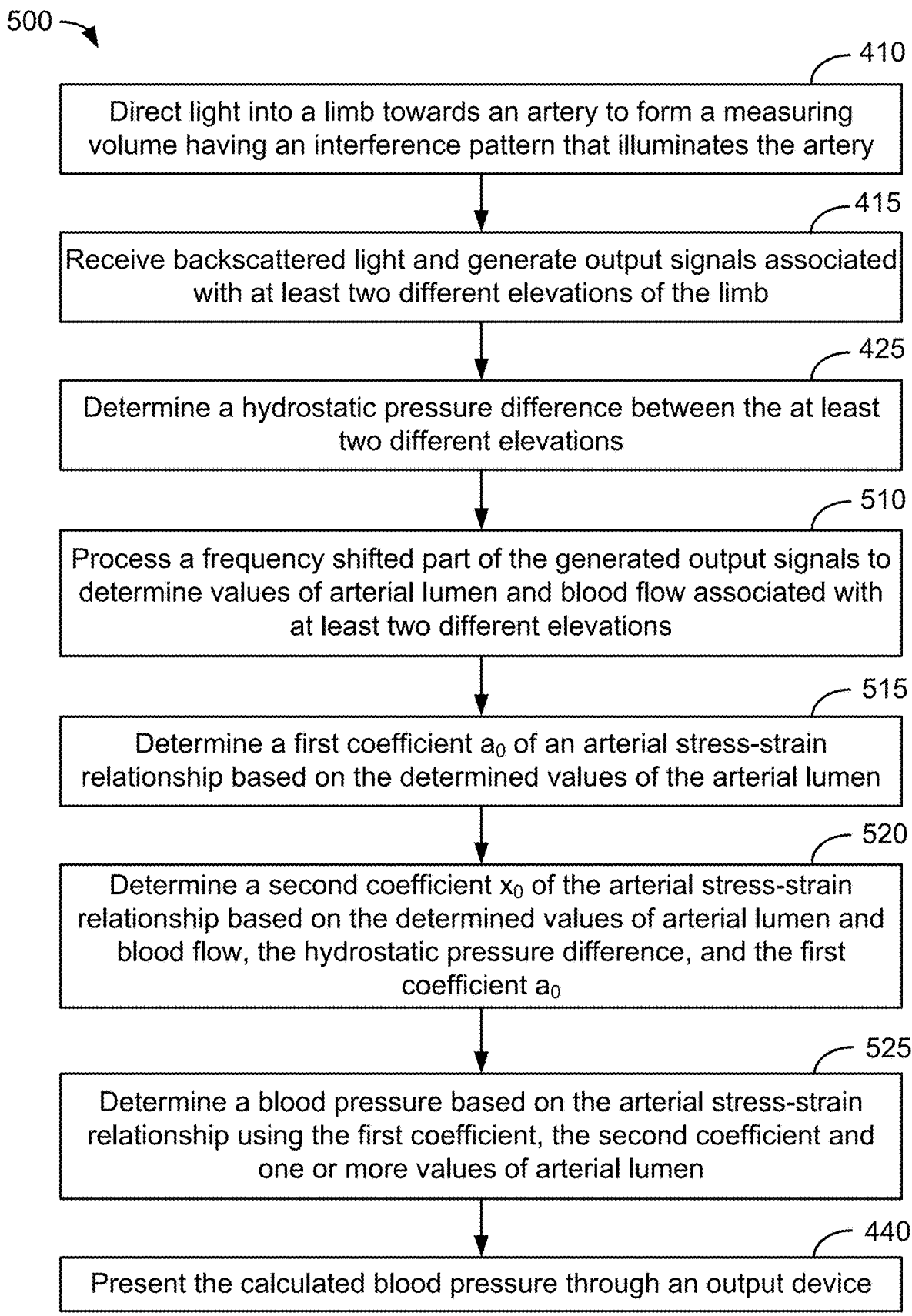
FIG. 5A is a flow diagram that outlines one example of a method for calculating blood pressure based on measurements of flow and lumen according to a second embodiment.

According to this example, block 121 involves estimating, by the processor, a blood pressure. In this implementation, block 120 involves estimating the blood pressure based on one or more values of blood flow, the hydrostatic pressure difference and/or the blood flow difference. The description below corresponding with blocks 430 and 435 of FIG. 4A provides an example of determining the blood pressure. The description below corresponding with block 525 of FIG. 5A provides another example of determining the blood pressure, based on measurements and calculations that are described below with reference to blocks 410-520 of FIG. 5A.

In this example, optional block 125 involves storing an indication or estimation of the blood pressure, transmitting an indication or estimation of the blood pressure, or both storing and transmitting an indication or estimation of the blood pressure. For example, optional block 125 may involve storing one or more values corresponding with an indication or estimation of the blood pressure in a memory of, or in communication with, the control system 190 of the apparatus 180 that is shown in FIG. 1D, in a memory of the non-interfering optical blood pressure calculating device 200 shown in FIG. 2A or a memory of the wearable ultrasound measuring device that is shown in FIG. 6A. Alternatively, or additionally, optional block 125 may involve transmitting one or more values corresponding with an indication or estimation of the blood pressure via the interface system 195 of the apparatus 180 that is shown in FIG. 1D, via the radio frequency (RF) processor 150 and the antenna 152 of the non-interfering optical blood pressure calculating device 200 shown in FIG. 2A or via the radio frequency (RF) module 630 and the antenna 632 of the wearable ultrasound measuring device that is shown in FIG. 6A.

FIG. 1D is a block diagram that shows examples of components of apparatus in which some aspects of the present disclosure may be implemented. As with other implementations disclosed herein, the numbers of elements and types of elements shown in FIG. 1D are merely shown by way of example. Other implementations may have more, fewer or different elements. In the implementation shown in FIG. 1D, the apparatus 180 includes a sensor system 185 and a control system 190. In some implementations, the sensor system 185 may include one or more optical sensors. Alternatively, or additionally, in some examples the sensor system 185 may include one or more ultrasonic sensors. Various examples of optical sensors and ultrasonic sensors are disclosed herein.

The control system 190 may include at least one of a general purpose single- or multi-chip processor, a digital signal processor (DSP), an application specific integrated circuit (ASIC), a field programmable gate array (FPGA) or other programmable logic device, discrete gate or transistor logic, or discrete hardware components. The control system 190 may be capable of performing some or all of the methods described herein. In some examples, the control system 190 may be capable of performing method 101. According to some examples, the control system 190 may be capable of performing method 400, which is described below with reference to FIG. 4A. In some examples, the control system 190 may be capable of performing method 500, which is described below with reference to FIG. 5A. In some examples, the control system 190 may be capable of performing method 1800, which is described below with reference to FIG. 18. In some implementations, the control system 190 may be capable of controlling one or more components of the apparatus 180. For example, the control system 190 may be capable of controlling the sensor system 185. The control system 190 may be capable of controlling the interface system 195.

In some implementations, the control system 190 may be capable of controlling the apparatus 180 according to instructions (e.g., software) stored on one or more non-transitory media. Such non-transitory media may include one or more memory devices of the apparatus 180, which may include one or more random access memory (RAM) devices, one or more read-only memory (ROM) devices, etc. In some implementations, the control system 190 may include one or more of such memory devices. Accordingly, at least some aspects of the subject matter disclosed herein may be implemented via one or more non-transitory media having software stored thereon.

In the example shown in FIG. 1D, the apparatus 180 includes an optional interface system 195. The interface system 195 may, for example, include a wireless interface system. In some implementations, the interface system 195 may include a network interface, an interface between the control system 190 and a memory system and/or an external device interface (e.g., a port). According to some examples, the interface system 195 may include a user interface. In some implementations, the apparatus 180 may be capable of wireless communication with a second device via the interface system 195. Some examples are described below.

Some implementations involving optical sensors will now be described with reference to FIG. 2A et seq. According to some such implementations, the non-interfering optical blood pressure calculating device may include a Doppler velocimetry sensor configured to enable measuring the velocity of blood flow as well as the volume of blood in an artery positioned below the sensor. Blood flow velocity may be measured by determining a characteristic differential Doppler shift resulting from light that is backscattered from blood cells interacting in the volume of the artery with interference fringes formed by the interference of two beams from the same light source, which may be a laser. The volume of blood flowing in the artery, which may yield a measure of the arterial lumen, may be determined based on an intensity of backscattered light. Volumetric blood flow may be determined as a product of the blood flow velocity times the arterial lumen incorporating effects of the velocity profile across the artery, and thus calculated based on the intensity of Doppler shifted light backscattered from blood cells in the illuminated artery. Blood pressure may then be determined based on the distension of the artery based on the arterial lumen and blood flow measured at different elevations of the limb on which measurements are taken using a relationship between blood flow and blood pressure.

Figure 2A:
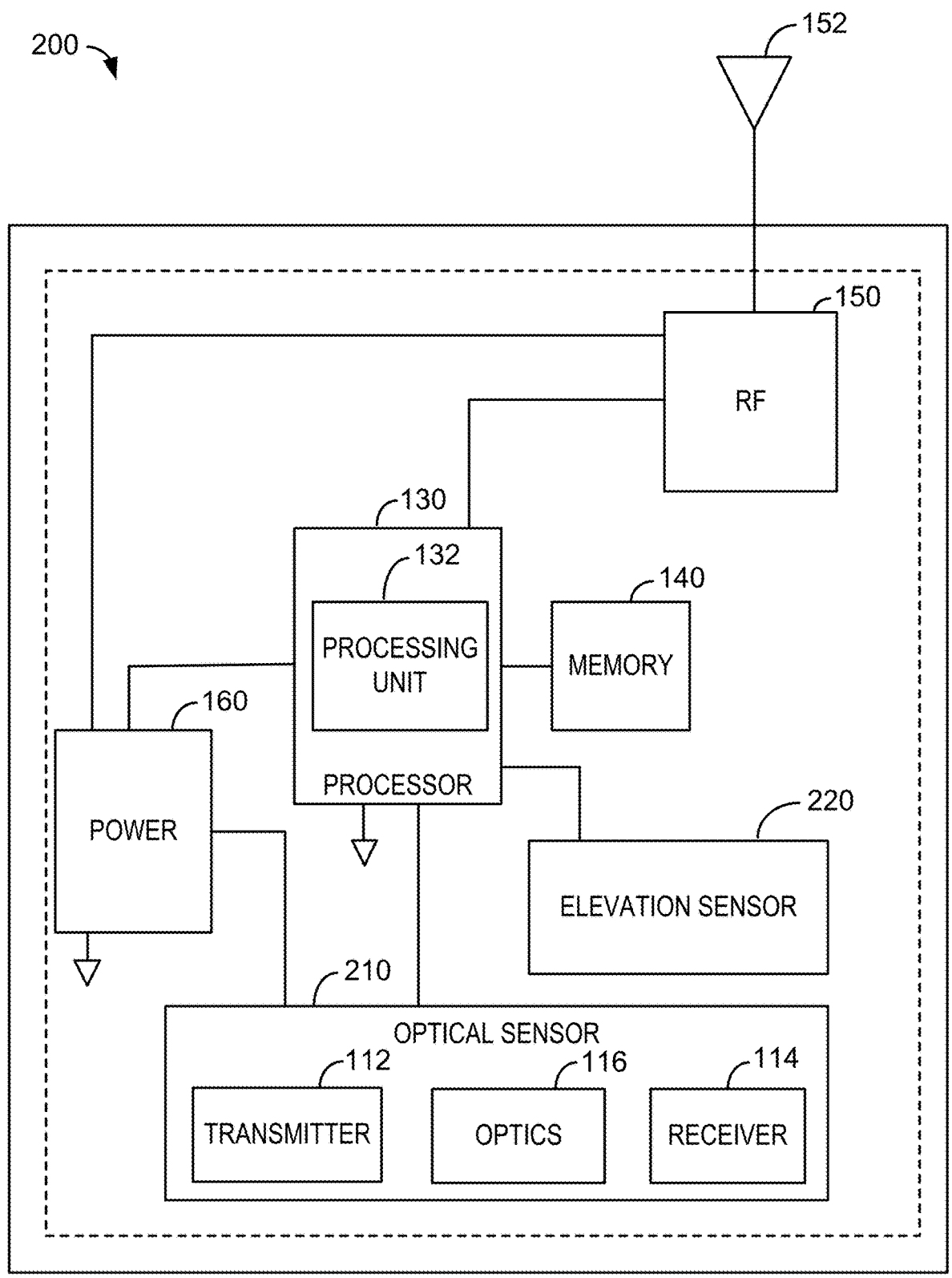
FIG. 2A illustrates a non-interfering optical blood pressure calculating device according to some embodiments.

FIG. 2A illustrates example components of a non-interfering optical blood pressure calculating device 200 according to some embodiments. An optical blood pressure calculating device 200 may include an optical sensor 210, an elevation sensor 220, a processor 130, memory 140, a radio frequency (RF) processor 150 coupled to an antenna 152, and a power supply 160.

In some embodiments, the optical sensor 210 is a laser Doppler velocimetry (LDV) sensor that may be used to obtain measurements of an arterial lumen and blood flow. Optionally, a transparent gel may be applied between the optical sensor 210 and the skin in order to reduce light scattering and perturbation from the skin surface.

The optical sensor 210 may include a light transmitter 112. In some embodiments, the light transmitter 112 may be configured to direct light into a subject's limb towards an artery to illuminate an artery with an interference pattern forming a measuring volume. For example, the light transmitter 112 may be configured to emit at least two beams of light along different directions of propagation that intersect or spatially overlap to form interference fringes within the measuring volume that includes an artery of the subject. According to some implementations, the light transmitter 112 is configured to emit coherent light. In some such implementations, the light transmitter 112 includes one or more lasers, such as laser diodes.

Figure 2B:
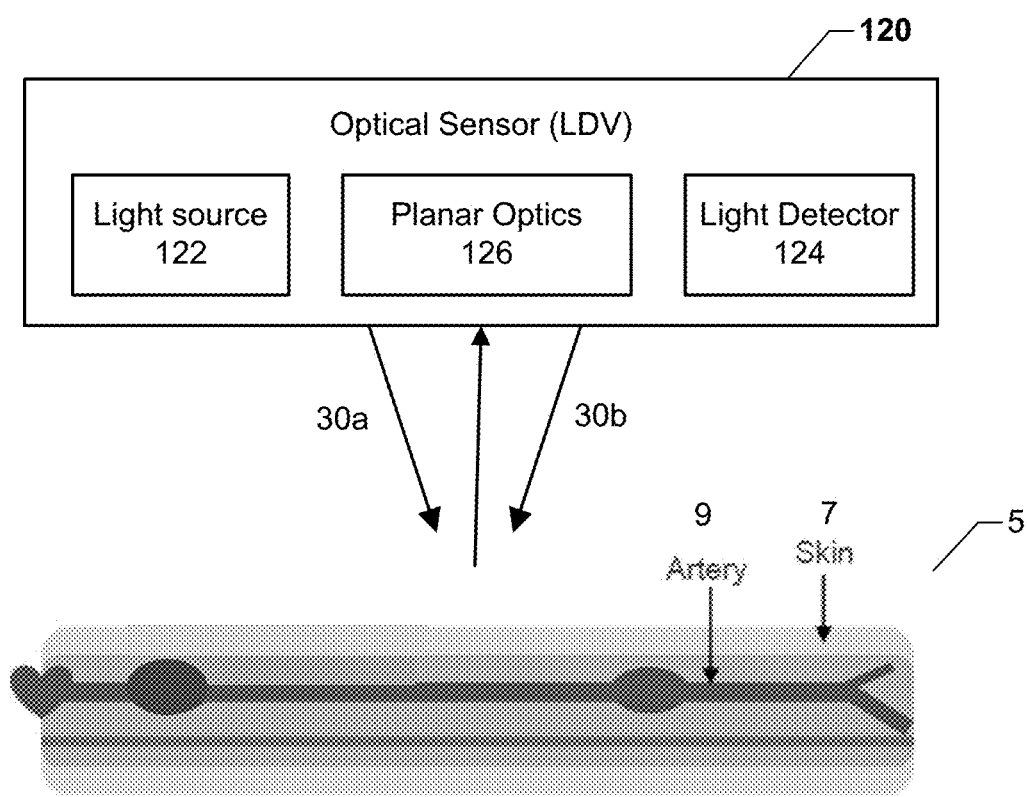
FIG. 2B illustrates a non-interfering optical blood pressure calculating device according to some alternative embodiments.

FIG. 2B illustrates a non-interfering optical blood pressure calculating device according to some alternative embodiments. In some embodiments, the optical sensor 120 may be implemented as a planar device configured to be arranged flush to, or at least parallel to, the skin surface 7 of a limb. The optical sensor 120 may include a light source 122, a light detector 124, and one or more planar optical structures 126 tailored to properties of blood cells moving in an artery 9.

In some embodiments, the light source 122 may be configured to emit light of a wavelength that is less susceptible to absorption by biological tissue and water. In various embodiments, the light source 122 may be a laser, such as an edge emitting semiconductor laser or a vertical cavity surface emitting laser (VCSEL) that produces a light beam having an optical wavelength in the range of 850 nanometers (nm) to 1500 nm. In some embodiments, a transparent gel may be applied between device and skin in order to further reduce light scattering and perturbation from the skin surface.

In some embodiments, the light detector 124 may be configured to detect backscattered light of a particular range of wavelengths. For example, a silicon (Si) diode may be used to detect wavelengths of light below 900 nm, a germanium (Ge) diode may be used to detect wavelengths up to 1300 nm, and a gallium arsenide (GaAs) diode or Indium phosphide (InP) diode may be used to detect longer wavelengths. The output signal of the light detector 124 may be converted to a voltage by a transimpedance amplifier (not shown) as known in the art.

In some embodiments, the optical sensor 120 may be configured to emit light 30a, 30b from the light source 122 and to collect and shunt backscattered light 32 to the light detector 124 through the one or more planar optical structures 126. In some embodiments, a planar optical structure 126 may be implemented as a planar transparent structure having refractive index structures, surface relief structures, diffractive structures, or other waveguide structures known in the art to tap the light from the light source 122 out of the optical sensor 120 and/or to collect and direct backscattered light towards the light detector 124.

In some embodiments, the planar optical structure 126 may be configured as a waveguide having a diffractive structure of two superimposed gratings. The superimposed gratings may be configured to have slightly different grating constants and a mean grating constant approximately equal to the optical wavelength of the light source, resulting in the emission of two light beams 30a, 30b that may intersect to form a light beam having an interference pattern that propagates perpendicularly away from the surface of the waveguide.

Figure 2C:
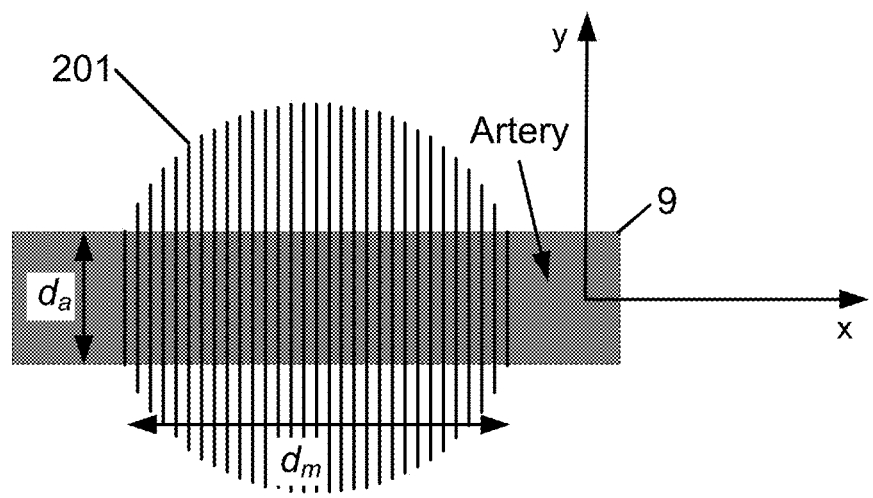
FIG. 2C illustrates a cross-section of a measuring volume having an interference pattern illuminating an artery according to some embodiments.

FIG. 2C illustrates a cross-section of a measuring volume 201 having an interference pattern illuminating an artery 9 according to some embodiments. In the illustrated embodiment, the interference pattern of measuring volume 201 may include a number of interference fringes that are parallel to the bisector of the axes of the two emitted beams and transverse an arterial longitudinal axis of the artery 9. In some examples, the interference fringes may be perpendicular to the arterial longitudinal axis of the artery 9, or approximately perpendicular to the arterial longitudinal axis of the artery 9. According to some implementations, the fringe spacing is larger than the typical size of blood cells (which may be approximately 10 µm in diameter). The number of fringes may, in some instances, be limited according to the expected length of the illuminated area ($d_m$). In some examples, the interference pattern may include between 5 fringes and 100 fringes, for example 20 fringes. In the example shown in FIG. 2C, the illustrated segment of the artery 9 is substantially straight, with an arterial longitudinal axis that corresponds with the x axis along this segment. In this example, the transverse or perpendicular axis corresponds with the y axis that is shown in FIG. 2C. The spacing between the fringes, or "fringe spacing," may be determined by the optical wavelength of the emitted beams and the angle between the emitted beams.

Using a Doppler velocimetry sensor, such as an LDV sensor, enables the measurement of the velocity of blood flowing parallel to the skin, as is the case in most arteries, particularly arteries in limbs and digits. A Doppler velocimetry sensor may also measure distinguish flowing blood from other tissues, and thus enable arterial lumen in the same measurement. In addition, Doppler velocimetry sensors have been used to measure flow rates in pipes and industrial applications, so the physics and configuration of such sensors is well understood.

A Doppler velocimetry sensor may be positioned on or adjacent to the skin of a subject and configured to direct two beams of light into the subject. So positioned and configured, the two beams of light propagate into the tissues perpendicular to the long axis of arteries beneath the skin. The measurement of velocity in an artery that is perpendicular to the overall direction of propagation of light is possible because the interference fringes are aligned in the same direction as the direction of the bisector of the two transmitted beams. The light scattered by moving blood cells will then be frequency modulated and the modulation frequency, $f_d$, will be given by the velocity, v, of the moving blood cells in conjunction with the spacing between interference fringes. This may be expressed as $f_d = v/\lambda/2 \sin(\alpha)$, where $\lambda$ represents the optical wavelength and $2\alpha$ represents the angle between the two transmitted beams. An alternative description is based on a so-called differential Doppler effect. The power of the frequency modulated part of the backscattered light and thus the amplitude of the dynamic part of a signal generated by a photodetector is proportional to the number of particles—cells in the case of blood—scattering light within the illuminated volume in the artery if so-called coherent detection is applied, which implies that light is collected within an angle smaller than $2\alpha$. According to some examples, light may be collected within an angle of $\alpha$ divided by the number of fringes of the interference pattern. If the light collection angle is much larger than $2\alpha$ the signal amplitude will be proportional to the square root of the number of particles (defined as "incoherent detection"). The area of the frequency shifted part of the power spectrum of the photodetector signal will in this latter case be proportional to the number of moving particles in the measuring volume.

In a Doppler velocimetry sensor, two beams are focused or directed so that the beams have different directions of propagation and intersect and thus interfere with each other within a measuring volume. The frequency shift observed in backscattered light is proportional to the velocity component of backscattering particles perpendicular to the bisector of the two beams. The two beams are assumed to originate from the same light source or at least from two mutually coherent light sources and also to have the same optical path length from the source (at least within the coherence length of the source). The two beams will form an interference pattern in the intersection region with interference fringes aligned in the direction of the bisector of the beams and a fringe spacing of $x_f = \lambda/(2 \sin \alpha)$, where $\alpha$ is half the angle between the two light beams. A particle moving through the interference pattern with a velocity component $v_x$ in the plane of the intersecting beams and perpendicular to the bisector of the light beams will scatter light modulated by a frequency given by the dot product of the velocity v and a vector defining the difference between the propagation vectors of the two beams divided by $2\pi$, i.e., $\Delta f = v_x/x_f = v \cdot \Delta k/2\pi$ where $\Delta f$ is the characteristic frequency shift observed in backscattered light, $v_x$ is the velocity component perpendicular to the propagation direction of light, $x_f$ is the fringe spacing of the interference pattern formed in a measuring volume, and the vector $\Delta k$ is the difference between the propagation vectors of the two light beams. The difference of the Doppler shifts of scattered light in a given direction (arbitrary) emerging from the two impinging beams will be independent of the scattering direction (direction of detection).

Figure 2D:
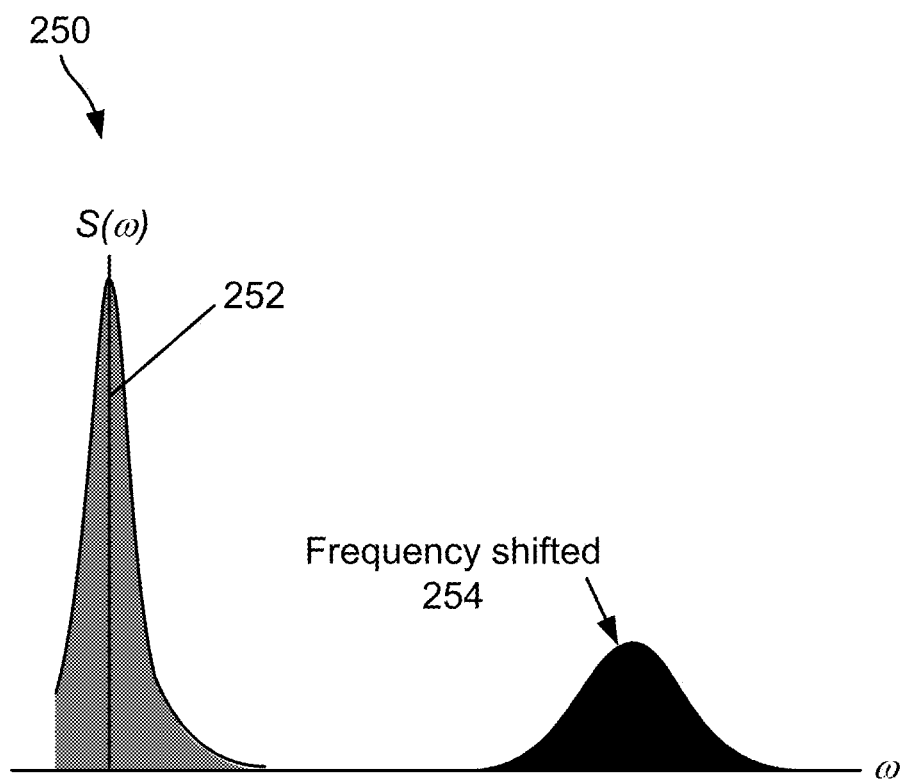
FIG. 2D is a plot of the magnitude of a photodetector signal versus frequency that indicates a static signal corresponding to tissues and a dynamic signal corresponding to blood.

Again, the power of the frequency shifted part of the photodetector signal will be proportional to the number of scattering particles, namely blood cells, in the measurement volume assuming incoherent detection (defined in [0049]). If the measurement volume (i.e., the volume in which interference fringes are formed by the intersecting beams) is larger than the artery as illustrated in FIG. 2C, some of the backscattered light will be from stationary tissue and some will be from moving blood. Thus, as illustrated in FIG. 2D which is a plot of the magnitude S of a photodetector signal (which is proportional to backscattered light intensity) (e.g., light receiver 114) versus frequency $\omega$, a photodetector may observe a static signal (non-shifted part 252) corresponding to tissues and a dynamic signal (i.e., frequency shifted part 254) corresponding to blood. Consequently, the velocity of blood may be inferred from the Doppler shift in backscattered light and the volume of blood may be inferred from the root mean square of the dynamic part of the signal of a photodetector.

Assuming an illuminated artery has a circular cross-section, the volume $V_m$ of the artery illuminated, and thus contributing the dynamic part of a signal of a photodetector, will be given by $$V_m = \frac{\pi}{4} d_a^2 \times d_m.$$

As the dynamic part of the signal of a photodetector is proportional to the volume of the illuminated portion of the artery and the density of blood, the diameter da of the artery can be calculated as a function of the photodetector signal knowing the dimension $d_m$ of the intersecting beams as illustrated in FIG. 2C.

Referring to FIG. 2A, in some embodiments, the light transmitter 112 may be configured to produce a fringe spacing that is greater than an average diameter of a blood cell. For example, to avoid a reduction in modulation depth and/or to minimize "wash-out" of the interference pattern caused by the light propagating through the biological tissue, fringe spacing in the range of 30 to 150 µm may be used as blood cells are typically disk shaped with a disk diameter in the order of 10 microns (µm).

In some embodiments, the light transmitter 112 may be configured to form the measuring volume 201 with an elliptical cross-section having a diameter ($d_m$) along the arterial longitudinal axis (e.g., the measuring direction) given by the beam diameter in the focal plane. An elliptical cross section may enhance the signal contribution from blood in the artery. In some embodiments, the light transmitter 112 may be configured to form the measuring volume 201 with a diameter $d_m$ that includes a desired number of interference fringes. For example, where the desired number of interference fringes is ten (10), the measuring volume 201 may extend 0.3 mm or more in the measuring direction.

To ensure that all of the blood cells moving through the artery 9 are illuminated (i.e., the whole arterial cross section is illuminated), the light transmitter 112 may be configured to produce a measuring volume 201 having an extension perpendicular to the measuring direction that is greater than the diameter $d_a$ of the artery (as illustrated in FIG. 2C). The length of extension may be determined by the focal diameter divided by the sine of half the angle between the two emitted beams. In some embodiments, the length of the extension may be greater than an average arterial diameter.

In some embodiments, the light transmitter 112 may be configured to emit light having a wavelength that will penetrate into biological tissue and water. For example, the light transmitter 112 may include a laser or other light source (e.g., an edge emitting semiconductor laser or a vertical cavity surface emitting laser (VCSEL)) that emits infrared light having an optical wavelength in the range of 850 nanometers (nm) to 1500 nm. In some embodiments, the light transmitter 112 may be configured to emit visible light.

The optical sensor 210 may include a light receiver 114. In some embodiments, the light receiver 112 may receive back scattered light and convert the received light power of the back scattered light to an electrical output signal using a photodetector (e.g., a photodiode). FIG. 2D illustrates a power spectrum 250 of an output signal that may be output by the light receiver 114. Again, the power spectrum 250 may include a non-shifted part 252 and a frequency shifted part 254. The frequency shifted part 254 of the power spectrum corresponds to the power (or intensity) of received light due to back scattering by moving particles (i.e., blood cells) moving through the interference pattern of the measuring volume 201 with a non-zero velocity, while the non shifted part 252 corresponds to the power of received light due to total back scattering by both moving blood cells and non-moving or slowly moving particles (e.g. arterial walls and other biological tissue).

In some embodiments, the light receiver 114 may include a photodetector configured to receive backscattered light of a particular range of wavelengths. For example, a silicon (Si) diode may be used to detect wavelengths of light below 1000 nm, a germanium (Ge) diode may be used to detect wavelengths up to 1400 nm, and a gallium arsenide (GaAs) diode or Indium phosphide (InP) diode may be used to detect longer wavelengths. In some embodiments, the light receiver 114 may include a photodetector configured to receive backscattered light in a range of visible wavelengths.

In some embodiments, the optical sensor 210 may include optics 116 (e.g., beamforming optics) configured to emit the intersecting (i.e., spatially overlapping) light beams. In some embodiments, beamforming optics of the optics 116 may include refractive, reflective and/or diffractive elements. According to some such embodiments, the beamforming optics may include a birefringent element and a polarizer. In some embodiments, the beamforming optics may include a volume hologram or a deep surface relief diffractive element. In some embodiments, the beamforming optics may include superimposed gratings, each have slightly different grating constants and a mean grating constant approximately equal to the optical wavelength of the light source to emit the light beams. In some embodiments, the beamforming optics may include separate gratings to emit the light beams. In some embodiments, the beamforming optics may include a planar transparent structure having refractive index structures, surface relief structures, diffractive structures, and waveguide structures known in the art to guide and direct light. According to some such examples, diffractive elements of the beamforming optics may be configured to generate a planar, or substantially planar, light beams. In some implementations, diffractive elements of the beamforming optics may be configured to generate overlapping beams with different directions of propagation.

In some embodiments, the light receiver 114 may be configured to include, or couple to, receiver optics through which to receive backscattered light. In some embodiments, the receiver optics of the light receiver 114 may be spatially separated from, or spatially multiplexed with, the beamforming optics of the light transmitter 112.

The elevation sensor 220 may be configured to provide an output that may be continuously converted to a measure of the elevation (or height) of the measuring location. For example, in some embodiments, the elevation sensor 220 may be a three-dimensional (3D) inertial sensor, such as a three-axis accelerometer. Elevation changes may be inferred from integration of the accelerometer output. Other examples of elevation sensors may include barometers magnetic near-field devices, or any other type of sensor configured to measure the elevation or a change in elevation of a measurement location.

The optical sensor 210 and the elevation sensor 220 may be coupled to the processor 130 so that the processor may control or receive outputs from each sensor. In some embodiments, the processor 130 may be dedicated hardware specifically adapted to perform a variety of functions for the optical blood pressure calculating device 200. In some embodiments, the processor 130 may be or include a programmable processing unit 132 that may be programmed with processor-executable instructions. In some embodiments, the processor 130 may be a programmable microprocessor, microcomputer or multiple processor chip or chips that can be configured by software instructions to perform a variety of functions for the optical blood pressure calculating device 200. In some embodiments, the processor 130 may be a combination of dedicated hardware and a programmable processing unit 132.

In some embodiments, the memory 140 may store processor-executable instructions and/or outputs from the optical sensor 210 and the elevation sensor 220. In some embodiments, the memory 140 may be volatile memory, non-volatile memory (e.g., flash memory), or a combination thereof. In some embodiments, the memory 140 may include internal memory included in the processor 130, memory external to the processor 130, or a combination thereof.

In some embodiments, the processor 130 may be configured to selectively control when the optical sensor 210 and the elevation sensor 220 are activated (e.g., turned on and off). In some embodiments, the processor 130 may be configured to receive output signals from the optical sensor 210 and the elevation sensor 220 to calculate values of one or more cardiovascular properties inferred from the sensor output signals. For example, in some embodiments, the processor 130 may be configured to determine values of blood flow, arterial lumen, hydrostatic pressure, and blood pressure based on these values.

In some embodiments, the processor 130 may be coupled to a radio frequency (RF) resource 150 coupled to an antenna 152 in order to communicate the calculated values and/or the output data from the sensors 210, 220 to a remote computing device (not shown) for presentation through a display or other output device. The RF resource 150 may be a transmit-only or a two-way transceiver processor. For example, the RF resource 150 may operate in one or more of a number of radio frequency bands depending on the supported type of communications.

The processor 130 may be configured to transmit measured or calculated information, such as measured values of the cardiovascular properties or the output from the sensors 210, 220 to a remote computing device (e.g., 300 of FIG. 3) for recording or display. Such a remote computing device may be any of a variety of computing devices, including but not limited to a processor in smart clothing, cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and a communication resource to communicate with the RF resource 150. Measured and/or calculated information may be transmitted from the optical blood pressure calculating device 200 to a remote computing device over a wireless link using Bluetooth®, Wi-Fi®, or other wireless communication protocol.

The optical sensor 210, the elevation sensor 220, the processor 130, the memory 140, the RF transceiver 150, and any other electronic components of the optical blood pressure calculating device 200 may be powered by a power supply 160. The power supply 160 may be a battery, a solar cell, or other energy harvesting power supply.

FIG. 3A illustrates a non-interfering blood pressure calculating device for estimating blood pressure that is worn on a limb (e.g., near the wrist) of a subject 5 according to some embodiments. In this example, the non-interfering blood pressure calculating device is capable of obtaining measurements using one or more optical sensors. However, other implementations of the non-interfering blood pressure calculating device may be capable of obtaining such measurements using one or more ultrasonic sensors. Some ultrasonic-based examples are provided below. In the illustrated embodiment, the optical blood pressure calculating device 200 may be worn at a particular measuring location on a wrist of the subject 5 relative to an artery of interest 9. In some embodiments, the optical blood pressure calculating device 200 may be attached to the skin surface with an adhesive or with an elastic band 115. Such an elastic band may be sized to ensure relatively low levels of counter pressure (i.e., inwardly from a surface of the skin) to ensure that the underlying artery is not perturbed. For example, in some embodiments, the optical blood pressure calculating device 200 may be configured in the form of, or incorporated into a wrist cuff, a patch, band of a wristwatch, or a back case of a wristwatch.

In other embodiments, the optical blood pressure calculating device 200 may be configured in the form of, or incorporated into, a finger sleeve, a finger ring, and/or other form of apparel (i.e., clothing that includes an embodiment of the optical blood pressure calculating device 200) in which the optical sensor 210 may be placed in optical contact with the skin of a subject at measurement location(s) and raised or lowered to different elevations. However, the various embodiments are not limited to implementations that are directly worn by a subject, and may include configurations that place the optical sensor 210 in optical contact with the skin of the subject. For example, in some embodiments, the optical blood pressure calculating device 200 may be incorporated into a reclining chair and other smart furniture configured so that the optical sensor 210 may be in optical contact with the skin of a subject at a measurement location (e.g., calf, ankle, etc.) and raised or lowered to different elevations. As a further example, in some embodiments, the optical blood pressure calculating device 200 may be incorporated into athletic equipment, such as helmets, racket handles, wrist or headbands, shoes, socks, handle bars, etc., and other athletic equipment configured so that the optical sensor 210 may be in optical with contact the skin of a subject at measurement location(s) and raised and/or lowered to different elevations.

Various embodiments of the optical blood pressure calculating device 200 may be configured to calculate blood pressure based on optical measurements of arterial lumen (also referred to as arterial distention) and blood flow as described above. As part of some embodiments (see, e.g., FIG. 5A), on optical measurements of arterial lumen and blood flow may be taken at two or more elevations of the measurement site on a limb, as illustrated in FIG. 3B. FIG. 3B illustrates elevations of the measurement location on a limb (wrist in FIG. 3B) of a subject 5 in a first elevation 302, which is approximately horizontal and thus about the elevation of the heart, and a second elevation 303 in a straight downward vertical orientation. Taking measurements at the two different measurement elevations and knowing the difference in elevation of the sensor during the two measurements enables calculation of blood pressure as described in further detail herein, such as in method 500 described with reference to FIG. 5A. In various embodiments, supporting the limb during the change in elevation may mitigate the effects of skeletal muscle flexion or other forms of tension on arterial cross-sectional properties. Measurements may also be taken at elevations not shown in FIG. 3B, such as when the optical blood pressure calculating device is above the heart and slightly below the heart (i.e., between elevations 302 and 303 in FIG. 3B).

Figure 4B:
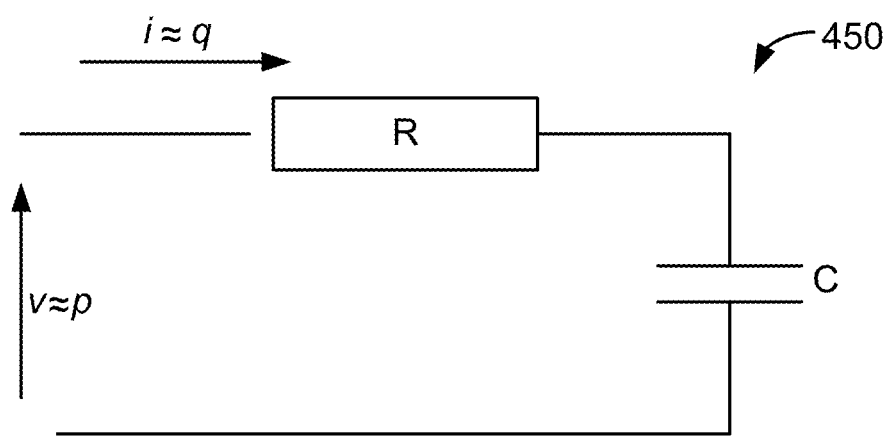
FIG. 4B illustrates a simple model that facilitates an evaluation of the relationship between flow and pressure.

FIG. 4A is a flow diagram that outlines one example of a method for calculating blood pressure according to a first embodiment. FIG. 4B illustrates a simple model that facilitates an evaluation of the relationship between flow and pressure. Although the following discussion of FIGS. 4A and 4B primarily involves obtaining and processing measurements taken by one or more optical sensors, the same principles for estimating blood pressure apply regardless of how the measurements are obtained. Other implementations may involve obtaining and processing measurements taken by one or more ultrasonic sensors in order to estimate blood pressure. In the illustrated embodiment, the method 400 is based upon modeling an arterial system as an electrically equivalent circuit. For example, FIG. 4B illustrates an electrically equivalent circuit 450 in which the arterial system is modeled as a resistor-capacitor (RC) circuit. As illustrated, a transmural pressure (p) and blood flow (q) may be modelled as a voltage (v) and an electrical current (i), respectively.

For semi-steady state conditions (e.g., slowly varying), the impedance of a peripheral arterial system and the capillary system may be modelled by a resistance (R), while the venous reservoir providing a return flow may be modelled as a capacitor (C). The capacitor C may be modelled as having an infinitely large capacitance value because venous pressure is generally close to zero. Given Ohm's law (i.e., $v=R\times i$), the transmural pressure p may be analogously expressed as having an electrically equivalent relationship between blood pressure and blood flow, i.e.:

$$p = R \times q \quad (1),$$

where the resistance parameter R may be assumed to be an unknown constant value for small variations of transmural pressure (i.e., comparable to or smaller than the pulse pressure). Assuming that the resistance R is a constant value, equation (1) may be valid for time averages of transmural pressure p and blood flow q. For example, the mean transmural pressure <p> during across one or more arterial pulses may be expressed as:

$$<p> = R \times <q> \quad (2),$$

where the mean blood flow <q> is typically determined in units of volume per unit time. By determining a value for the resistance parameter R, equation (1) or (2) may be used to calculate blood pressure (e.g., systolic blood pressure, diastolic blood pressure, means transmural pressure, pulse pressure, etc.) using the calculated value for the resistance parameter R and one or more values of blood flow.

Referring to FIG. 4A, according to some examples, various operations of the method 400 may be performed by a blood pressure calculating device. In some examples, the blood pressure calculating device may be the optical blood pressure calculating device 200, which may include an optical sensor (e.g., 210), an elevation sensor (e.g., 220), and a processor (e.g., 130) or other computing device and/or processor (e.g., 300) in communication with the blood pressure calculating device. In some implementations, parallel operations of the method 400 may be performed by a blood pressure calculating device that includes one or more ultrasonic sensors.

In block 410, the optical sensor of the optical blood pressure calculating device 200 (e.g., light transmitter 112) may direct light into a subject's limb towards an artery to form a measuring volume (e.g., 201) having an interference pattern that illuminates the artery. For example, in some embodiments, the optical sensor may direct two light beams having different paths of propagation into the limb that intersect or overlap to form the measuring volume. In some implementations that include one or more ultrasonic sensors, block 410 may involve directing ultrasonic waves from one or more ultrasonic sensors into a subject's limb towards an artery.

Block 415 may involve receiving backscattered radiation and generating output signals. In some implementations of block 415, the optical sensor of the optical blood pressure calculating device (e.g., light receiver 114) may receive backscattered light and generate output signals associated with at least two different elevations of the limb. In alternative implementations, block 415 may involve receiving backscattered ultrasonic waves and generating output signals associated with at least two different elevations of the limb.

For example, the optical blood pressure calculating device may be worn or otherwise placed in optical contact with the skin surface at a desired measuring location (e.g., finger, wrist, or other limb) that may be raised or lowered between a first elevation and a second elevation. In some embodiments, the optical sensor may be configured to continuously generate output signals that correspond to the backscattered light as the subject's limb (and consequently the optical sensor) is raised or lowered between the two elevations. In some embodiments, the optical sensor may be configured to generate an output signal that corresponds to the backscattered light in response to the elevation sensor detecting a constant or desired elevation. In some embodiments, each of the generated output signals may include a non-shifted part 252 and a frequency shifted part (e.g., 254). The frequency-shifted part may be separated or filtered from the output signals provided by the optical sensor by the processor using a high-pass filter, for example.

In block 420, the processor may process the frequency shifted part of the generated output signals to determine a difference in blood flow ($\Delta q$) between the at least two different elevations. In some embodiments, the processor may determine a difference in the mean (or average) blood flow between the two different elevations (i.e., $\Delta q = \langle q_1 \rangle - \langle q_2 \rangle$). In some embodiments, the mean blood flow $\langle q_1 \rangle$ or $\langle q_2 \rangle$ at a particular elevation may be determined based on the product of a mean value of blood velocity $\langle v \rangle$ and a mean value of arterial lumen $\langle a \rangle$, i.e., $\langle q_1 \rangle = \langle v_1 \rangle \times \langle a_1 \rangle$ and $\langle q_2 \rangle = \langle v_2 \rangle \times \langle a_2 \rangle$.

In some embodiments, the processor may determine the mean blood velocity at a particular elevation $\langle v_1 \rangle$, $\langle v_2 \rangle$ by averaging measured values of blood velocity $v_1$, $v_2$ obtained from the frequency shifted part of output signals associated with that elevation over one or more arterial pulses. For example, in some embodiments, a measured value of blood velocity, v, may be obtained as the product of a fringe spacing ($x_f$) of an interference pattern formed in a measuring volume (e.g., 201) and a frequency shift ($\Delta f$) measured between a non-shifted part (e.g., 252) and a frequency shifted part (e.g., 254) of an output signal, i.e., $$\Delta f = f_d = \frac{v}{\lambda / 2\sin(\alpha)}.$$

In some embodiments, the processor may determine the mean value of arterial lumen at a particular elevation $\langle a_1 \rangle$, $\langle a_2 \rangle$ by averaging measured values of the arterial lumen $a_1$, $a_2$ over one or more arterial pulses at that elevation. A measured value of arterial lumen, a, may correspond to an arterial cross-section or volume. In some embodiments, a volume measurement of the arterial lumen a may be based on an integral of the frequency shifted part of an output signal (e.g., 254). For example, with coherent light detection, the volume measurements may be proportional to the square root of the integral. With incoherent light detection, the volume measurements may be proportional to the integral. In some embodiments, the processor may convert the volume measurement of the arterial lumen a to an arterial cross-section by dividing the volume measurement by the cross-sectional diameter ($d_m$) of the measuring volume (e.g., 201).

In block 425, the processor may determine a hydrostatic pressure difference ($\Delta p$) between the at least two different elevations. For example, in a semi-steady state, a hydrostatic pressure difference ($\Delta p$) may be assumed equivalent to a difference in mean transmural pressure between two different elevations ($\langle p_1 \rangle - \langle p_2 \rangle$) and may be determined by calculating the following equation (2):

$$\Delta p = \rho_b g \Delta h \qquad (3),$$

where $\rho_b$ is a density of blood (i.e., 1060 kg/m$^3$), g is the gravitational acceleration (i.e., 9.81 m/s$^2$), and $\Delta h$ is a distance between the two different elevations that may be provided to the processor by the elevation sensor (e.g., 220).

In block 430, the processor may determine a resistance parameter R of an electrically equivalent relationship between blood pressure and blood flow based on the hydrostatic pressure difference ($\Delta p$) and the difference in blood flow ($\Delta q$) between the at least two different elevations. For example, as previously discussed, the electrically equivalent relationship between transmural blood pressure p and blood flow q may be modeled using a linear relationship expressed as equation (1), i.e. p=R×q, where the resistance parameter R is a constant value. Thus, in some embodiments, the resistance parameter R may be determined according to equation (4):

$$R = \Delta p / \Delta q = \rho_b g \Delta h / \Delta q \qquad (4).$$

In block 435, the processor may determine a blood pressure based on the electrically equivalent relationship between the blood pressure and blood flow using the calculated resistance parameter R and one or more values of blood flow. For example, by determining a value for the resistance parameter R, equation (1) or (2) may be used in some embodiments to calculate blood pressure (e.g., systolic blood pressure, diastolic blood pressure, means transmural pressure, pulse pressure, etc.) using the calculated value for the resistance parameter R and one or more values of blood flow that may be measured by a non-interfering blood pressure calculating device (e.g., a non-interfering optical blood pressure calculating device 200).

In block 440, the processor may present the calculated blood pressure through an output device. In some embodiments, the processor may present the calculated blood pressure through a display or audible component (not shown) of the optical blood pressure calculating device 200. In some embodiments, the processor may communicate the calculated blood pressure over a wired or wireless communication link via a RF resource 150 and antenna 152 to a remote computing device (e.g., 300) for visual or audible presentation.

Figure 5B:
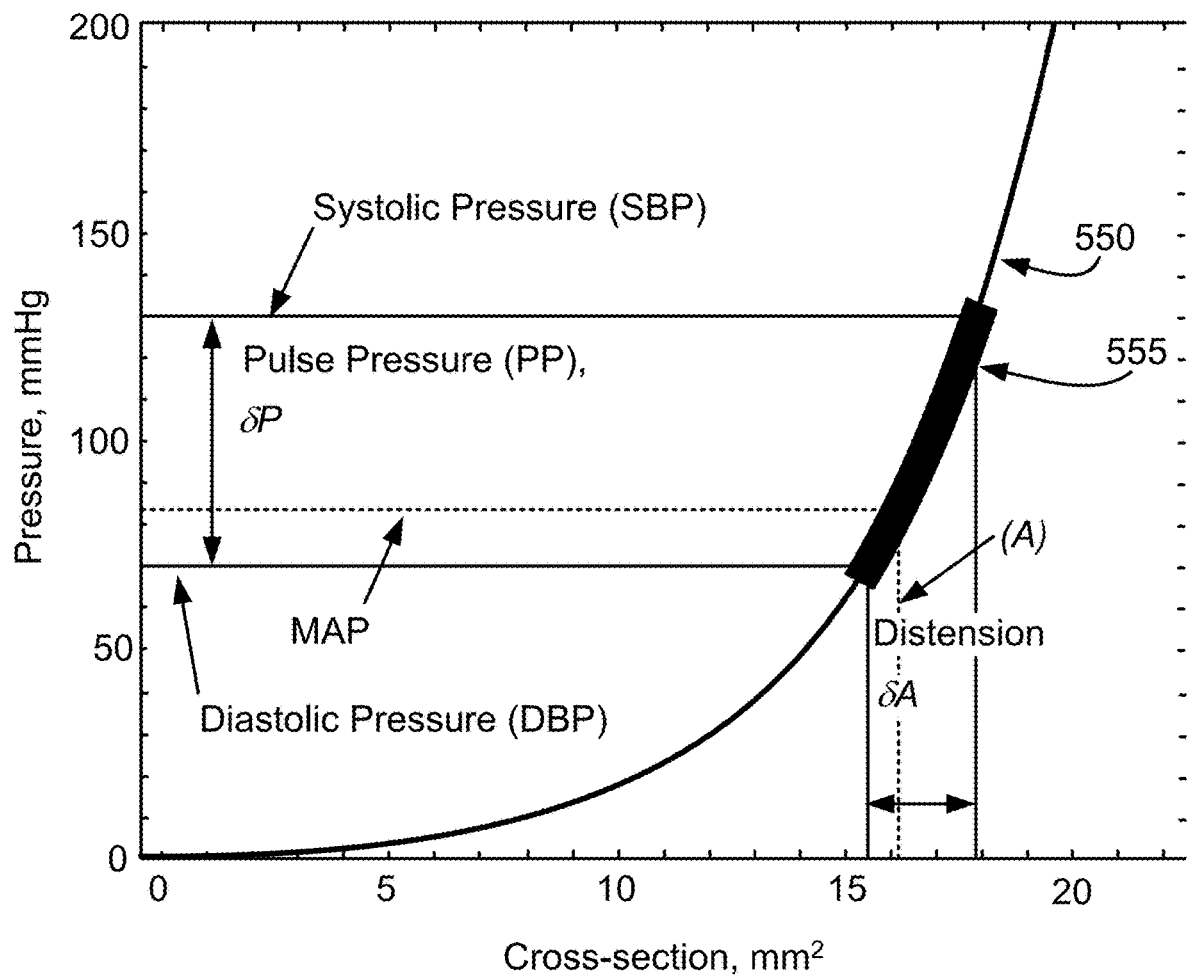
FIG. 5B is a graph that illustrates the relationship between arterial pressure and arterial cross-sectional area.

FIG. 5A is a flow diagram that outlines one example of a method for calculating blood pressure based on measurements of flow and lumen according to a second embodiment. FIG. 5B is a graph that illustrates the relationship between arterial pressure and arterial cross-sectional area. Although method 500 is described below primarily in terms of obtaining and processing measurements taken by one or more optical sensors, in some implementations the method may involve obtaining and processing measurements taken by one or more ultrasonic sensors. The method 500 is based upon modeling an arterial system using an arterial stress-strain relationship. FIG. 5B illustrates a stress-strain relationship for an artery with an exponential curve 550 as a plot of the cross-sectional area of an artery (in mm$^2$) on the horizontal axis versus the transmural pressure (in mmHg) on the vertical axis. A normal operating portion 555 (denoted by a thicker portion of the exponential curve 550) is defined at an upper end by a systolic pressure SBP and at a lower end by a diastolic pressure DBP. A difference between the systolic and diastolic pressures (i.e., the maximum and minimum pressures in a pulse respectively) reflects a pulse pressure δp. The right end of the normal operating portion 555 represents a maximum cross-sectional area of the artery corresponding to the systolic blood pressure (SBP), while the left end of the normal operating portion 555 of the curve represents a minimum cross-sectional area of the artery corresponding to the diastolic blood pressure (DBP). A difference between the arterial cross-sections at maximum and minimum pressures reflects the distension δa of the artery that may be observed during a single pulse cycle. A vertical dotted line in FIG. 5B represents the mean arterial cross-sectional area <a>, whereas a horizontal dotted line reflects the mean transmural pressure <p>.

An exponential relationship may be used to express the stress-strain relationship between arterial cross-section and transmural pressure typically present in an artery of a subject, such as a living human being or an animal. For example, the exponential relationship may be expressed as:

$$p = x_0 a_0 (e^{a/a_0} - 1) \quad (5),$$

where p is the transmural pressure, $x_0$ and $a_0$ are a priori unknown parameters, and a is a measurement of arterial lumen at a particular measuring location. The coefficient $x_0$ is a person specific parameter, which may be considered to be constant over time scales that are relevant in the present context (e.g., less than one year). The coefficient $a_0$ reflects specific properties (e.g., elasticity) of an artery of interest at a particular point in time, since many properties of arteries change over time. In some embodiments, the measurement of arterial lumen may be a volume or a cross-sectional area.

By determining values for coefficients $x_0$ and $a_0$, a blood pressure may be calculated by evaluating the arterial stress-strain relationship of equation (4) for optical measurements of arterial lumen a. For example, the systolic blood pressure (SBP) may be determined by evaluating the arterial stress-strain relationship as a function of the maximum value of the arterial lumen. The diastolic blood pressure (DBP) may be determined by evaluating the arterial stress-strain relationship as a function of the minimum value of the arterial lumen. The pulse pressure δp may be determined by evaluating the arterial stress-strain relationship as a function of the arterial distension δa.

Referring to FIG. 5A, various operations of the method 500 may be performed by a blood pressure calculating device. In some examples, the method 500 may be performed by an optical blood pressure calculating device (e.g., 200) that may include an optical sensor (e.g., 210), an elevation sensor (e.g., 220), and a processor (e.g., 130) and/or an external processor (e.g., 300) in communication with the optical blood pressure calculating device. In some implementations, parallel operations of the method 500 may be performed by a blood pressure calculating device that includes one or more ultrasonic sensors. The method 500 includes operations in blocks 410, 415, 425 and 440 as described with reference to FIG. 4A.

In block 510, the processor may process a frequency shifted part of the generated output signals (e.g., 254) to determine values of arterial lumen and blood flow during measurements at least two different elevations of a limb on which the optical blood pressure calculating device is positioned (see FIG. 3B). For example, in some embodiments, the processor may be configured to measure values of arterial distension (i.e., $\delta a_1$ and $\delta a_2$), mean cross-sectional area or volume of the arterial lumen (i.e., <$a_1$> and <$a_2$>) at two different elevations and a difference in blood flow during an arterial pulse at the two different elevations (i.e., $\delta q_1$ and $\delta q_2$).

In block 515, the processor may determine a first coefficient $a_0$ of an arterial stress-strain relationship based on the determined values of arterial lumen. In some embodiments, the model of the stress-strain relationship may be accessed from a memory (e.g., 140) or generated through execution of one or more processor-executable instructions by the processor. For example, as previously discussed, the stress-strain relationship between a transmural pressure (p) and arterial cross-sectional area (a) may be expressed using equation (4). Thus, pulse pressure δp may be approximated by the first derivative of equation (4) as follows:

$$\delta p = x_0 e^{<a>/a_0} \times \delta a \quad (6),$$

where $x_0$ and $a_0$ are unknown coefficients, <a> represents a mean value of arterial lumen (i.e., cross-sectional area or volume) during one or more arterial pulses and δa represents an arterial distension corresponding to a pulse pressure δp. When the subject is in a semi-steady state condition (e.g., slowly varying), the subject's pulse pressure δp at different elevations is generally constant. Thus, the ratio of equation (6) evaluated at two different heights may be expressed as:

$$1 = e^{(<a_1> - <a_2>)/a_0} \times \frac{\delta a_1}{\delta a_2}, \quad (7)$$

where $\delta a_1$ and $\delta a_2$ represent the arterial distension at two different elevations and <$a_1$> and <$a_2$> represent means values of arterial lumen at two different elevations. Thus, the processor may be configured to solve equation (6) for the coefficient $a_0$ according to equation 7:

$$a_0 = (a_1 - a_2) / \ln(\delta a_2 / \delta a_1) \quad (8).$$

In block 520, the processor may calculate a second parameter $x_0$ of the arterial stress-strain relationship based on the determined values of arterial lumen and blood flow, the hydrostatic pressure difference (Δp), and the first parameter $a_0$. For example, as previously discussed, a transmural pressure p may be expressed using equation (1) as having an electrically equivalent relationship with blood flow, i.e., p=R×q, where the resistance parameter R is an unknown constant. Using this analogy, the pulse pressure (δp) may be expressed using equation (8):

$$\delta p = x_0 e^{<a>/a_0} \times \delta a = R \delta q \qquad (9),$$

where <a> may be equal to the mean cross-sectional area or volume of arterial lumen at an elevation (i.e., <$a_1$> and <$a_2$>), δa may be equal to the arterial distension at the elevation (e.g., $\delta a_1$ or $\delta_2$), δq is the difference in minimum and maximum blood flow during an arterial pulse at a particular elevation (e.g., $\delta q_1$ or $\delta q_2$), and R is a constant value the resistance parameter that may be calculated as previously described (i.e., blocks 425 and 430 of FIG. 4A). Thus, in some embodiments, the second coefficient $x_0$ may be determined by according to equation (9):

$$x_0 = R\delta q / (e^{<a>/a_0} \times \delta a) \qquad (10).$$

In block 525, the processor may calculate a blood pressure based on the arterial stress-strain relationship using the first parameter $a_0$, the second parameter $x_0$, and one or more values of arterial lumen a. For example, in some embodiments, the one or more values of arterial lumen may be obtained by the processor continuing to obtain values of the arterial lumen from the output signals received from the optical sensor. In some embodiments, the processor may be configured to measure values of arterial distension (δa) and minimum, maximum, and/or mean values of arterial cross sectional area (a). Having determined values for both of the coefficients $a_0$ and $x_0$, the arterial stress-strain relationship (e.g. equation (4) or (5)) may be used by the processor to determine values of blood pressure by evaluating the model with the measured values of arterial lumen in block.

In some embodiments, the processor may calculate a subject's systolic blood pressure (SBP) based on the arterial stress-strain relationship expressed in equation (4) as a function of the maximum value of the arterial cross-sectional area a. In some embodiments, the processor may calculate a subject's diastolic blood pressure (DBP) based on the arterial stress-strain relationship expressed in equation (4) as a function of the minimum value of the arterial cross-sectional area a. In some embodiments, the processor may calculate a subject's pulse pressure δp based on a first derivative of the arterial stress-strain relationship expressed as equation (5) as a function of arterial distension (δa). In some embodiments, a remote computing device (e.g., 300) may be configured to determine the one or more blood pressure values.

FIG. 6A illustrates example components of a wearable ultrasound measuring device including a wearable ultrasound sensor according to various embodiments. In this example, the wearable ultrasound measuring device 600 includes a wearable ultrasonic sensor system 610, a processor 620, a radio frequency (RF) module 630 coupled to an antenna 632, and a power supply 640. Other implementations may include more, fewer and/or different elements than are shown in FIG. 6A. Various examples of suitable ultrasound sensors, as well as examples of using measurements obtained via ultrasound sensors to estimate blood pressure, are described below.

According to this implementation, the ultrasonic sensor system 610 includes a focusing layer 612, an ultrasound transmitter layer 614 and an ultrasound receiver layer 616. The focusing layer 612 may be mounted above the ultrasound transmitter layer 614. In this sense, the term "above" used to mean that the focusing layer 612 may be positioned between the ultrasound transmitter layer 614 and an external surface of the ultrasonic sensor system 610 that is intended to be positioned on a subject's skin, e.g., on a subject's limb. In some implementations, the focusing layer 612 may be mounted above the ultrasound receiver layer 616. In some examples, the ultrasonic sensor system 610 may have a substantially planar structure.

In some embodiments, the ultrasound transmitter layer 614 may be configured to generate ultrasonic plane waves. In some embodiments, the ultrasound transmitter layer 614 may include a layer of polyvinylidene fluoride (PVDF) or other piezoelectric material that converts electrical signals provided by the processor 620 into a continuous or pulsed sequence of ultrasonic plane waves. In some implementations, the ultrasound transmitter layer 614 may include capacitive ultrasound devices.

In some embodiments, the focusing layer 612 may include one or more lenses. The lenses may be capable of altering the paths of ultrasonic waves transmitted by the ultrasound transmitter layer 614. However, the lenses may or may not be transparent to visible light, depending on the particular implementation. Various examples of suitable lenses are disclosed herein. As described in more detail below, some implementations may include cylindrical lenses, whereas some implementations may include other types of lenses, such as spherical lenses or zone lenses. Some implementations may include concave lenses, whereas some implementations may include convex lenses. According to some implementations, each of the lenses may be configured to direct ultrasonic plane waves from the ultrasound transmitter layer 614 into an emitted focused beam of ultrasound. In some examples, the focused beam of ultrasound is a linear, or substantially linear, beam of ultrasound having a cross-section in which the dimension of a long axis is significantly longer than a perpendicular short axis.

In some implementations, an acoustic matching layer may be included in the focusing layer 612 to ensure proper acoustic coupling between the focusing lens(es) and the tissue. The acoustic matching layer can lower the acoustical miss-match between tissue and lens. The ideal acoustical impedance may in most cases be approximated by assuming planar wave incidence and identical acoustic impedance of the two material layers. In some examples, the acoustic matching layer may include an epoxy doped with particles that change the density of the acoustic matching layer. If the density of the acoustic matching layer is changed, then the acoustic impedance will also change according to the change in density, if the acoustic velocity remains constant. In alternative implementations, the acoustic matching layer may include silicone rubber doped with metal or with ceramic powder.

In some embodiments, the lenses may be configured with a focal length so that emitted ultrasound is focused into a beam at a distance that corresponds to an expected depth of an artery in a subject, which is typically several millimeters beneath the skin surface. In some embodiments, the focusing layer 612 may include lenses having different focal lengths to focus emitted ultrasound into a planar beam at different depths within tissues of the subject in order to accommodate different arterial depths and thus increase the likelihood of obtaining an output signal dominated by arterial information.

In some embodiments, the focusing layer 612 may include a lens, such as a cylindrical lens, oriented so that the emitted beam of ultrasound enters tissue at a non-orthogonal angle (θ) relative to the blood flow in an artery when the ultrasound measuring device 600 is positioned on a limb of a subject. This non-orthogonal angle (θ) of the emitted beam of ultrasound may facilitate measuring blood flow velocity in the artery by measuring a Doppler shift in ultrasonic reflections.

In some embodiments, sampling strategies for processing output signals may be implemented that take advantage of ultrasonic reflections being received through a lens of the focusing layer 612. An acoustic wave coming back from a lens' focal point will travel into the lens and may propagate towards multiple receiver elements in a receiver array fulfilling the acoustic reciprocity principle. Depending on the signal strength coming back from the scattered field, an adjustment of the number of active receiver elements is possible. In general, the more receiver elements that are activated to receive the returned acoustic waves, the higher the signal-to-noise ratio. However, having more receiver elements activated may require a higher level of energy consumption. Accordingly, with a lower number of active receiver elements, the energy consumption by the wearable device may be lowered. Hence this design configuration can enable optimization of the device's power consumption. Including multiple receiver elements can also enable some amount of receive beamforming of the received signal along the plane of the acoustic sheet. This functionality can enhance the sensitivity of the sensor to certain areas along the focus line of the lens.

In some embodiments, the ultrasound receiver layer 616 may be configured to detect and generate output signals corresponding to detected ultrasonic reflections resulting from interactions of various tissues with the emitted beam of ultrasound. In some embodiments, the ultrasound receiver layer 616 may include an ultrasound transducer layer and a thin film transistor (TFT) layer. In some embodiments, the ultrasound transducer layer may include a layer of polyvinylidene fluoride (PVDF) or other piezoelectric material and the TFT layer may include one or more receiver arrays. The ultrasound transducer layer may be capable of converting reflections of a beam of ultrasound into electrical signals, which may be amplified by a receiver array configured in the TFT layer. The amplified signals from the one or more receiver arrays may be provided as an output that is provided to the processor for use in calculating or estimating one or more cardiovascular properties.

The ultrasonic sensor system 610 may be coupled to the processor 620 so that output signals of detected ultrasonic reflections can be processed. In some embodiments, the processor 620 may be dedicated hardware specifically adapted to perform a variety of processes on the output signals, such as filtering, gating, amplifying, and spectrum analysing. In some embodiments, the processor 620 may be or include a processing unit 621 and a memory 622, and the processor 620 (e.g., a programmable microprocessor, microcomputer or multiple processor chip) may be configured by processor-executable instructions to perform a variety of computations on the output signals, such as calculating one or more cardiovascular properties. In some embodiments, the processor 620 may be a combination of dedicated hardware (e.g., filters, gates, analog-to-digital conversion, etc.) and a programmable processing unit 621 configured to perform calculations using processed results from the dedicated hardware. The processor 620 may be coupled to the memory 622, which may be volatile or non-volatile memory, such as flash memory, or a combination thereof.

In some embodiments, the processor 620 may be configured to transmit signals to the ultrasound transmitter layer 614 in order to generate a continuous or pulsed sequence of ultrasonic plane waves, which are emitted from the focusing layer 612 as one or more beams of ultrasound. The processor 620 may, for example, be part of the control system 190 that is described above with reference to FIG. 1D.

In some embodiments, the processor 620 may be further configured to receive and process output signals from a receiver array configured in the ultrasound receiver layer 616 in order to produce measurements of one or more cardiovascular properties. In some embodiments, the processor 620 may be configured to estimate one or more cardiovascular properties based on output signals received from multiple receiver arrays configured in the ultrasound receiver layer 616. For example, by processing output signals from two or more receiver arrays arranged at different locations in the ultrasound receiver layer 616, the processor 620 may be able to measure a pulse transit time (PTT).

The processor 620 may be coupled to RF module 630 coupled in order to communicate sensor output and/or measured cardiovascular properties via an antenna 632 to a remote computing device (not shown) for presentation through a display or other output device. The RF module 630 may be a transmit-only, or a two-way transceiver module. For example, the RF module may include base band, intermediate and transmit frequency modules and encoders. The RF module 230 may operate in one or more of a number of radio frequency bands depending on the supported type of communications.

The processor 620 may be configured to transmit measured or calculated information, such as measured values of the cardiovascular properties or the output from the ultrasonic sensor system 610, to a remote computing device (not shown) for recording or display. Such a remote computing device may be any of a variety of computing devices, including but not limited to a processor in smart clothing, cellular telephones, smart-phones, web-pads, tablet computers, Internet enabled cellular telephones, wireless local area network (WLAN) enabled electronic devices, laptop computers, dedicated healthcare electronic devices, personal computers, and similar electronic devices equipped with at least a processor and a communication resource to communicate with the RF module 230. Measured and/or calculated information may be transmitted from the wearable ultrasound measuring device 600 to a remote computing device over a WLAN wireless link (e.g., Bluetooth®, Wi-Fi®, or other wireless communication protocol).

The ultrasonic sensor system 610, the processor 620, the RF module 630, and any other electronic components of the wearable ultrasound measuring device 600 may be powered by a power supply 240. In some embodiments, the power supply 640 may be a battery, a solar cell, or other type of energy harvesting power supply.

In various embodiments, some or all of the components of the wearable ultrasound measuring device (e.g., 610, 620, 630, and 640) may be supported by a back support 650. In some embodiments, the back support 350 may be implemented with flexible materials so that the wearable ultrasound measuring device 600 may wrap around or otherwise conform to the surface of the subject, such as a finger, wrist, or other limb. In some embodiments, the back support 650 may be rigid. In some embodiments, the back support 650 may provide flexibility in one portion of the wearable ultrasound measuring device 600, while the rest of the device has a rigid structure.

In some embodiments, the wearable ultrasound measuring device 600 may be configured in the form of, or incorporated into, a patch, a finger sleeve, a wrist cuff, a finger ring, band of a wrist watch, back case of a wrist watch, and/or other form of apparel (i.e., clothing that includes an embodiment of the wearable ultrasound measuring device 600). However, the various embodiments are not limited to implementations that are directly worn by a subject, and may include configurations that place the ultrasonic sensor system 610 against the skin of the subject. For example, in some embodiments, the wearable ultrasound measuring device 600 may be incorporated into safety belts, steering wheels, portable devices, such as a hand-held devices, and configured so that the ultrasound sensor(s) contact (or are brought close to) the skin of a subject. As a further example, in some embodiments, the wearable ultrasound measuring device 600 may be incorporated into athletic equipment, such as helmets, racket handles, wrist or headbands, shoes, socks, handle bars, etc., and configured so that the optical sensor(s) contact the skin of a subject. In some examples, the ultrasound measuring device 600 may be incorporated into a steering wheel.

Figure 6B:
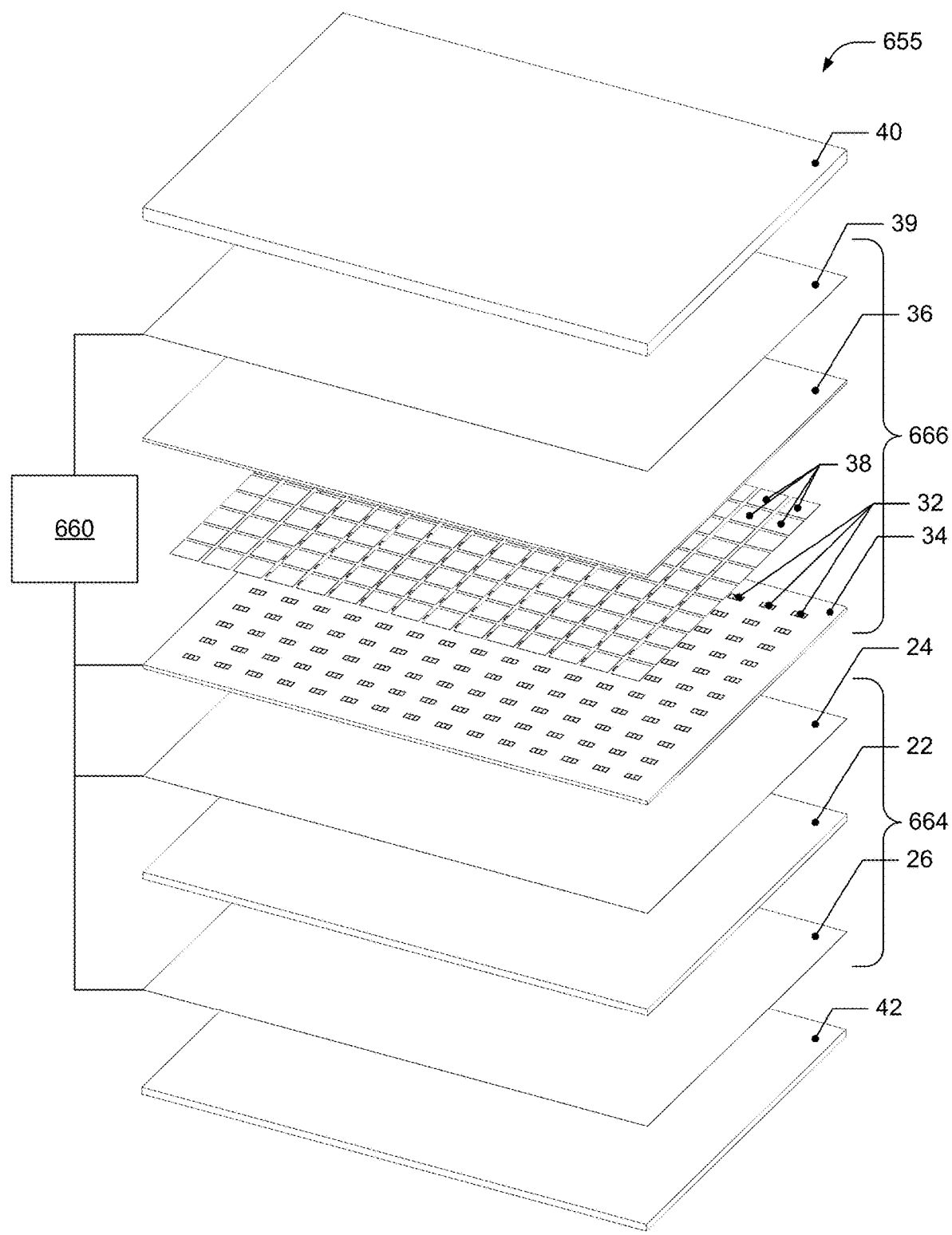
FIG. 6B shows an example of an exploded view of an ultrasonic sensor system.

FIG. 6B shows an example of an exploded view of an ultrasonic sensor system. In this example, the ultrasonic sensor system 655 includes an ultrasonic transmitter 664 and an ultrasonic receiver 666 under a platen 40. The ultrasonic transmitter 664 and the ultrasonic receiver 666 are examples of the ultrasound transmitter layer 614 and the ultrasound receiver layer 616, respectively. Accordingly, the ultrasonic sensor system 655 provides more detailed examples of one embodiment of the ultrasonic sensor system 610, except that the focusing layer 612 is not illustrated in FIG. 6B.

In some examples, the control system 660 may correspond with the processor 620 shown in FIG. 6A. In some examples, the control system 660 may be, or may be a portion of, the control system 190 of FIG. 1D.

The ultrasonic transmitter 664 may include a substantially planar piezoelectric transmitter layer 22 and may be capable of functioning as a plane wave generator. Ultrasonic waves may be generated by applying a voltage to the piezoelectric layer to expand or contract the layer, depending upon the signal applied, thereby generating a plane wave. In this example, the control system 660 may be capable of causing a voltage that may be applied to the piezoelectric transmitter layer 22 via a first transmitter electrode 24 and a second transmitter electrode 26. In this fashion, an ultrasonic wave may be made by changing the thickness of the layer via a piezoelectric effect. This ultrasonic wave may travel towards a target object, such as a limb, passing through the platen 40. A portion of the ultrasonic wave not absorbed or transmitted by the target object may be reflected so as to pass back through the platen 40 and may be received by the ultrasonic receiver 666. The first and second transmitter electrodes 24 and 26 may be metallized electrodes, for example, metal layers that coat opposing sides of the piezoelectric transmitter layer 22.

The ultrasonic receiver 666 may include an array of sensor pixel circuits 32 disposed on a substrate 34 (which also may be referred to herein as a backplane) and a piezoelectric receiver layer 36. In some implementations, each sensor pixel circuit 32 may include one or more TFT elements, electrical interconnect traces and, in some implementations, one or more additional circuit elements such as diodes, capacitors, and the like. Each sensor pixel circuit 32 may be configured to convert an electric charge generated in the piezoelectric receiver layer 36 proximate to the pixel circuit into an electrical signal. Each sensor pixel circuit 32 may include a pixel input electrode 38 that electrically couples the piezoelectric receiver layer 36 to the sensor pixel circuit 32.

In the illustrated implementation, a receiver bias electrode 39 is disposed on a side of the piezoelectric receiver layer 36 proximal to platen 40. The receiver bias electrode 39 may be a metallized electrode and may be grounded or biased to control which signals may be passed to the array of sensor pixel circuits 32. Ultrasonic energy that is reflected from the exposed (top) surface 42 of the platen 40 may be converted into localized electrical charges by the piezoelectric receiver layer 36. These localized charges may be collected by the pixel input electrodes 38 and passed on to the underlying sensor pixel circuits 32. The charges may be amplified or buffered by the sensor pixel circuits 32 and provided to the control system 660.

The control system 660 may be electrically connected (directly or indirectly) with the first transmitter electrode 24 and the second transmitter electrode 26, as well as with the receiver bias electrode 39 and the sensor pixel circuits 32 on the substrate 34. In some implementations, the control system 660 may operate substantially as described above. For example, the control system 660 may be capable of processing the amplified signals received from the sensor pixel circuits 32.

The platen 40 may be any appropriate material that can be acoustically coupled to the receiver, with examples including plastic, ceramic, sapphire, metal and glass. In some implementations, the platen 40 may be a cover plate, e.g., a cover glass or a lens glass for a display. According to some such implementations, the platen 40 may include one or more polymers, such as one or more types of parylene, and may be substantially thinner. In some such implementations, the platen 40 may be tens of microns thick or even less than 10 microns thick.

Examples of piezoelectric materials that may be used to form the piezoelectric receiver layer 36 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF piezoelectric transmitter layer 22 is approximately 28 μm thick and a PVDF-TrFE receiver layer 36 is approximately 12 μm thick. Example frequencies of the ultrasonic waves may be in the range of 5 MHz to 666 MHz, with wavelengths on the order of a millimeter or less.

Figure 7A:
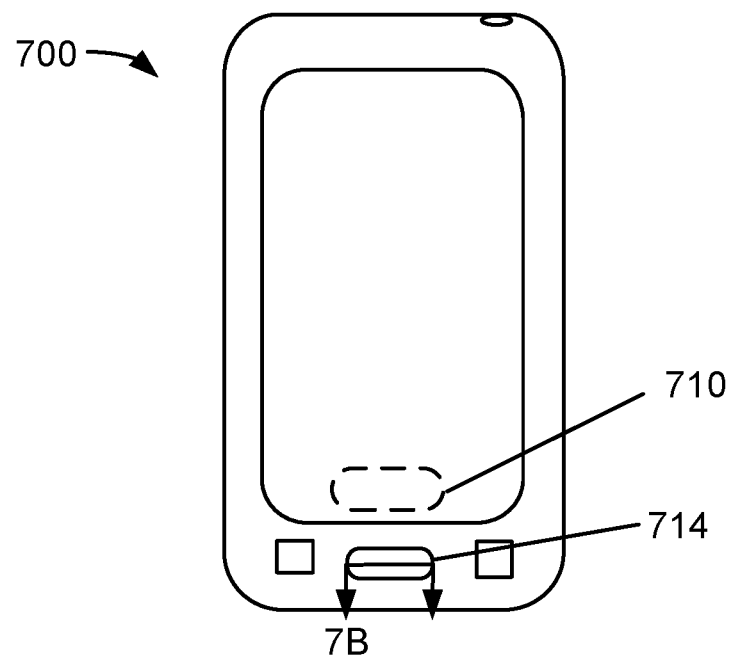
FIG. 7A is a block diagram of a mobile computing device configured for use as an ultrasound blood pressure calculating device according to some embodiments.
Figure 7B:
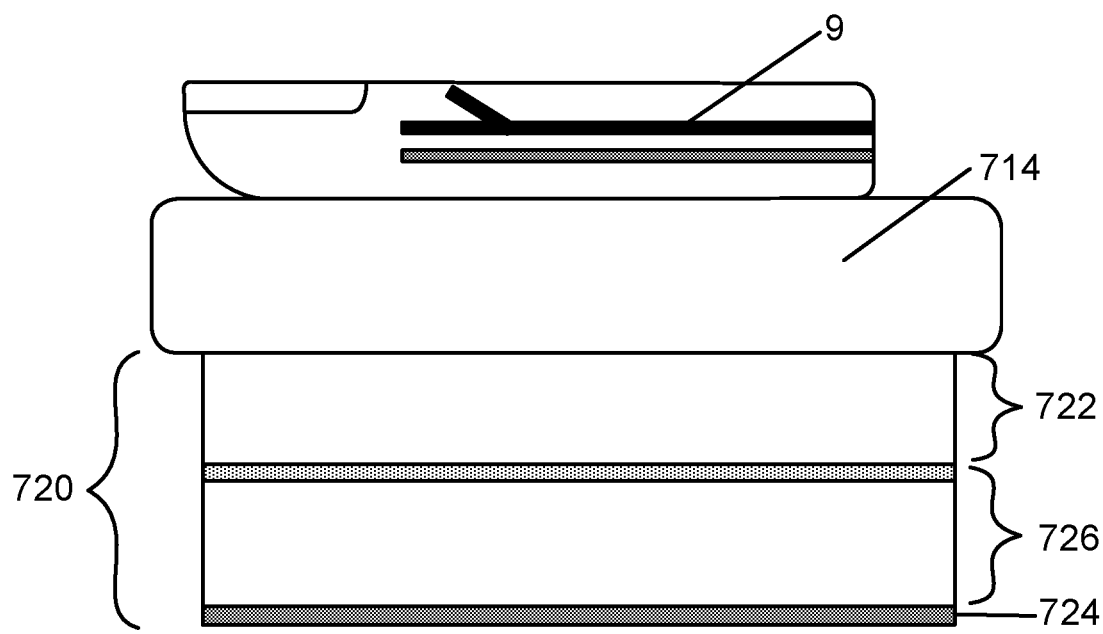
FIG. 7B is a cross-section through a portion of the mobile computing device of FIG. 7A.

FIG. 7A is a block diagram of a mobile computing device configured for use as an ultrasound blood pressure calculating device according to some embodiments. FIG. 7B is a cross-section through a portion of the mobile computing device of FIG. 7A. In this embodiment, an ultrasound sensor 720 is embedded within a button 714 (e.g., a thumb button) of the mobile computing device 700. In alternative implementations, an ultrasound sensor 720 may be embedded below a portion of the display glass 710 of the mobile computing device 700.

In this example, the ultrasound sensor 720 includes a focusing layer 722, an ultrasound transmitter layer 724, and an ultrasound receiver layer 726. The focusing layer 722 may be configured according to any of the focusing layer embodiments disclosed herein. One or more electronic components of the mobile computing device 700 may be coupled to the ultrasound sensor 720 and configured or adapted to function as one or more of the electronic components of an ultrasound measuring device (e.g., processor 620, RF module 630, and power supply 640 of FIG. 6A). In some embodiments, cardiovascular measurements, including those suitable for estimating blood pressure, may be performed by a control system of the mobile computing device 700 when a user places a finger 5 on the portion of the display glass 710 or on the button 714 overlying the sensor.

As noted above, some implementations of an ultrasound cardiovascular measuring device may include an ultrasonic sensor system and a control system. The ultrasonic sensor system may, in some examples, be an instance of (or a component of) the sensor system 185 that is shown in FIG. 1D and described above. The ultrasonic sensor system may, in some examples, be an instance of the ultrasonic sensor system 610 that is shown in FIG. 6A and described above. Likewise, the control system may, in some examples, be an instance of (or a component of) the control system 190 that is shown in FIG. 1D.

In some implementations, the ultrasound cardiovascular measuring device may be incorporated in a mobile device. For example, the ultrasonic sensor system may be integrated within a button or display of a mobile computing device and the control system may be a part of a control system of the mobile computing device. In some implementations, the ultrasound cardiovascular measuring device may be configured to be wearable. In some examples, the ultrasound cardiovascular measuring device may be integrated into a fixture (e.g., furniture, sports equipment, an automobile fixture such as a steering wheel, etc.) and may be configured to contact a subject when the subject uses the fixture.

The ultrasonic sensor system may, in some examples, include an ultrasound transmitter layer configured to generate ultrasonic plane waves. The ultrasonic sensor system may include a focusing layer. The focusing layer may include one or more lenses. In some examples, each of the lenses may be configured to focus the ultrasonic plane waves into a beam of ultrasound. According to some such examples, one or more of the lenses may be configured to focus the ultrasonic plane waves into a beam of ultrasound across an arterial longitudinal axis, such as the arterial longitudinal axis that is illustrated in FIG. 2C. However, the beam of ultrasound may or may not be perpendicular to the arterial longitudinal axis, depending on the particular implementation and use case.

The ultrasonic sensor system may, in some examples, include an ultrasound receiver layer. The ultrasound receiver layer comprising one or more ultrasonic receiver arrays configured to generate output signals corresponding to detected ultrasonic reflections.

The control system may be capable of processing the output signals to calculate values corresponding to one or more cardiovascular properties. Such cardiovascular properties may vary according to the particular implementation. In some examples, the cardiovascular properties may include distension, arterial diameter, arterial lumen and/or pulse wave velocity. According to some such examples, the control system may be capable of calculating a cross-sectional area of a blood vessel based, at least in part, on the output signals from the ultrasound receiver layer. In some implementations, the control system may be capable of performing multiple calculations of the cross-sectional area of the blood vessel based, at least in part, on output signals received from the ultrasound receiver layer at multiple times. In some such implementations, the control system may be capable of determining instances of heart beats, e.g., according to output signals from a microphone, output signals from the ultrasound receiver layer, detected changes in distension, arterial diameter, arterial lumen, etc. According to some such implementations, the output signals received from the ultrasound receiver layer at multiple times may be received at time intervals between the instances of heart beats.

In some examples, the lenses of the focusing layer may include a cylindrical lens, a spherical lens, a concave lens, a convex lens, a zone lens and/or a zone plate. In some implementations, the focusing layer may include acoustic matching material in which the one or more lenses are embedded. In some instances, the beam of ultrasound may be a linear, or substantially linear, beam of ultrasound. According to some implementations, the focusing layer may include at least two lenses that are spaced apart along the arterial longitudinal axis. In some such examples, the control system may be capable of calculating a pulse transit time or a pulse wave velocity of an arterial pressure pulse propagating along the arterial longitudinal axis.

In some instances, the focusing layer may include at least one lens that is oriented at an angle relative to an outer surface of the ultrasonic sensor system. The ultrasonic sensor system may be configured such that when in use, the lens is oriented at an angle that causes scattering and reflections of reflected acoustic waves related to the movement of the arterial blood. According to some such implementations, the control system may be capable of calculating a blood flow velocity based, at least in part, on a Doppler shift or Doppler shift related signal indicated by the output signals from the ultrasound receiver layer. In some examples, the focusing layer may include a first lens configured to focus the ultrasonic plane waves at a first focal depth and a second lens configured to focus the ultrasonic plane waves at a second focal depth. Various examples are disclosed herein and described below.

In some implementations, the cardiovascular properties may include blood pressure. According to some such implementations, the control system may be capable of controlling the ultrasonic sensor system to take at least two measurements, the at least two measurements including at least one measurement taken at each of two or more different measurement elevations of a subject's limb. In some such implementations, the control system may be capable of determining a blood flow difference based on the at least two measurements. According to some such implementations, the control system may be capable of determining a hydrostatic pressure difference based on the two or more different elevations of the at least two measurements. In some such implementations, the control system may be capable of estimating a blood pressure based on one or more values of blood flow, the hydrostatic pressure difference and the blood flow difference.

The lens(es) of the focusing layer may or may not be transparent to visible light, depending on the particular implementation. In some implementations, the ultrasound transducer may consist of a single element for acoustic emission and multiple receiver elements. The single transmit element may generate an acoustic wave front that at the top surface of the transducer stacking will be considered a plane wave. According to some implementations, the lens(es) can focus plane wave segments entering into the lenses so that the acoustic energy will be concentrated around the focal point of the lens. In some implementations, one or more such lenses may be configured such that when a wearable ultrasound sensor is being worn and is in use, the focal point of the lens(es) will be inside the wearer's tissue. Lenses applied in acoustics are elements having a shape (such as cylindrical, spherical, concave, convex, etc.) and sonic (i.e., speed of sound) characteristics that cause ultrasound to be refracted according to the refractive index for the lens material. In contrast to optics, acoustics does not have a reference medium. Optics uses the propagation speed of vacuum as a reference because it is a constant whereas sound waves do not have same fixed reference medium, because sound does not travel in a vacuum. In designing lenses to refract sound in medical applications, materials such as water or oil may be used as references if needed. The reason for mentioning this is that Snell's Law is applicable for both optics and acoustics, but it tells us that the refractive index is determined by the ratio between the refractive index between the lens material and the propagating material in front of the lens. In biomedical applications, the propagating medium will include tissue that will have a sound propagation speed on the order of 1500 m/s (on average). By investigating Snell's Law one will realize that a focusing of the sound waves can occur with both a concave and a convex lens architecture. Such focusing is caused by the ratio between the sound speeds of the mediums and the geometry of the lens.

Figure 8A:
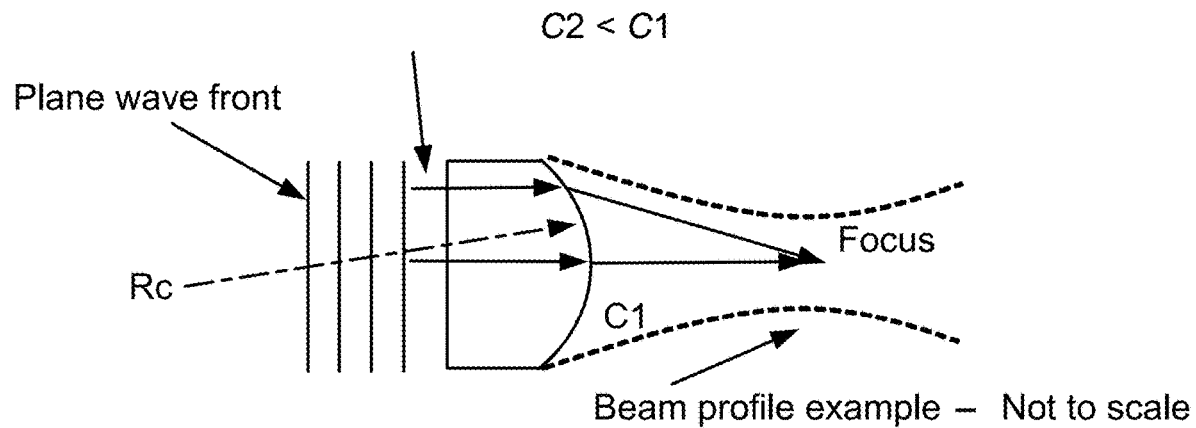
FIGS. 8A and 8B provide examples of concave and convex lenses that may be used in some implementations of a focusing layer.
Figure 8B:
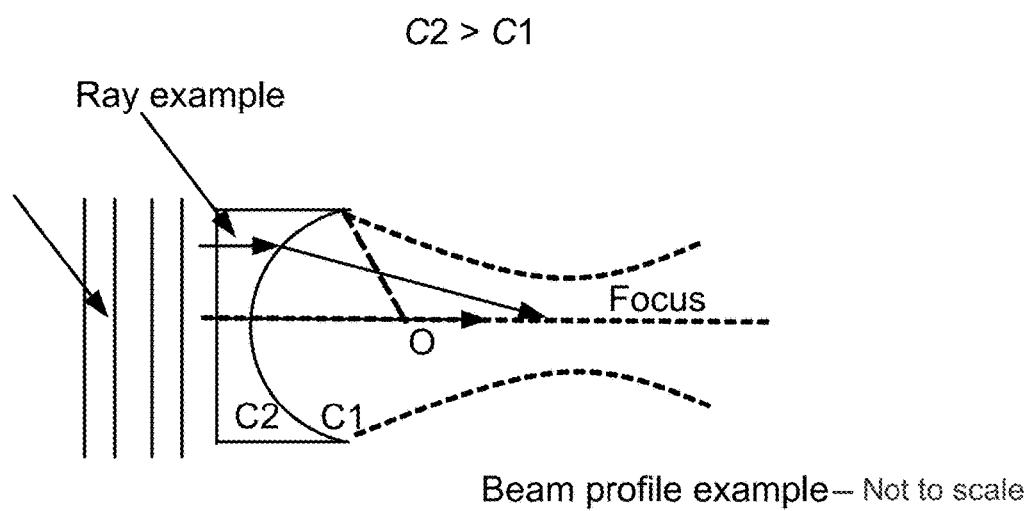

FIGS. 8A and 8B provide examples of concave and convex lenses that may be used in some implementations of a focusing layer. In these examples, C1 represents the speed of sound in the propagating medium outside of the lens and C2 represents the speed of sound in the lens. FIG. 8A shows an example of acoustic plane waves being focused by a convex lens, whereas FIG. 8B shows an example of acoustic plane waves being focused by a concave lens. In some embodiments, the lenses may be manufactured using injection moulded plastics, such as polystyrenes or acrylics.

Knowledge of the size of the focal area can be important for some implementations. The size of the focal area determines the tolerances within which the tissue of interest can be located. For example, it is preferable to have the focal point of the lens within the arterial cross section to ensure that most of the acoustical energy of the received acoustic wave is within the artery. In some signal processing procedures the extraction of the arterial properties may be more robust if this condition is met.

Figure 9:
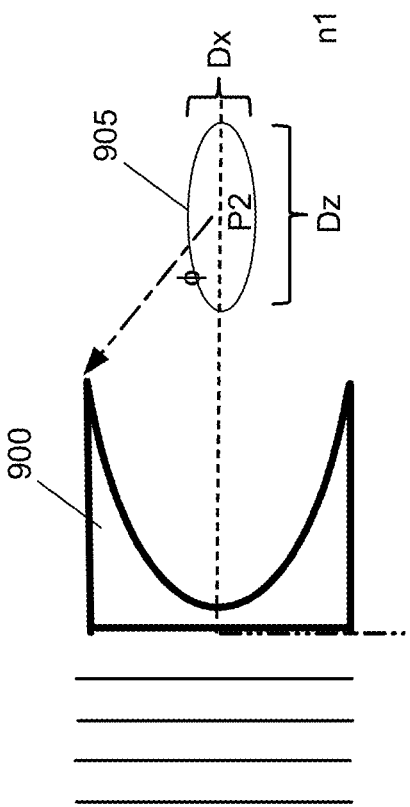
FIG. 9 shows an example of a lens suitable for inclusion in a focusing layer.

FIG. 9 shows an example of a lens suitable for inclusion in a focusing layer. Examples of equations that can be used to approximate the focal area size for an annular focusing element are shown below, with reference to FIG. 9. Again, C1 represents the speed of sound in the propagating medium outside of the lens and C2 represents the speed of sound in the lens. The index of refraction of the lens, n2, may be determined as follows $$n2 = \frac{1}{C2}$$

Likewise, the index of refraction of the propagating medium, n1, may be expressed as the inverse of the speed of sound in the propagating medium. For the lens to function as a concave lens, C2 should be greater than C1, which means that n2 would be less than n1.

The cross-sectional diameter of the focusing area 905 may be approximated according to the following expression:

$$Dx = Dy = K_t \lambda \left[\frac{F}{2a}\right],$$

wherein F represents the focal length of the lens 900, a represents the radius of the lens 900, λ represents the acoustic wavelength and $K_t$ is approximately 1 for angles less than 50 degrees.

In some examples, the size of the focal length may be determined according to finite element simulation.

In the examples provided above, the lenses have a continuous smooth surface on the focusing side. Other implementations may include different lens geometries.

Figure 10:
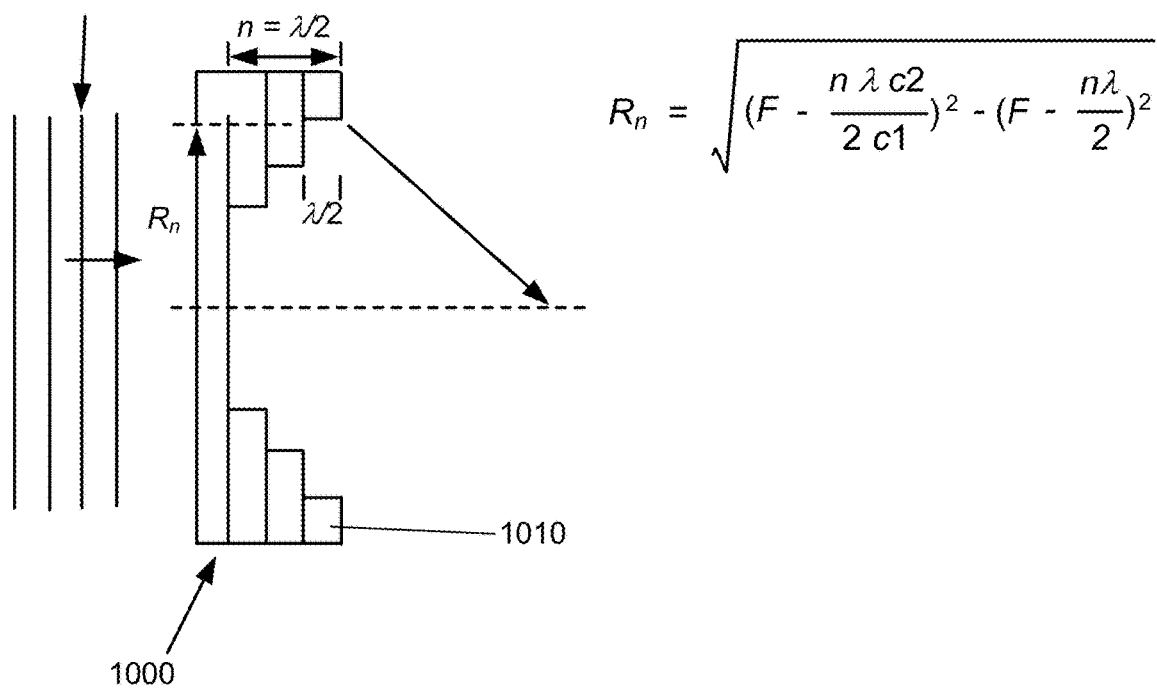
FIG. 10 shows an example of a zone lens that may be included in some embodiments of a focusing layer.
Figure 11:
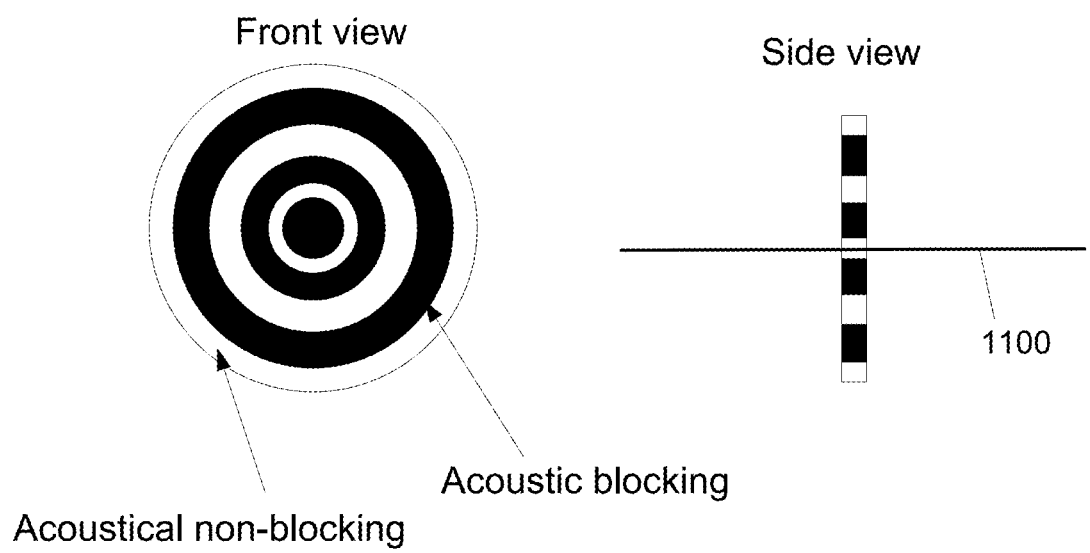
FIG. 11 shows an example of a zone plate suitable for inclusion in a focusing layer.

FIG. 10 shows an example of a zone lens that may be included in some embodiments of a focusing layer. The one lens 1000 of FIG. 10 utilizes the same general concept as the previously described concave lenses, but with the difference that the non-destructive interference is lowered at the focal point. In this example, the zone lens 1000 is constructed out of concentric layered rings 1010, which are positioned on top of each other. Such implementations may therefore, in some manufacturing processes, be easier to implement than concave lenses. In this example, each of the layered rings 1010 has a thickness of half a wave length. This will ensure that the wave fronts exiting from each of the layered rings 1010 will interfere in-phase. The concept is similar to a Fresnel plate, also referred to herein as a zone plate, although a Fresnel plate is planar. FIG. 11 shows an example of a zone plate suitable for inclusion in a focusing layer.

FIG. 11 shows front and side views of the zone plate. Acoustic waves may pass through the acoustical non-blocking material, but may be strongly attenuated by the acoustical non-blocking material. Acoustic waves that pass through the acoustical non-blocking material may interfere and cause the acoustic waves to focus a beam along the axis 1100.

Some implementations may include acoustic waveguides capable of guiding and focusing ultrasonic waves. For example, it is possible to focus sound by having a planar or curved surface that has drilled tunnels inside. These tunnels may be design in such a way that the acoustic travel time for an incident planar wave on the surface is different at different locations of the plate. Hence, the acoustic interference at a desired focal point can be tailored by manipulating the travel time.

Yet other implementations may include a lens that has a density gradient between the center of the lens and the edges of the lens. By manipulating the density one also manipulates the speed of sound in the material and therefore such a density gradient can cause focusing of ultrasonic waves.

Some examples of suitable materials for lenses of the type disclosed herein are presented in the following table, together with material parameters. This material list is not exhaustive and several other materials would be suitable applicable. The parameters presented are approximate values and are dependent on factors such as temperature.

TABLE 1

| Material | Symbol | Value [m/s] | Density ρ [kg/m³] | Acoustic Impedance Z $10^6$ kg/(s*m²) |
|---|---|---|---|---|
| Mineral oil | $C_{oil}$ | 1406 | | |
| GPPS (general purpose polystyrene) | $C_{gpps}$ | 2483 | 905 | 2.61 |
| PMMA (Poly(methyl methacrylate), also known as acrylic glass) | $C_{PMMA}$ | 2814 | 1180 | 3.32 |
| Epoxy | $C_{epoxy}$ | 2699 | 1080 | 2.45 |
| PVDF | $C_{PVDF}$ | 2200 | 1780 | 3.92 |
| PDMS (Polydimethylsiloxane) | $C_{PDMS}$ | 950 | 1580 | 1.5 |
| Silicon Rubber | | ~1000 | | |
| Skin | $C_{skin}$ | 1730 | 1150 | 1.99 |
| Water | $C_{Water}$ | 1480-1500 | 1000 | 1.48 |

In some implementations, the lens materials for convex lenses may include silicon rubber which may have speed of sound in the order of 1000 m/s. In some implementations, the lens materials for convex lenses may include PDMS, which may have a speed of sound in the order of 950 m/s. These materials will enable focusing of a convex lens into water/tissue with a speed of sound in the order of 1500 m/s.

Some implementations may include concave lenses that include materials such as PMMA or GPPS, or Epoxy.

The reflection coefficient may be one determining factor in selecting the appropriate lens material. The reflection coefficient may be expressed by the following:

$$R = 100 * \left(\frac{Z_2 - Z_1}{Z_2 + Z_1}\right)^1,$$

wherein $Z_1$ represents the impedance of a first medium and $Z_2$ represents the impedance of a second medium.

Some examples of lens/skin interfaces and corresponding reflection and transmission values are shown in the table below:

TABLE 2

| Interface | Reflection | Transmission |
|---|---|---|
| GPPS-Skin | 13.5% | 86.5% |
| PMMA-skin | 25.0% | 75% |
| Epoxy-skin | 10.4% | 89.6% |
| Water-skin | 14.6% | 85.4% |
| PVDF-skin | 32.7% | 67.3% |

From the reflection and transmission table one can see that Epoxy and GPPS would be suitable materials for an outer lens. GPPS is often found in medical ultrasound transducers because of its smooth surface structure. However, PMMA may also be a suitable lens material.

Epoxy has the advantage that it can easily be mixed with other materials to alter the density of the compound. One goal of mixing the materials could be to get the acoustic impedance as close to the skin impedance as possible, which would lower the reflected energy.

Attenuation is another factor that may be considered when selecting materials for lenses. GPPS and PMMA both have low acoustic damping which makes them attractive materials.

Figure 12:
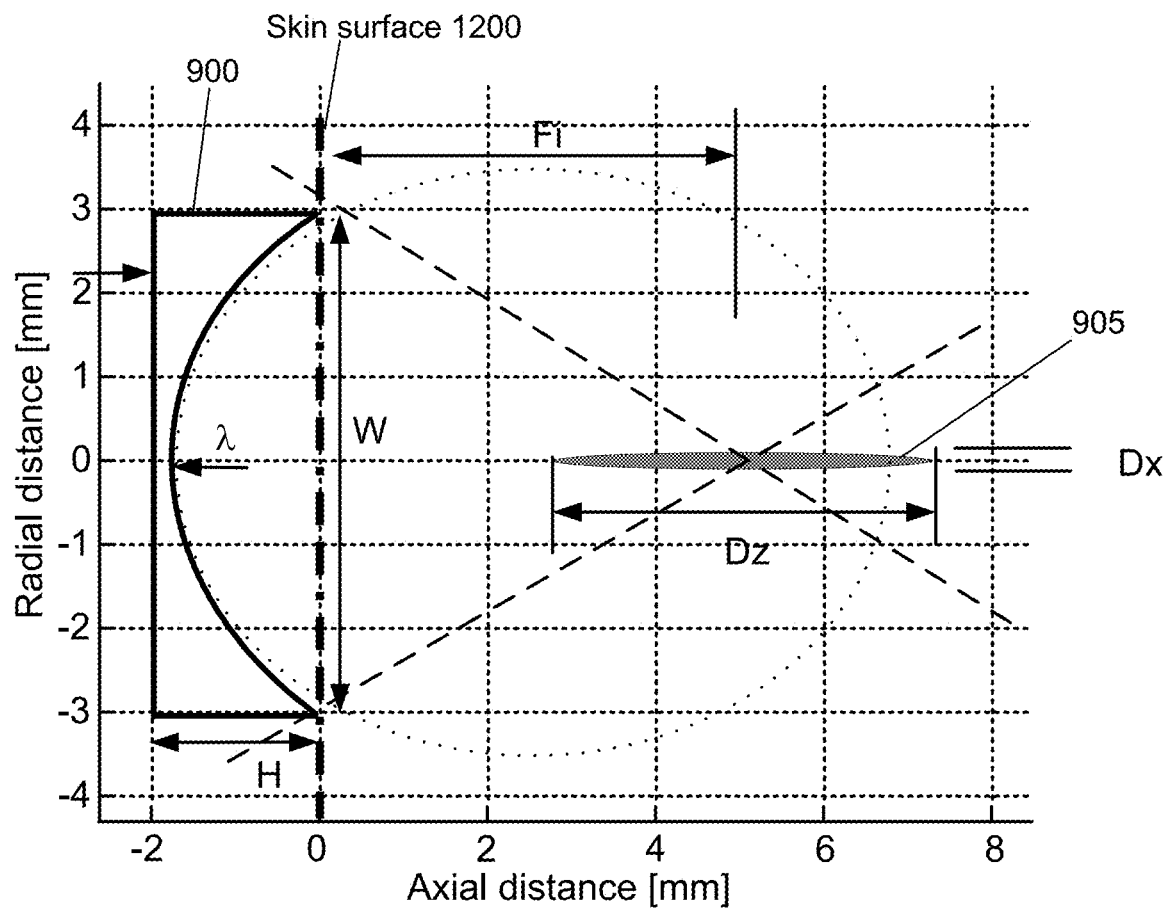
FIG. 12 shows another example of a lens suitable for use in a focusing layer.

FIG. 12 shows another example of a lens suitable for use in a focusing layer. In this example, the lens 900 is a concave lens that is adjacent to a skin surface 1200. Here, the lens 900 has a diameter W, a height H, a focal length $F_i$ and a focusing area 905 having dimensions $D_x$ and $D_z$.

Examples of input parameters for an embodiment such as that shown in FIG. 12, including four examples of $F_i$, are shown in the Table 3:

TABLE 3

| D | 5 mm |
|---|---|
| Lt | 50 mm |
| F1 | 5 mm |
| F2 | 2 mm |
| F3 | 7 mm |
| F4 | 4 mm |
| Ra | 2.0-3.1 mm |
| dRa | 46-300 μm |
| C1 | 1500 m/s |
| C2 | 2200 m/s |
| F0 | 10 MHz |
| λ | 220 μm |

In Table 3, $L_t$ represents a total length of a portion of a focusing layer that includes four lenses having focal lengths F1-F4, according to one example. The table below shows calculated dimensions of an array of lenses according to one such example:

TABLE 4

| | F1 = 5 mm | F2 = 2 mm | F3 = 7 mm | F4 = 4 mm |
|---|---|---|---|---|
| Major axis | 4.2 | 1.9 | 5.3 | 3.8 |
| Minor axis | 3.5 | 1.6 | 4 | 3.2 |
| Diameter W | 6 | 3 | 6 | 6 |
| Dz | 3.7 | 3.1 | 4.8 | 3.2 |
| Dx | 0.3 | 0.21 | 0.3 | 0.2 |
| F# | 1.13 | 0.97-1 | 1.46 | 0.96-1 |
| H | ~2 | 1.1 | 2 | 2 |
| λ | 0.22 | 0.22 | 0.22 | 0.22 |

Focal numbers F # in the order of 1 may be difficult to manufacture. However, the above example is only for illustrative purposes. In these examples, the parameter Dz is in the range of 3.2-4.8 mm, which is sufficient to cover the cross section of a radial or ulnar artery. In one example, the diameter of each lens would enable a building width of 21 mm in transducer length and 6 mm in width.

For some implementations that include a cylindrical lens, the length of the transducer may be on the order of 21 mm or larger (or smaller) and the width of the transducer across the desired artery may be in the order of 10 mm to 25 mm or larger. A smaller width would also be possible, but a sheet of sound would more look like a single focused sound beam as would be present with an annular focused lens.

Various embodiments disclosed herein include a wearable ultrasound sensor for use in a wearable ultrasound measuring device configured to obtain measurements of cardiovascular properties. In particular, some embodiments may include a wearable ultrasound sensor configured to direct ultrasound that is emitted as a plane wave, having a wave front that has a negligible curvature, so that the incident wave front is considered parallel to the lens. This wave front may be transformed by one or more lenses into one or more beams of ultrasound that can propagate into a limb of a subject. The wavelength of the plane wave is dependent on the excitation frequency of the generating piezoelectric material that initiates the acoustic wave by its electromechanical properties. The piezoelectric material may, in some examples, be polarized polyvinylidene fluoride (PVDF). The excitation frequency may be on the order of 10 MHz to 50 MHz for a device worn on the wrist or finger and targeting measurements on radial, ulnar or one of the digital arteries. An excitation frequency in this order will give a wavelength in tissue in the order of 30 µm to 150 µm and in a lens material of GPPS in the order of 49 µm-250 µm. The exact values will depend on the wave propagation in the materials used in the particular implementation. If, for example, PMMA is used a material between the emitter of PVDF and the lens then a wavelength on the order of 56 µm to 28 µm could be expected.

In some embodiments, the focused beam may have a long-axis dimension that enables the artery to remain within the beam of ultrasound despite possible arterial displacements or shifts in the position of the sensor. In some embodiments, the beam of ultrasound may be linear, or substantially linear. In some examples, the beam of ultrasound may have a cross-section with a long-axis dimension that extends for a range of rotational degrees about a location on the circumference of the limb (e.g., finger, wrist, ankle, etc.) at which the artery of interest is closest to the skin. In some embodiments, the planar wave of ultrasound may be emitted so that the long-axis dimension extends along a partial circumference of the limb. In some embodiments, the long-axis dimension of the planar beam of ultrasound may extend around the entire circumference of the limb. In some embodiments, the length of the planar wave of ultrasound perpendicular to the direction of the artery is larger than the width in the direction of the artery. Some embodiments may be capable of producing a focused beam of sound that is highly focused in the axial direction (e.g., as illustrated in the drawings for annular transducers) and distributed uniformly along the lateral direction of the tissue. Some such embodiments may include one or more cylindrical lenses. Some examples may produce a beam of ultrasound having a width and a length corresponding to the size of the lens(es) and a depth corresponding to the focal distance of the lens(es). The shape after the focal depth will generally correspond with a spreading of the acoustic energy, which may have less influence on the received acoustic response.

The various embodiments may provide a wearable ultrasound measurement device that is able to measure cardiovascular properties in a manner that minimizes or avoids artifacts from arterial displacements of the artery relative to the sensor. Such displacements may origin from limb conscious movements, tremors or inertial movement of the sensor due to e.g. arm swinging. Thus, wearable ultrasound measuring devices of various embodiments may be placed on the subject without a precise knowledge of the location of the artery.

Figure 13A:
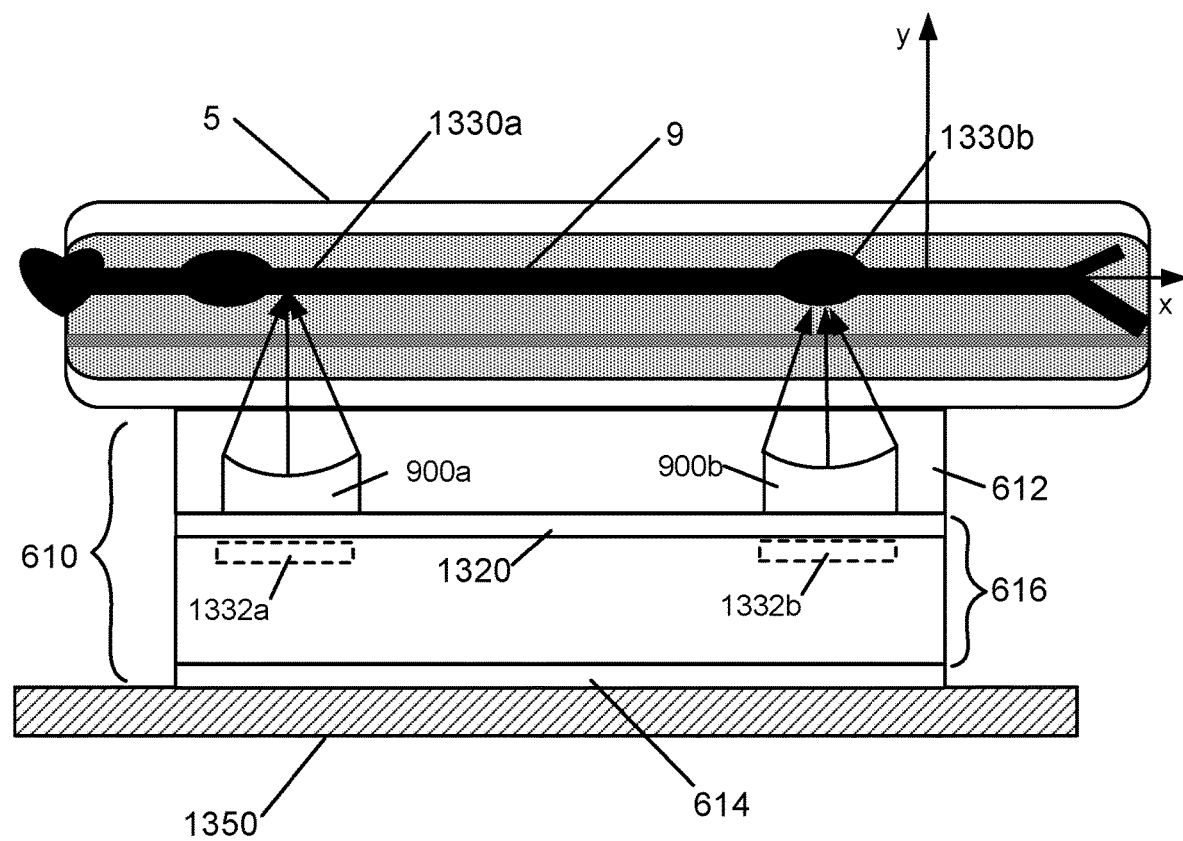
FIGS. 13A and 13B illustrate an ultrasonic sensor system having a focusing layer according to some embodiments.
Figure 13B:
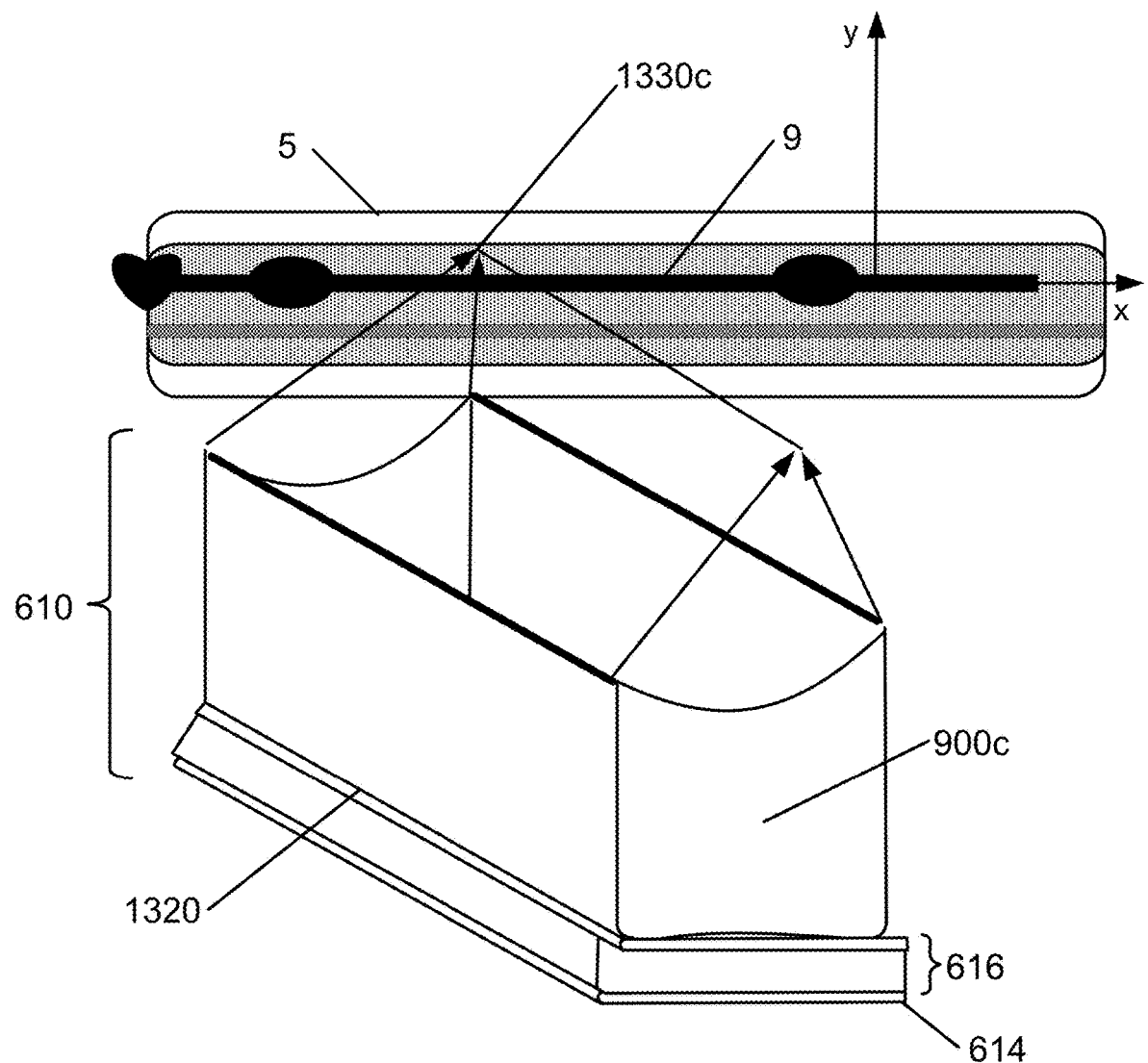

FIGS. 13A and 13B illustrate an ultrasonic sensor system having a focusing layer according to some embodiments. The focusing layer 612 includes lenses 900a 900b (collectively 900) in this example. FIG. 13B shows an example in which the lens 900c is a cylindrical lens, whereas in other implementations at least one of the lenses 900 may be another type of lens, such as a spherical lens. In this example, the beam of ultrasound 1330c, produced from ultrasonic plane waves by the lens 900c, is a linear or substantially linear beam. As an ultrasonic plane wave propagates from the ultrasound transmitter layer 614 through the focusing layer 612, one or more of the lenses 900 (in some examples, each of the lenses 900) may focus the plane wave into a respective beam of ultrasound 1330a, 1330b (collectively 1330) across an arterial longitudinal axis of the artery 9, which corresponds with the x axis in this example. In some embodiments, each beam of ultrasound 30 may be focused perpendicularly across the arterial longitudinal axis of an artery 9 within a limb 5, e.g., along they axis.

However, in alternative implementations the beams of ultrasound may extend across the arterial longitudinal axis of the artery 9, but may not extend perpendicularly across the arterial longitudinal axis. In some such implementations, the beams of ultrasound may extend across the arterial longitudinal axis of the artery 9 at an angle that is within 20 degrees of being perpendicular to the arterial longitudinal axis. In other words, the angle may be within 20 degrees of a normal to the arterial longitudinal axis.

As the artery 9 and the surrounding tissue reflect the focused planar beams of ultrasound, the ultrasonic reflections may propagate back towards the ultrasound transducer layer 1320 of the receiver layer 616. The ultrasound transducer layer 1320 converts the ultrasonic reflections into electrical signals, which are received and amplified by a receiver array (e.g., 1332a or 1332b, collectively 1332) configured in the thin film transistor (TFT) layer 530 of the receiver layer 616.

In the embodiment illustrated in FIG. 13A, the ultrasonic reflections may propagate through the lenses (e.g., 900a or 900b) of the focusing layer 612 prior to impinging on the ultrasound receiver layer 616. In some embodiments, the receiver arrays 1332 may be arranged directly below the lenses 900, thereby increasing the signal-to-noise ratio and reducing beam spreading. In other embodiments, the receiver arrays 1332 may be arranged at a horizontal offset relative to the placement of a respective lens 900a, 900b.

The output signals generated by each of the receiver arrays 532 may be communicated to a processor (e.g., processor 620 of FIG. 6A) for measurement of various cardiovascular properties. For example, the output of a single receiver array 1332a or 1332b may be used by the processor to measure, for example, the cross-sectional area and distension of the artery 9. In embodiments having at least two receiver arrays 1332a and 1332b spaced apart by a known distance along an arterial longitudinal axis, the processor may use the respective outputs of the receiver arrays 532 to determine, for example, a pulse transit time (PTT) and a pulse wave velocity (PWV) of an arterial pressure pulse as it propagates through the artery.

In some embodiments, the processor may be configured to perform certain pre-processing of the output signals to filter out the portions of the output signals that correspond to non-arterial information (i.e., signal contributions due to reflections caused by biological tissues surrounding the artery of interest). For example, in some embodiments, the processor may be configured to search the received output signal from the sensor in sample windows that corresponds to given tissue depths. The window of samples may also be referred to as a range gate. The arterial signal may be identified to be present or not in each range gate by several processing techniques. Some of these techniques would be to compare signal strength of the received signal inside a range gate. Arterial walls will normally give a higher reflection than blood cells. An arterial segment may therefore be identified by observing the shift of intensity from high intensity to low intensity and then again to high intensity which will occur when the range gated signal corresponds to the back side of the artery wall.

Figure 14:
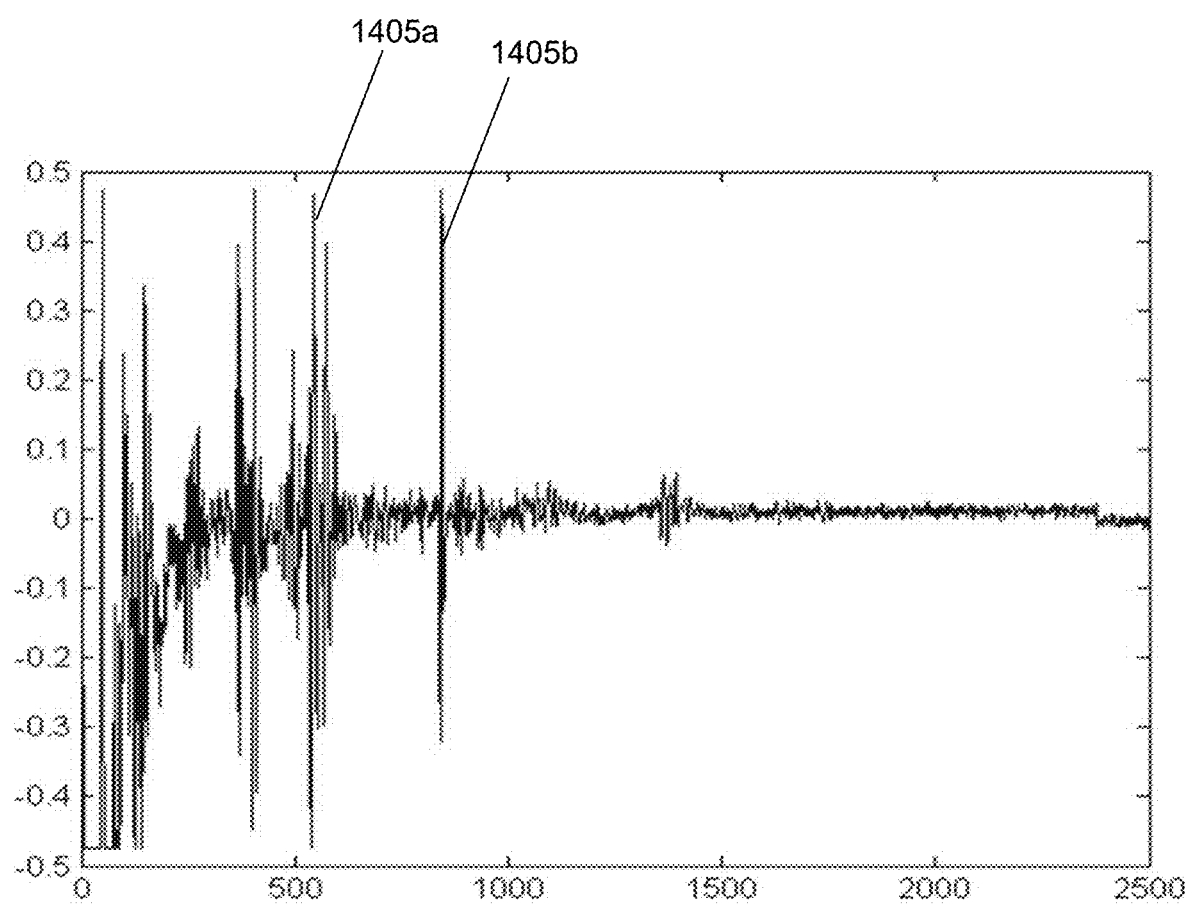
FIG. 14 shows an example of detecting arterial walls according to signals that correspond with ultrasonic reflections.

FIG. 14 shows an example of detecting arterial walls according to signals that correspond with ultrasonic reflections. In this example, the vertical axis corresponds to the signal amplitude received from an ultrasonic receiver element and the horizontal axis corresponds to time. The high-amplitude signals 1405a and 1405b correspond with reflections from an artery wall.

Some implementations may be configured to observe the range gate a given tissue depth over time, e.g., by emitting acoustic waves repeatedly with a given pulse repetition frequency (PRF). When the range gate is located at a depth corresponding to the arterial wall the spikes within the range gate window will be phase shifting or time shifting, which can be tracked emission to emission. In particular, for each pulse repetition a single sample for an arterial waveform similar to the one shown in FIG. 1A may be possible to identify.

Other signal processing methods may involve tracking of the Doppler shift in the signal coming from the vessel wall. Other techniques may involve observing flow profiles.

Figure 15:
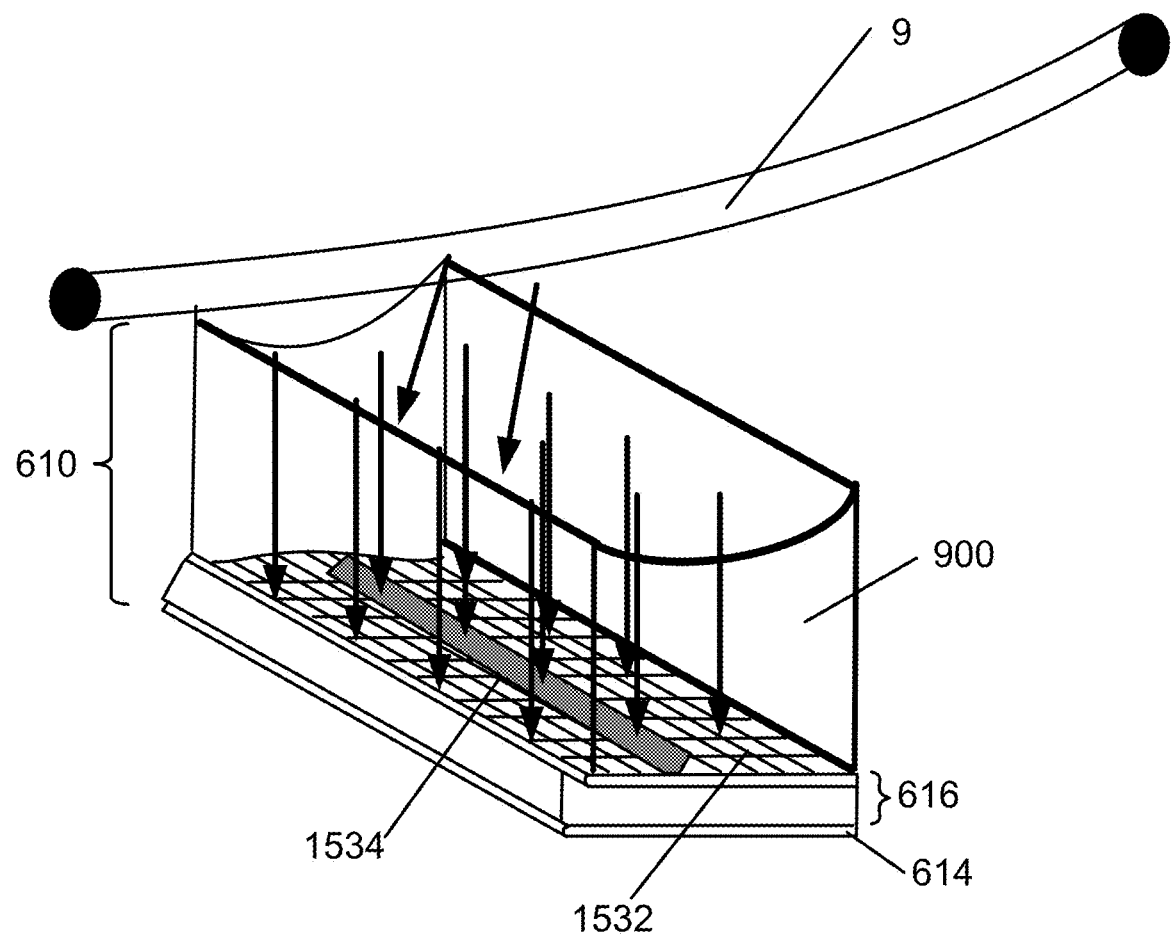
FIG. 15 illustrates an example of a wearable ultrasonic sensor system having at least one cylindrical lens to facilitate an output sampling strategy.

FIG. 15 illustrates an example of a wearable ultrasonic sensor system having at least one cylindrical lens to facilitate an output sampling strategy. As discussed above, a cylindrical lens 900 may be configured to focus ultrasonic plane waves from the ultrasound transmitter layer 614 into a beam of ultrasound 30 across an arterial longitudinal axis of the artery 9. In some such examples, the beam of ultrasound may be a linear, or a substantially linear, beam of ultrasound. The artery 9 and the surrounding tissue may interact with the ultrasound and reflect a portion of the ultrasonic energy back towards the cylindrical lens 900 as ultrasonic reflections.

In the embodiment illustrated in FIG. 6, the cylindrical lens 900 redirects ultrasonic reflections impinging on the lens towards a receiver array 1532 arranged below the ultrasound transducer layer in the ultrasound receiver layer 616. Due to the optics of the cylindrical lens 900, the ultrasonic reflections may be concentrated on a subset of the receiver elements 1534 within the receiver array 1532 (e.g., one or more particular rows and/or columns).

In some embodiments, a processor (e.g., the processor 620 of FIG. 6A) may be configured to sample only the output signals corresponding to the subset of receiver elements 1534 at locations in the receiver array 1532 where the detected ultrasonic reflections is concentrated. As a result, the processor may limit the number of output signals that are sampled from a respective receiver array 1532 and consume less power. In some embodiments, the processor may select the subset of receiver elements 1534 as those receiver elements that produce strongest output signals in terms of signal amplitude. In some embodiments, the processor may adjust the number of receiver elements 1534 selected in order to obtain a desired signal-to-noise ratio.

Figure 16A:
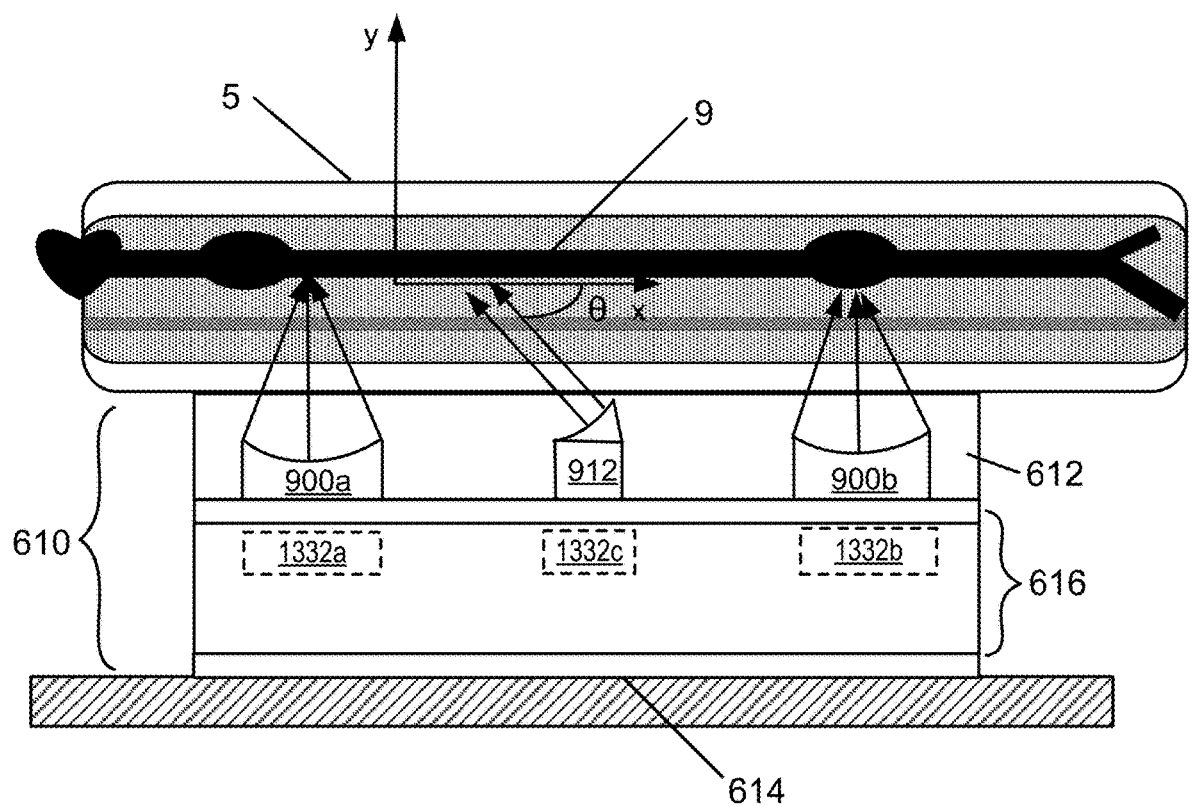
FIG. 16A illustrates an example of a wearable ultrasonic sensor system having a focusing layer according to further embodiments.

FIG. 16A illustrates an example of a wearable ultrasonic sensor system having a focusing layer according to further embodiments. As previously discussed, a focusing layer 612 may include one or more cylindrical lenses 900. The focusing layer 612 may also include a cylindrical lens 912 oriented so that the focused planar beam of ultrasound is emitted at a non-orthogonal angle (θ) relative to the blood flow in an artery (which, in this example, is along the x axis shown in FIG. 16) when the wearable ultrasonic sensor system 610 is positioned on a limb of a subject. Emitting the focused planar beam of ultrasound at a non-orthogonal angle (θ) relative to the blood flow in an artery enables measurements of blood flow velocity and blood flow by measuring the Doppler shift in ultrasonic reflections, and optionally, the intensity of ultrasonic reflections exhibiting varying amounts of Doppler shift.

As discussed above, blood pressure measurements may be obtained by measuring the pulse wave velocity (PWV), arterial distension (δA of FIG. 5B), and mean arterial cross-sectional area (<A> of FIG. 5B). In the foregoing embodiments, pulse wave velocity (PWV) may be determined by detecting the pulse transit time (PTT) between two receiver arrays 1332a, 1332b separated by a fixed distance along the arterial axis in the ultrasound receiver layer 616. By incorporating a cylindrical lens 912 into the focusing layer 612, an alternative method for measuring pulse wave velocity (PWV) may be performed based on measurements of changes in blood flow (dQ) relative to changes in arterial cross-sectional area (dA):

$$PWV = \frac{dQ}{dA}. \tag{11}$$

Changes in blood flow may be determined based on the velocity (v) of the blood flow through an arterial volume (or a cross-sectional area A). For example, in some embodiments, blood flow, Q, may be expressed according to equation (12) as follows:

$$Q = v * A \tag{12}$$

In some embodiments, the blood flow velocity (v) may be determined ultrasonically based on a Doppler shift between frequency of the transmitted ultrasound ($f_t$) and the frequency of the detected ultrasound reflections ($f_r$). For example, the blood flow velocity (v) may be expressed according to equation (13):

$$v = c\frac{(f_r - f_t)}{2f_t \cos\theta}, \tag{13}$$

where θ is a relative angle between the transmitted planar beam of ultrasound and the direction of the blood flow and c is a constant equal to the speed of sound in blood (e.g., 1540 m/s).

In some embodiments, the focusing layer 612 may include a cylindrical lens 912 oriented so that the focused beam of ultrasound is emitted at an angle of approximately 45 degrees relative to the blood flow in the artery when the device is applied to a subject. Blood cells moving within the artery 9 reflect some of the ultrasound back towards the lens 912 with a Doppler-shifted frequency ($f_r$).

As the ultrasonic reflections impinge the cylindrical lens 912, the lens may redirect the ultrasonic reflections towards a receiver array 1332c in the ultrasound receiver layer 616. The receiver array 1332c may detect the ultrasonic reflections and provide output signals corresponding to the detected ultrasonic reflections to a processor (e.g., the processor 620 of FIG. 6A).

In some embodiments, the processor may be configured to measure the Doppler-shifted frequency ($f_r$) from the output signals. In some pulsed Doppler implementations, the time shifted signal may be evaluated at the same range gate depth for each pulse repetition. In some implementations, blood velocity may be measured by cross-correlating two consecutive range gates. Other pulsed Doppler implementations may involve defining a range gate window that covers part of or all of the blood stream and thereafter performing a Fourier transform of the signal to detect the frequency-shifted components. Such implementations can provide satisfactory results for blood vessels that are close to the transducer. Some continuous Doppler implementations may determine the blood velocity according to this method.

Knowing the frequency ($f_t$) of the ultrasonic plane waves generated by the ultrasound transmit layer 614, the measured Doppler-shifted frequencies ($f_r$), and the angle (θ) at which the planar beam of ultrasound is emitted relative to the direction of the blood flow, the processor (e.g., the processor 620 of FIG. 6A) can calculate the blood flow velocity (v) according to equation (13).

Figure 16B:
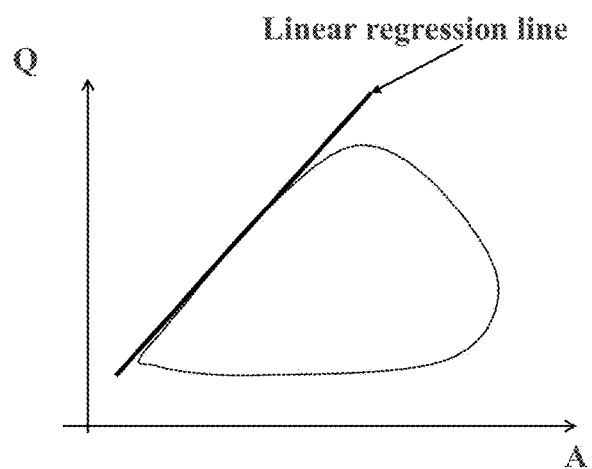
FIG. 16B is a graph that illustrates a relationship between flow and cross-sectional area of an artery during a pulse.

In some embodiments, the processor may measure the changes in arterial cross-sectional area (dA) from the output signals obtained from one of the receiver arrays (e.g., array 1332a, 1332b) arranged beneath one of the lenses (e.g., lenses 900a and 900b). Given these additional measurements, the processor may be configured to calculate changes in blood flow (dQ) and pulse wave velocity (PWV). FIG. 16B is a graph that illustrates a relationship between flow and cross-sectional area of an artery during a pulse. In some examples, the processor may perform an estimation of the slope of a linear regression line that fits a linear part of the QA plot, e.g., as shown in FIG. 16B. The linear part of the slope represents A and Q for the systolic phase of the arterial waveform. The slope can be shown to correspond to the PWV.

Figure 17:
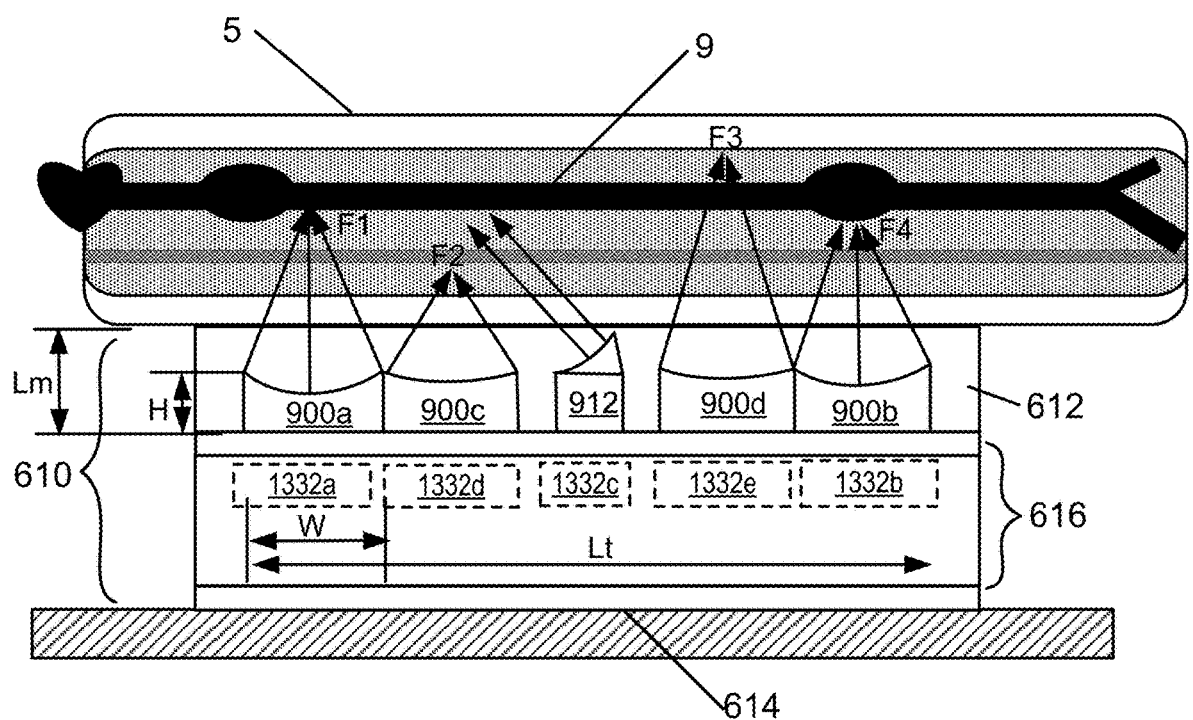
FIG. 17 illustrates a wearable ultrasonic sensor system having a focusing layer including a number of different lenses according to some embodiments.

FIG. 17 illustrates a wearable ultrasonic sensor system having a focusing layer including a number of different lenses according to some embodiments. For example, the focusing layer 612 may include two or more lenses having different focal depths. In some examples, at least one of the lenses may be a cylindrical lens. In the embodiment illustrated in FIG. 17, the lenses have focal depths F1, F2, F3 and F4. Here, the lens 900c is configured with a focal depth F2 that is shorter than the respective focal lengths F1, F3 and F4 of the lenses 900a, 900b, 900c and 900d. The lens 900d is configured with a focal length F4 that is longer than the respective focal depths F1, F2 and F3 of the other cylindrical lenses 900a, 900b and 900c. The focal lengths F1-F4 and the dimensions W, $L_t$, $L_m$ and H that are shown in FIG. 17 are examples of the same dimensions discussed above with reference to FIG. 12 and Tables 3 and 4.

Having multiple lenses configured with different focal lengths enables focusing planar ultrasound beams at different depths in tissues of a subject, which may increase the probability of obtaining an output signal from at least one of the receiver arrays 1332a, 1332b, 1332c, 1332d, and 1332e (collectively receiver arrays 1332) corresponding to ultrasonic reflections from a center of an artery of interest. In some embodiments, a processor (e.g., the processor 620 of FIG. 6A) may be configured to perform a preliminary scan of the output signals from each transducer in the receiver array 1332 to determine the transducer having a signal that is dominated by arterial information suitable for use in measuring the various cardiovascular properties. According to some implementations, the processor may determine this by comparing range gate signals at the same tissue depth. The signal with the highest phase or time shift will most likely be the one that has the best focus on the artery. Other implementations may involve observing the Doppler shift in each range gate. The Doppler shift will generally represent moving tissue.

Figure 18:
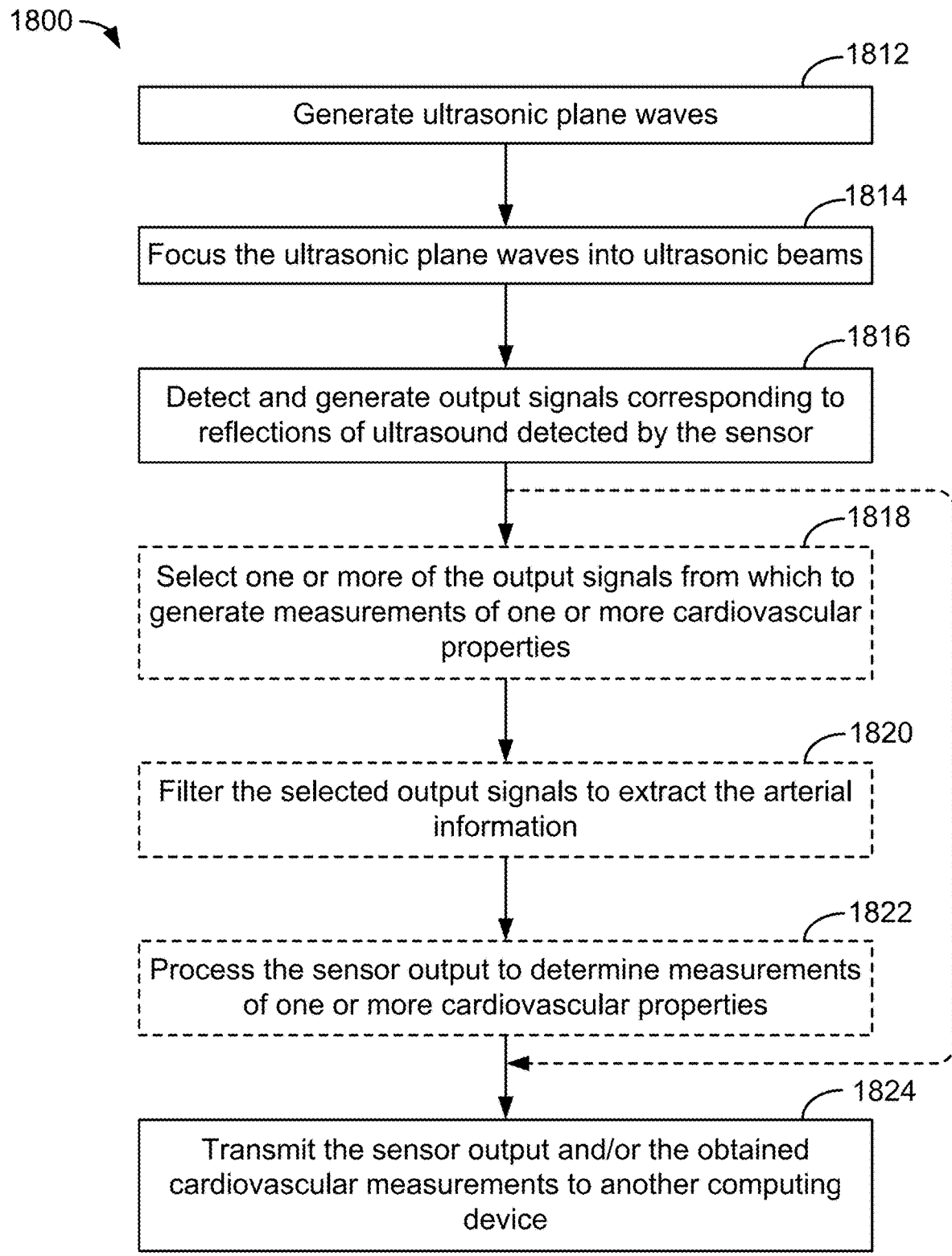
FIG. 18 is a process flow diagram illustrating a method 1800 for determining blood pressure using an ultrasound sensor according to various embodiments.

FIG. 18 is a process flow diagram illustrating a method 1800 for determining blood pressure using an ultrasound sensor according to various embodiments. Various operations of the method 1800 may be performed by a wearable ultrasound measuring device or a mobile computing device configured to measure one or more cardiovascular properties. In some examples, the method may be implemented by the apparatus 180 that is shown in FIG. 1D or the apparatus 600 that is shown in FIG. 6B.

In block 1812, an ultrasonic sensor system according to various embodiments may generate ultrasound pulses, such as ultrasonic plane waves. In some embodiments, an ultrasound transmitter layer 614 may be configured to convert electrical signals from a processor (e.g., the processor 620 of FIG. 6A) into a continuous or pulsed sequence of ultrasonic plane waves.

In block 1814, one or more lenses in a focusing layer of the ultrasonic sensor system may focus the ultrasonic plane waves into a beam of ultrasound that is projected into a subject's limb and across an arterial longitudinal axis of an artery. In some embodiments, the lenses may be configured to have different focal lengths to form multiple focused beams of ultrasound at different depths within the subject. In some embodiments, a lens may be oriented so that the beam of ultrasound is emitted at a non-orthogonal angle relative to the direction of the blood flow.

In block 1816, the ultrasonic sensor system may detect ultrasonic reflections and generate output signals corresponding to reflections of the planar beam of ultrasound. In some embodiments, an ultrasound receiver layer 616 of the ultrasonic sensor system 610 may convert reflections of ultrasound into electrical signals that may be received by respective receiver arrays. In response, each of the respective receiver arrays may be configured to generate an output corresponding to the detected ultrasonic reflections.

In optional block 1818, a processor (e.g., 620) may select one or more of the output signals from which to generate measurements of one or more cardiovascular properties. For example, in some embodiments, the processor may be configured to sample only a subset of output signals that may be provided by a receiver array. For example, as previously described with respect to FIG. 15, the processor may be configured to sample only a subset of output signals (e.g., the strongest output signals) from individual elements of a receiver array 1532. In some embodiments, the processor may be configured to select the output signals from the receiver arrays 1532 that correspond to ultrasonic reflections obtained from a particular focal depth, e.g., preferably at a focal depth corresponding to an artery of interest.

In optional block 1820, the processor (e.g., 620) may filter the selected output signals from the respective receiver arrays in order to obtain filtered output signals that are dominated by signal contributions from an artery of interest. For example, in some embodiments, the processor may be configured to pass the output signals from the ultrasound sensor through a high pass filter having a cut-off frequency in the order of 0.5-50 Hertz (Hz) or lower. As a result, the signal contributions corresponding to reflections by blood cells moving through the artery (i.e., arterial information) are maintained, while signal contributions from slowly moving tissues surrounding the artery in the limb of the subject are removed from the output signals.

In optional block 1822, the processor (e.g., 620) may process the sensor output, including the optionally selected and filtered sensor output from blocks 1818 and 1820, to determine measurements of one or more cardiovascular properties. For example, as described above, the processor may use the output signals from the ultrasound sensor to calculate a variety of cardiovascular properties, such as arterial beat-to-beat distension, pulse transit time (PTT), pulse wave velocity (PWV), mean arterial cross-sectional area, blood velocity, blood flow, and blood pressure. For example, calculations of blood pressure may involve applying known or estimated properties of tissues, such as a stress-strain relationship of an artery, distance or distension measurements reflected in the sensor output to calculate pressure. As another example, the processor may process the sensor outputs from two ultrasound sensors separated by a known distance to recognize when a pulse pressure wave passes under each sensor from changes in distension, and use the known distance divided by the time to calculate pulse wave velocity in the artery. As a further example, the processor may process the sensor outputs from the ultrasound sensors to estimate distension or diameter of the artery.

In block 1824, the processor may transmit the output and/or the obtained measurements to another computing device, such as via an RF module (e.g., 630) and an antenna (e.g., 632). For example, the processor may transmit calculated cardiovascular property measurements to a mobile device, such as a smartphone, via a wireless signal, such as a WLAN, for display to an operator. The computing device may store, process, and/or display calculated cardiovascular property measurements.

In some embodiments, the output generated by the ultrasound sensor in block 1816 may be transmitted directly to another computing device, such as a smartphone. In such embodiments, the computing device may calculate cardiovascular properties from the output signals, enabling the use of a limited capability processor in a wearable ultrasound measuring device 100.

Those of skill in the art will appreciate that the foregoing method descriptions and process flow diagrams are provided merely as illustrative examples and are not intended to require or imply that the steps of the various embodiments must be performed in the order presented. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope embodiments.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

The functions in the various embodiments may be implemented in hardware, software, firmware, or any combination thereof. If implemented in software, the functions may be stored as one or more processor executable instructions or code on a non-transitory computer readable medium or non-transitory processor readable medium. The steps of a method or algorithm disclosed herein may be embodied in a processor-executable software module that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the claims. Various modifications to these embodiments will be readily apparent to those skilled in the art, and the generic principles defined herein may be applied to other embodiments without departing from the scope of the claims. Thus, the claims are not intended to be limited to the embodiments shown herein but are to be accorded the widest scope consistent with the claims and the principles and novel features disclosed herein.

The invention claimed is:

1. A method of estimating a blood pressure comprising:
    performing, by one or more sensors of a non-interfering device that is configured to be worn on a subject's limb, two or more measurements, wherein at least two measurements from the two or more measurements correspond to different measurement elevations of the subject's limb, wherein the performing the two or more measurements involves controlling the non-interfering device to perform the two or more measurements without impeding blood flow of an underlying blood vessel and wherein the non-interfering device does not perturb a blood vessel being measured;
    determining, by a processor, a blood flow difference based on the two or more measurements;
    determining, by the processor, a hydrostatic pressure difference based on the different measurement elevations of the two or more measurements; and
    estimating, by the processor, the blood pressure based on a first blood flow, a second blood flow, the hydrostatic pressure difference and the blood flow difference, wherein the one or more sensors include one or more optical sensors of an optical sensor system and wherein the performing, by the one or more sensors, the two or more measurements comprises:
        directing, by the optical sensor system, light waves towards an artery to form a measuring volume having an interference pattern that illuminates at least an interior portion of the artery, wherein the measuring volume comprises a volume of the artery towards which the light waves are directed, wherein a cross-sectional diameter of the measuring volume is greater than a diameter of the artery and wherein the interference pattern of the measuring volume has a fringe spacing greater than a diameter of blood cells;

receiving, by the one or more sensors, one or more reflected waves, wherein the one or more reflected waves are based at least in part on the directed light waves and wherein the one or more reflected waves include backscattered light waves;

obtaining, by the one or more sensors, the two or more measurements, including the at least two measurements taken at each of the different measurement elevations, based on the one or more reflected waves; and transmitting, by the one or more sensors, the two or more measurements to the processor;

wherein determining the blood flow difference based on the two or more measurements comprises:

determining, by the processor, values of arterial lumen for each of the different measurement elevations wherein the values of arterial lumen include values of arterial cross-section or arterial volume;

determining, by the processor, a value of blood velocity associated with each of the different measurement elevations based, at least in part, on a Doppler shift or a Doppler shift related signal corresponding to the backscattered light waves; and determining, by the processor, the first blood flow associated with a first measurement elevation and the second blood flow associated with a second measurement elevation based on the determined values of the blood velocity and the determined values of the arterial lumen; and wherein estimating the blood pressure involves determining an arterial stress-strain relationship based on the hydrostatic pressure difference, the determined values of the blood velocity and the determined values of the arterial lumen.

2. The method of claim 1, wherein the one or more reflected waves include scattered waves, specularly reflected waves, or both scattered waves and specularly reflected waves.

3. The method of claim 1, wherein the light waves include one or more of infrared light and visible light.

4. The method of claim 1, wherein the determined values of the arterial lumen comprise values of arterial cross-section or arterial volume.

5. The method of claim 1, wherein the one or more sensors further include one or more ultrasonic sensors.

6. The method of claim 5, wherein the two or more measurements comprises directing ultrasonic waves into the subject's limb towards an artery.

7. The method of claim 1, further comprising at least one of storing or transmitting, by the processor, an indication or estimation of a blood pressure.

8. A system for estimating a blood pressure comprising:

a non-interfering device configured to be worn on a subject's limb, the non-interfering device comprising a sensor system; and a control system comprising one or more processors, the control system being configured for communication with the sensor system, the control system configured to:

control one or more sensors of the sensor system to perform two or more measurements, wherein at least two measurements of the two or more measurements correspond to different measurement elevations of a subject's limb, wherein performing the two or more measurements involves controlling the non-interfering device to perform the two or more measurements without impeding blood flow of an underlying blood vessel and wherein the non-interfering device does not perturb a blood vessel being measured;

determine a blood flow difference based on the two or more measurements;

determine a hydrostatic pressure difference based on the different measurement elevations of the two or more measurements; and estimate the blood pressure based on a first blood flow, a second blood flow, the hydrostatic pressure difference and the blood flow difference, wherein the one or more sensors include one or more optical sensors of an optical sensor system and wherein performing, by the one or more sensors, the two or more measurements comprises:

directing, by the optical sensor system, light waves towards an artery to form a measuring volume having an interference pattern that illuminates at least an interior portion of the artery, wherein the measuring volume comprises a volume of the artery towards which the light waves are directed, wherein a cross-sectional diameter of the measuring volume is greater than a diameter of the artery and wherein the interference pattern of the measuring volume has a fringe spacing greater than a diameter of blood cells;

receiving, by the one or more sensors, one or more reflected waves, wherein the one or more reflected waves are based at least in part on the directed light waves and wherein the one or more reflected waves include backscattered light waves;

obtaining, by the one or more sensors, the two or more measurements, including the at least two measurements taken at each of the different measurement elevations, based on the one or more reflected waves; and transmitting, by the one or more sensors, the two or more measurements to the control system;

wherein determining the blood flow difference based on the two or more measurements comprises:

determining, by the control system, values of arterial lumen for each of the different measurement elevations, wherein the values of arterial lumen include values of arterial cross-section or arterial volume;

determining, by the control system, a value of blood velocity associated with each of the different measurement elevations based, at least in part, on a Doppler shift or a Doppler shift related signal corresponding to the backscattered light waves; and determining, by the control system, the first blood flow associated with a first measurement elevation and the second blood flow associated with a second measurement elevation based on the determined values of the blood velocity and the determined values of the arterial lumen; and wherein estimating the blood pressure involves determining an arterial stress-strain relationship based on the hydrostatic pressure difference, the determined values of the blood velocity and the determined values of the arterial lumen.

9. The system of claim 8, wherein the one or more reflected waves include scattered waves, specularly reflected waves, or both scattered waves and specularly reflected waves.

10. The system of claim 8, wherein the light waves include one or more of infrared light and visible light.

11. The system of claim 8, wherein the one or more sensors further include one or more ultrasonic sensors.

12. The system of claim 11, wherein the two or more measurements comprises directing ultrasonic waves into the subject's limb towards an artery.

13. A system for estimating a blood pressure comprising:
a non-interfering device configured to be worn on a subject's limb, the non-interfering device comprising a sensor system; and
control means configured for communication with the sensor system, the control means including means for:
controlling one or more sensors of the sensor system to perform two or more measurements, wherein at least two measurements of the two or more measurements correspond to different measurement elevations of a subject's limb, wherein performing the two or more measurements involves controlling the non-interfering device to perform the two or more measurements without impeding blood flow of an underlying blood vessel and wherein the non-interfering device does not perturb a blood vessel being measured;
determining a blood flow difference based on the two or more measurements;
determining a hydrostatic pressure difference based on the different measurement elevations of the two or more measurements; and
estimating the blood pressure based on a first blood flow, a second blood flow, the hydrostatic pressure difference and the blood flow difference, wherein the one or more sensors include one or more optical sensors of an optical sensor system and wherein performing, by the one or more sensors, the two or more measurements comprises:
directing, by the optical sensor system, light waves towards an artery to form a measuring volume having an interference pattern that illuminates at least an interior portion of the artery, wherein the measuring volume comprises a volume of the artery towards which the light waves are directed, wherein a cross-sectional diameter of the measuring volume is greater than a diameter of the artery and wherein the interference pattern of the measuring volume has a fringe spacing greater than a diameter of blood cells;
receiving, by the one or more sensors, one or more reflected waves, wherein the one or more reflected waves are based at least in part on the directed light waves and wherein the one or more reflected waves include backscattered light waves;
obtaining, by the one or more sensors, the two or more measurements, including the at least two measurements taken at each of the different measurement elevations, based on the one or more reflected waves; and
transmitting, by the one or more sensors, the two or more measurements to the control means;
wherein determining the blood flow difference based on the two or more measurements comprises:
determining, by the control means, values of arterial lumen for each of the different measurement elevations, wherein the values of arterial lumen include values of arterial cross-section or arterial volume;
determining, by the control means, a value of blood velocity associated with each of the different measurement elevations based, at least in part, on a Doppler shift or a Doppler shift related signal corresponding to the backscattered light waves; and
determining, by the control means, the first blood flow associated with a first measurement elevation and the second blood flow associated with a second measurement elevation based on the determined values of the blood velocity and the determined values of the arterial lumen; and
wherein estimating the blood pressure involves determining an arterial stress-strain relationship based on the hydrostatic pressure difference, the determined values of the blood velocity and the determined values of the arterial lumen.

14. The system of claim 13, wherein the sensor system further includes an ultrasonic sensor system and wherein the performing, by the one or more sensors, the two or more measurements further comprises directing ultrasonic waves into the subject's limb towards an artery.

15. A non-transitory medium having software stored thereon, the software including instructions for:
controlling one or more sensors of a non-interfering device configured to be worn on a subject's limb, the non-interfering device comprising a sensor system, to perform two or more measurements, wherein at least two measurements of the two or more measurements correspond to different measurement elevations of the subject's limb, wherein performing the two or more measurements involves controlling the non-interfering device to perform the two or more measurements without impeding blood flow of an underlying blood vessel and wherein the non-interfering device does not perturb a blood vessel being measured;
determining a blood flow difference based on the at least two measurements;
determining a hydrostatic pressure difference based on the different measurement elevations of the at least two measurements; and
estimating a blood pressure based on a first blood flow, a second blood flow, the hydrostatic pressure difference and the blood flow difference, wherein the one or more sensors include one or more optical sensors of an optical sensor system and wherein performing, by the one or more sensors, the two or more measurements comprises:
directing, by the optical sensor system, light waves towards an artery to form a measuring volume having an interference pattern that illuminates at least an interior portion of the artery, wherein the measuring volume comprises a volume of the artery towards which the light waves are directed, wherein a cross-sectional diameter of the measuring volume is greater than a diameter of the artery and wherein the interference pattern of the measuring volume has a fringe spacing greater than a diameter of blood cells;
receiving, by the one or more sensors, one or more reflected waves, wherein the one or more reflected waves are based at least in part on the directed light waves and wherein the one or more reflected waves include backscattered light waves;
obtaining, by the one or more sensors, the two or more measurements, including the at least two measurements taken at each of the different measurement elevations, based on the one or more reflected waves; and transmitting, by the one or more sensors, the two or more measurements to a control system;

wherein determining the blood flow difference based on the two or more measurements comprises:

determining, by the control system, values of arterial lumen for each of the different measurement elevations wherein the values of arterial lumen include values of arterial cross-section or arterial volume;

determining, by the control system, a value of blood velocity associated with each of the different measurement elevations based, at least in part, on a Doppler shift or a Doppler shift related signal corresponding to the backscattered light waves; and determining, by the control system, the first blood flow associated with a first measurement elevation and the second blood flow associated with a second measurement elevation based on the determined values of the blood velocity and the determined values of the arterial lumen; and wherein estimating the blood pressure involves determining an arterial stress-strain relationship based on the hydrostatic pressure difference, the determined values of the blood velocity and the determined values of the arterial lumen.

16. The non-transitory medium of claim 15, wherein the sensor system further includes an ultrasonic sensor system and wherein the performing, by the one or more sensors, the two or more measurements further comprises directing ultrasonic waves into the subject's limb towards the artery.

* * * * *